US007485631B2

(12) United States Patent
Razler et al.

(10) Patent No.: US 7,485,631 B2
(45) Date of Patent: Feb. 3, 2009

(54) PHORBOXAZOLE COMPOUNDS AND METHODS OF THEIR PREPARATION

(75) Inventors: Thomas M. Razler, Yardley, PA (US);
Amos B. Smith, III, Merion, PA (US);
Jeffrey P. Ciavarri, Reading, MA (US);
Tomoyasu Hirose, Kawasaki (JP);
Tomoyasu Ishikawa, Ohtsu (JP)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 11/408,573

(22) Filed: Apr. 20, 2006

(65) Prior Publication Data
US 2007/0021479 A1 Jan. 25, 2007

Related U.S. Application Data

(60) Provisional application No. 60/674,004, filed on Apr. 21, 2005.

(51) Int. Cl.
*A01N 43/00* (2006.01)
*A61K 31/33* (2006.01)
*C07D 225/00* (2006.01)
*C07D 295/00* (2006.01)

(52) U.S. Cl. .................................. 514/183; 540/450
(58) Field of Classification Search .................. None
See application file for complete search history.

(56) References Cited

U.S. PATENT DOCUMENTS 6,797,721 B2* 9/2004 Uckun et al. ............. 514/375

FOREIGN PATENT DOCUMENTS

WO    WO 01/36048 A1    5/2001

OTHER PUBLICATIONS

Forsyth et al. Bioorganic & Medicianl Chemistry Letters, 2003, 13, 2127-2130.*
Smith et al. Journal of the American Chemical Society, 2001, 123, 10942-10953.*
Greene et al. Protective Groups in Organic Synthesis, 1999, pp. 123-141.*
Ahmed, F. et al., "Convergent Synthesis of the C31-C46 Domain of the Phorboxazole Natural Products," *Tetrahedron Lett.*, 1998, 39, 183-186.
Boeckman, R. K. et al., "A Convergent General Synthetic Protocol for Construction of Spirocyclic Ketal Ionophores: An Application to the Total Synthesis of (-)-A-23187 (Calcimycin)," *J. Am. Chem. Soc.*, 1987, 109, 7553-7555.
Cohen, Y., et al., "Reaction of C2-Symmetrical Dialkoxysilanes $R_1O$-$Si(R_2)_2$-$OR_1$ with the two Vilsmeier-Haack Complexes $POCl_3$_DMF and $(CF_3SO_2)_2O$_DMF: An Efficient One-Step Conversion to the Corresponding Formates $R_1$-OCHO," *Synlett.*, 2001, 1543-1546.

Cywin, C. L. et al., "Synthesis of (-)-(6R,10R)-Matsuone. Assignment of Relative Stereochemistry to a Pheromone of *Matsucoccus* Pine Bast Scales," *J. Org. Chem.*, 1991, 56, 2953-2955.
Evans, D. A. et al, "Asymmetric Synthesis of Phorboxazole B—Part I: Synthesis of the $C_{20}$-$C_{38}$ and $C_{39}$-$C_{46}$ Subunits," *Angew. Chem. Int. Ed.*, 2000, 39(14), 2533-2536.
Evans, D. A. et al., "Application of Complex Aldol Reactions to the Total Synthesis of Phorboxazole B," *J. Am. Chem. Soc.*, 2000, 122, 10033-10046.
Evans, D. A. et al., "Enantioselective Aldol Condensations. 2. Erythro-Selective Chiral Aldol Condensations via Boron Enolates," *J. Am. Chem. Soc.*, 1981, 103, 2127-2129.
Forsyth, C. J. et al., "Total Synthesis of Phorboxazole A," *J. Am Chem. Soc.*, 1998, 120, 5597-5598.
Keck, G. E. et al. "Catalytic Enantioselective Synthesis of Dihydropyrones *via* Formal Hetero Diels-Alder Reactions of "Danishefsky's Diene" with Aldehydes," *J. Org. Chem.*, 1995, 60, 5998-5999.
Molinski, T. F. et al., "Absolute Configuration of Phorboxazoles A and B from the Marine Sponge *Phorbas* sp. 1. Macrolide and Hemiketal Rings," *J. Am. Chem. Soc.* 1996, 118, 9422-9423.
Molinski, T. F. et al., "Phorboxazoles A and B: Potent Cytostatic Macrolides from Marine Sponge *Phorbas* Sp.," *J. Am. Chem. Soc.*, 1995, 117, 8126-8131.
Molinski, T. F., "Absolute Configuration of Phorboxazoles A and B from the Marine Sponge, *Phorbas*Sp. 2. C43 and Complete Stereochemistry," *Tetrahedron Lett.*, 1996, 37(44), 7879-7880.
Nagoa, Y. et al. "Use of Chiral 1,3-Oxazolidine-2-thiones in the Diastereoselective Synthesis of Aldols," *J. Chem. Soc. Chem. Com.*, 1985, 1418-1419.
Noyori, R. et al., "Trimethysilyl Triflate in Organic Synthesis," *Tetrahedron*, 1981, 37(23), 3899-3910.
Panek, J. S. et al., "Total Synthesis of (-)-Mycalolide A," *J. Am. Chem. Soc.*, 2000, 122, 1235-1236.
Pattenden, G. et al., "A Convergent Total Synthesis of Phorboxazole A," *Angew. Chem. Int. Ed.*, 2003, 42(11), 1255-1258.
Sharma, M. L. et al., "Synthesis Of (±)-2-Methyl-(2'-Hydroxy-4'-Methylphenyl)-2- Hepten-4-One (Turmeronol B)," *Tetrahedron Lett.*, 37(13), 1996, 2279-2280.
Smith, A. B. et al. "(+)-Phorboxazole A Synthetic Studies. Identification of a Series of Highly Cytotoxic C(45-46) Analogues," *Org. Lett.*, 2005, 7(20), 4403-4406.
Smith, A. B. et al., "Phorboxazole Synthetic Studies. 1. Construction of a C(3-19) Subtarget Exploiting an Extension of the Petasis-Ferrier Rearrangement," *Org. Lett.*, 1999, 1(6), 909-912.
Smith, A. B. et al., "Phorboxazole Synthetic Studies. 2. Construction of a C(20-28) Subtarget, a Further Extension of the Petasis-Ferrier Rearrangement," *Org. Lett.*, 1999, 1(6), 913-916.

(Continued)

*Primary Examiner*—James O. Wilson
*Assistant Examiner*—Noble Jarrell
(74) *Attorney, Agent, or Firm*—Woodcock Washburn LLP

(57) ABSTRACT

Novel macrolactone compounds, their methods of preparation, pharmaceutical compositions containing these compounds, and methods for their pharmaceutical use are disclosed. In certain embodiments, the macrolactone compounds may be useful, inter alia, for treating various cancers, inducing apoptosis in malignant cells, or inhibiting cancer cell division.

21 Claims, No Drawings

OTHER PUBLICATIONS

Smith, A. B. et al., "Total Synthesis of (+)-Phorboxazole A Exploiting the Petasis-Ferrier Rearrangement," *J. Am. Chem. Soc.*, 2001, 123, 10942-10953.

Smith, A. B. et al., "Total Synthesis of (+)-Phorboxazole A," *J. Am. Chem. Soc.*, 2001, 123, 4834-4836.

Smith, A.B., et al., "Design and Synthesis of a Potent Phorboxazole C(11-15) Acetal Analogue," *Org. Lett.*, 2006, 8(4), 797-799.

Still, W. C. et al., "Direct Synthesis of Z-Unsaturated Esters. A Useful Modification of the Horner-Emmons Olefination," *Tetrahedron Lett.*, 1983, 24(41), 4405-4408.

Uckun, F. A. et al. "Anticancer Activity of Synthetic Analogues of the Phorboxazoles," *Bioorg. Med. Chem. Lett.*, 2001, 11, 1181-1183.

Williams, D. R. et al., "Total Synthesis A," *Angew. Chem. Int. Ed.*, 2003, 42(11), 1258-1262.

Yamashita, Y., et al. "Chiral Hetero Diels-Alder Products by Enantioselective and Diastereoselective Zirconium Catalysis. Scope, Limitation, Mechanism, and Application to the Concise Synthesis of (+)-Prelactone C and (+)-9-Deoxygoniopypyrone," *J. Am. Chem. Soc.*, 2003, 125, 3793-3798.

* cited by examiner

PHORBOXAZOLE COMPOUNDS AND METHODS OF THEIR PREPARATION

CROSS REFERENCE TO RELATED APPLICATIONS

This application claims priority to U.S. Provisional Application Ser. No. 60/674,004, filed Apr. 21, 2005, the disclosure of which is incorporated herein by reference in its entirety.

GOVERNMENT SUPPORT

Certain of the inventors were supported by National Institutes of Health Grant CA019033.

FIELD OF THE INVENTION

The invention relates to compounds which mimic the chemical and/or biological activity of Phorboxazole, compositions containing such compounds, and to methods useful in their preparation. More particularly, the present invention relates to novel Phorboxazole analogs that may be useful as pharmaceuticals in inducing apoptosis in cancer cells.

BACKGROUND OF THE INVENTION

In 1995, Searle and Molinski (*J. Am. Chem. Soc.* 1995, 117, 8126-8131; *J. Am. Chem. Soc.* 1996, 118, 9422-9423; *Tetrahedron Lett.* 1996, 37, 7879-7880) isolated (+)-Phorboxazole A (1) and B (2) from a methanolic extract of the sponge *Phorbas* sp. In vitro bioassay against the National Cancer Institute's (NCI) panel of 60 human tumor cell lines revealed extraordinary anti-proliferative activity against the entire panel; a mean $GI_{50}$ value of $1.58 \times 10^{-9}$ M for both (+)-Phorboxazole A and B.

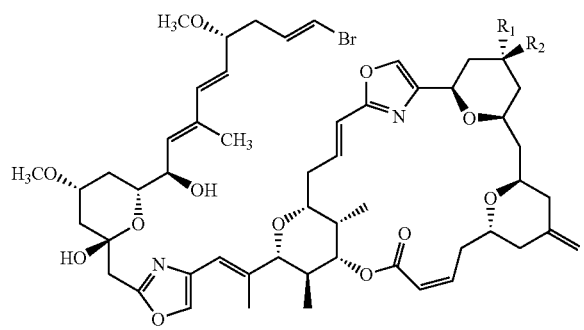

XVIII (1) (+)-phorboxazole A $R_1$=OH, $R_2$=H
(2) (+)-phorboxazole B $R_1$=H, $R^2$=OH While (1) and (2) remain promising anticancer medicinal agents, their architectural complexity warrants exploration of simplified synthetic analogs. Initial structure activity relationship (SAR) studies conducted by Uckun (WO 01/36048 A1) and Forsyth (*Bioorg. Med. Chem. Lett.* 2001, 11, 1181-1183) disclosed the discovery of two (+)-Phorboxazole A analogues which displayed anticancer activity in leukemia, breast cancer, and brain tumor cancer cell lines.

Several groups have been actively involved in devising synthetic routes to Phorboxazole A and/or Phorboxazole B. Forsyth, et al. (*J. Am Chem. Soc.* 1998, 120, 5597) have reported a linear synthetic sequence of 100 total steps to Phorboxazole A in 0.4% overall yield. Smith, et al., (*J. Am. Chem. Soc.* 2001, 123, 4834) have prepared Phorboxazole A in an overall yield of 3%. Pattenden, et al., (*Angew. Chem. Int. Ed.* 2003, 42, 1255) have provided Phorboxazole A in 0.18% overall yield. A 2.4% overall yield of Phorboxazole A was reported by Williams, et al. (*Angew. Chem. Int. Ed.* 2003, 42, 1258). Evans, et al (*Angew. Chem. Int. Ed.* 2000, 39, 2533, 2536) have developed a route to Phorboxazole B of 71 total steps in 12.6% overall yield.

There is therefore a need for improved synthetic methods which provide high yield and high selectivity, and at a relatively high rate of reaction, using better, more convenient and/or less expensive process methodology than many processes known heretofore for the preparation of Phorboxazole A, Phorboxazole B, their synthetic intermediates, and for compounds, analogs or derivatives having similar chemical and/or biological activity. The present invention is directed to these and other important ends.

SUMMARY OF THE INVENTION

Accordingly, the present invention is directed in part to novel methods for the preparation of Phorboxazole A, Phorboxazole B, and their synthetic intermediates. In certain aspects, the invention is directed to new analogs and derivatives of Phorboxazole A and Phorboxazole B having useful chemical and/or biological activity. In other aspects, the invention is directed to methods of preparation for, compositions containing, and methods of use of analogs or derivatives of Phorboxazole A or Phorboxazole B.

DETAILED DESCRIPTION OF ILLUSTRATIVE EMBODIMENTS

As employed above and throughout the disclosure, the following terms, unless otherwise indicated, shall be understood to have the following meanings.

"Alkyl" refers to an optionally substituted, saturated straight, or branched, hydrocarbon radical having from about 1 to about 20 carbon atoms (and all combinations and subcombinations of ranges and specific numbers of carbon atoms therein). Alkyl groups include, but are not limited to, methyl, ethyl, n-propyl, isopropyl, n-butyl, isobutyl, t-butyl, n-pentyl, isopentyl, neopentyl, n-hexyl, isohexyl, 3-methylpentyl, 2,2-dimethylbutyl, and 2,3-dimethylbutyl.

"Alkenyl" refers to an optionally substituted alkyl group having from about 2 to about 10 carbon atoms and one or more double bonds (and all combinations and subcombinations of ranges and specific numbers of carbon atoms therein), wherein alkyl is as previously defined.

"Alkynyl" refers to an optionally substituted alkyl group having from about 2 to about 10 carbon atoms and one or more triple bonds (and all combinations and subcombinations of ranges and specific numbers of carbon atoms therein), wherein alkyl is as previously defined.

"Aryl" refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

"Aralkyl" refers to an optionally substituted moiety composed of an alkyl radical bearing an aryl substituent and having from about 6 to about 50 carbon atoms (and all combinations and subcombinations of ranges and specific numbers of carbon atoms therein), with from about 6 to about 10 carbon atoms being preferred. Non-limiting examples include, for example, benzyl, diphenylmethyl, triphenylmethyl, phenylethyl, and diphenylethyl.

"Halo" refers to iodo, bromo, chloro, or fluoro.

Typically, substituted chemical moieties include one or more substituents that replace hydrogen. Exemplary substituents include, for example, halo (e.g., F, Cl, Br, I), alkyl, cycloalkyl, alkylcycloalkyl, alkenyl, alkynyl, aralkyl, aryl, heteroaryl, heteroaralkyl, spiroalkyl, heterocycloalkyl, hydroxyl (—OH), oxo (=O), nitro (—NO$_2$), cyano (—CN), amino (—NH$_2$), —N-substituted amino (—NHR"), —N,N-disubstituted amino (—N(R")R"), carboxy (—COOH), —O—C(=O)R", —C(=O)R", —OR", —C(=O)OR", —NHC(=O)R", aminocarbonyl (—C(=O)NH$_2$), —N-substituted aminocarbonyl (—C(=O)NHR"), —N,N-disubstituted aminocarbonyl (—C(=O)N(R")R"), thiol, thiolato (—SR"), sulfonic acid (—SO$_3$H), phosphonic acid (—PO$_3$H), —P(=O)(OR")OR", S(=O)R", —S(=O)$_2$R", —S(=O)$_2$NH$_2$, —S(=O)$_2$NHR", —S(=O)$_2$NR"R", —NHS(=O)$_2$R", —NR"S(=O)$_2$R", —CF$_3$, —CF$_2$CF$_3$, —NHC(=O)NHR", —NHC(=O)NR"R", —NR"C(=O)NHR", —NR"C(=O)NR"R", —NR"C(=O)R" and the like. In relation to the aforementioned substituents, each moiety R" can be, independently, any of H, alkyl, cycloalkyl, alkenyl, aryl, aralkyl, heteroaryl, or heterocycloalkyl, or when two R" groups are attached to the same nitrogen atom within a substituent, as herein above defined, R" and R" can be taken together with the nitrogen atom to which they are attached to form a 3- to 8-membered heterocycloalkyl ring, wherein one or two of the heterocycloalkyl ring carbon atoms independently may be optionally replaced by —O—, —S—, —SO, —SO$_2$—, —NH—, —N(alkyl)-, —N(acyl)-, —N(aryl)-, or —N(aroyl)-groups, for example.

When any variable occurs more than one time in any constituent or in any formula, its definition in each occurrence is independent of its definition at every other occurrence. Combinations of substituents and/or variables are permissible only if such combinations result in stable compounds.

Accordingly, the present invention is directed, in part, to compounds of formula XIX:

XIX

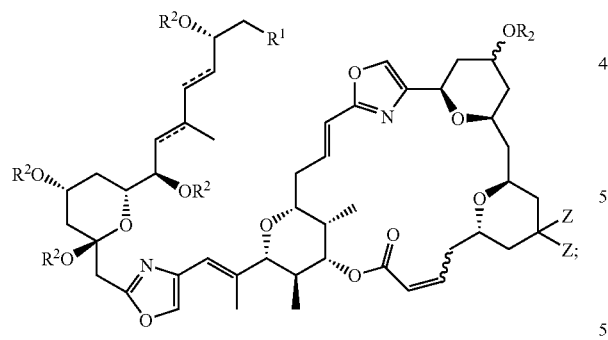

wherein:
R$^1$ is alkyl, alkenyl, haloalkenyl, alkynyl, or silylated alkynyl;
each R$^2$ is independently H, alkyl, aralkyl, aryl, or an hydroxyl protecting group;
each dotted line indicates independently the presence of a single or double bond; and
each Z is H or taken together form an exocyclic methylene moiety;
provided that when the compound of formula XIX has the structure:

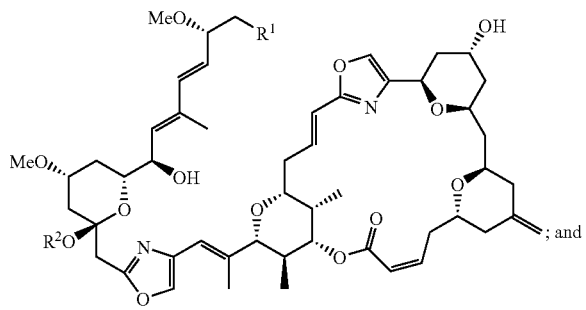

R$^2$ is H or methyl;
then R$^1$ is other than:

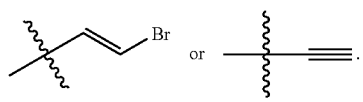

In certain preferred embodiments the compound of formula XIX has the following structure:

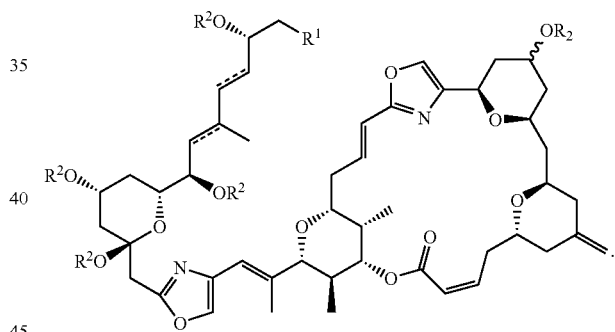

In other preferred embodiments the compound of formula XIX has the following structure:

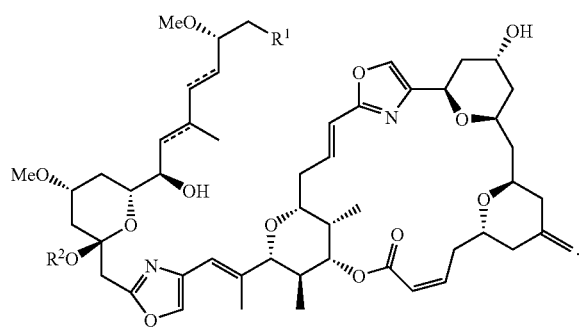

Preferably, when the compound of formula XIX has the above formula, R$^1$ is:

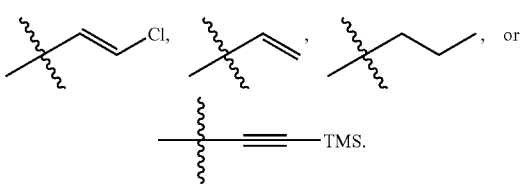

In certain embodiments, the present invention is directed, in part, to compounds of formula XXII:

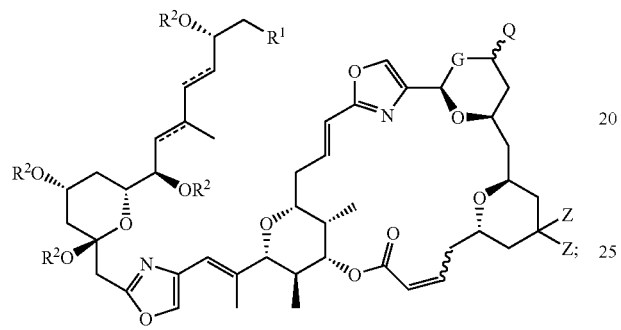

XXII wherein:
G is —O— or —CH$_2$—;
Q is H or OR$^2$, provided that when G is —O—, then Q is H;
R$^1$ is alkyl, alkenyl, haloalkenyl, or alkynyl;
each R$^2$ is independently H, alkyl, aralkyl, aryl, or an hydroxyl protecting group;
each dotted line indicates independently the presence of a single or double bond; and
each Z is H or taken together form an exocyclic methylene moiety;
provided that when the compound of formula XXII has the structure:

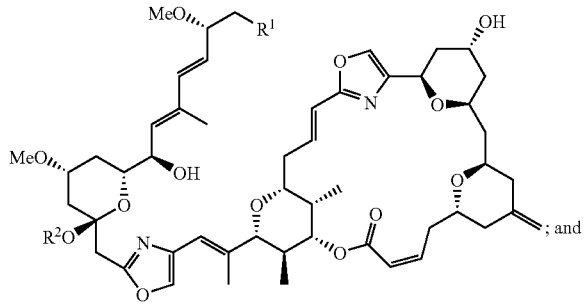

R$^2$ is H or methyl;
then R$^1$ is other than:

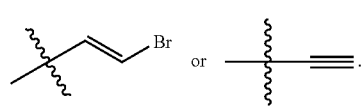

In certain embodiments of compounds of the invention, such as for example compounds of formula XIX, XX, XXI, XXII, XXIII, and/or XXIV, R$^1$ is alkyl, alkenyl, haloalkenyl, or alkynyl. Alternatively, in certain embodiments, R$^1$ is more preferably alkyl, alkenyl, or alkynyl. In embodiments wherein R$^1$ is alkyl, it is preferably C$_1$-C$_6$ alkyl, more preferably C$_1$-C$_3$ alkyl, more preferably C$_1$-C$_2$ alkyl, yet more preferably ethyl or methyl. In embodiments wherein R$^1$ is alkenyl, it is preferably it is preferably C$_2$-C$_6$ alkenyl, more preferably C$_2$-C$_3$ alkenyl, more preferably ethenyl. In embodiments wherein R$^1$ is haloalkenyl, it is preferably alkenyl substituted with chloro or bromo, more preferably C$_2$-C$_3$ alkenyl substituted with one chloro or bromo, still more preferably chloroethenyl or bromoethenyl, with Z-chloroethenyl or Z-bromoethenyl being particularly preferred. In embodiments wherein R$^1$ is alkynyl it is preferably C$_2$-C$_6$ alkynyl, more preferably C$_2$-C$_3$ alkynyl, more preferably ethynyl. In certain preferred embodiments wherein R$^1$ is alkynyl, it is silylated, more preferably silylated ethynyl, more preferably still tetrabutyldimethylsilylated ethynyl.

Alternatively, R$^1$ is preferably:

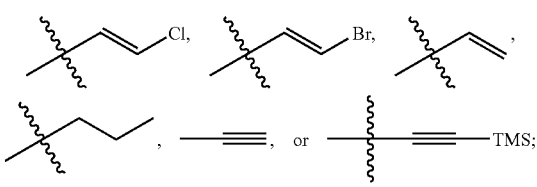

more preferably:

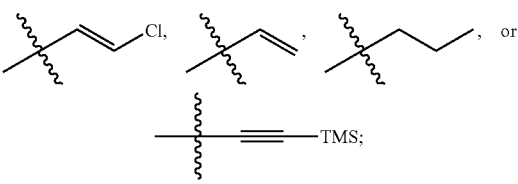

with:

being even more preferred.

In other embodiments of compounds of the invention, such as for example compounds of formula XIX, XX, XXI, XXII, XXIII, and/or XXIV, each R$^2$ is independently H, alkyl, aralkyl, aryl, or an hydroxyl protecting group. When R$^2$ is alkyl, it is preferably C$_1$-C$_6$ alkyl, more preferably C$_1$-C$_3$ alkyl, more preferably C$_1$ alkyl, yet more preferably methyl. When R$^2$ is aralkyl, it is preferably optionally substituted benzyl; when substituted, the phenyl ring of said benzyl is preferably substituted with at least one alkoxy, preferably methoxy moiety. When R$^2$ is aryl, it s preferably phenyl.

The target compounds and intermediates of the present invention may contain hydroxyl protecting groups. Protecting groups are known per se as chemical functional groups that can be selectively appended to and removed from functionality present in a chemical compound to render such functionality inert to certain chemical reaction conditions to which the compound is exposed. When R$^2$ an hydroxyl protecting group, it may be any hydroxyl group utilized by one of ordinary skill in the art. For example, see Greene and Wuts, "*Protective Groups in Organic Synthesis*", 2$^{nd}$ Ed. Wiley and Sons, NY, 1991, the contents of said reference incorporated herein in its entirety. Numerous hydroxyl protecting groups are known in the art, including the acid-labile t-butyldimethylsilyl, diethylisopropylsilyl, and triethylsilyl groups and the acid-stable aralkyl (e.g., benzyl), triisopropylsilyl, and t-butyldiphenylsilyl groups. Preferably, the protecting group is a silyl protecting group, such as for example, tertbutyldimethylsilyl, triisopropylsilyl, tertbuylbisphenylsilyl, and the like.

In certain preferred embodiments the compound of formula XXII has the following structure:

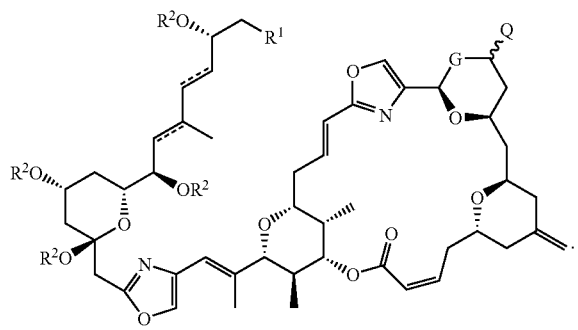

In other preferred embodiments, the compound of formula XXII has the following structure:

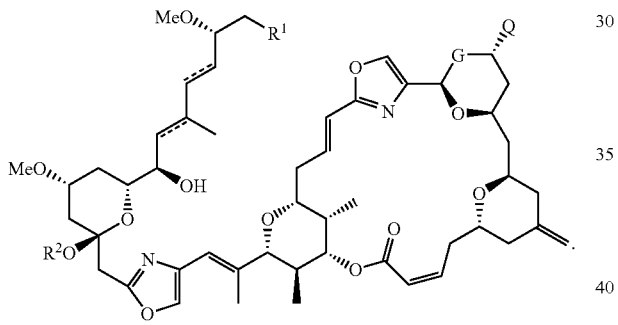

In other embodiments, the invention is directed to processes for preparing a compound of formula XIX:

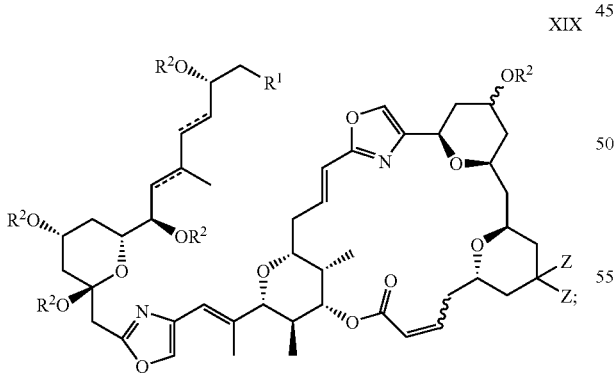

XIX wherein:
R$^1$ is alkyl, alkenyl, haloalkenyl, or alkynyl;
each R$^2$ is independently H, alkyl, aralkyl, aryl, or an hydroxyl protecting group;
each dotted line indicates independently the presence of a single or double bond; and
each Z is H or taken together form an exocyclic methylene moiety, comprising the steps of:

contacting a compound of formula XX:

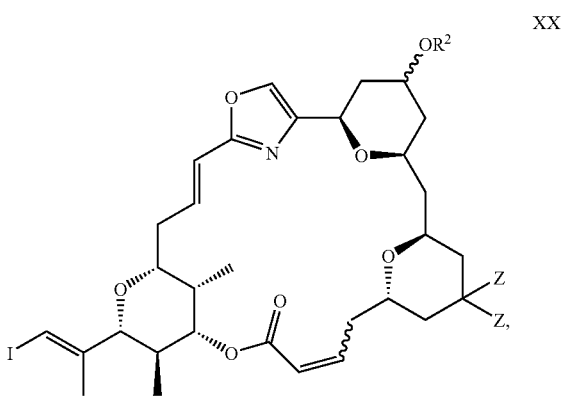

XX with a compound of formula XXI:

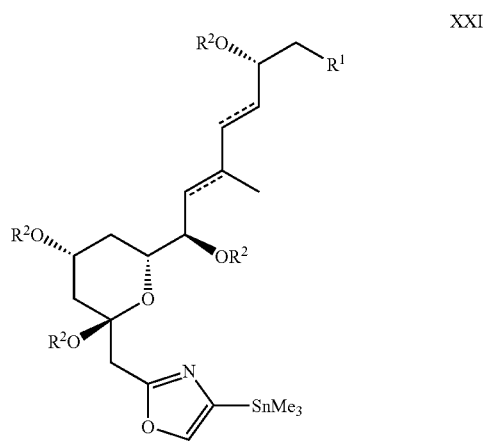

XXI wherein:
R$^1$ is alkyl, alkenyl, haloalkenyl, or alkynyl; and
each R$^2$ is independently H, alkyl, aralkyl, aryl, or hydroxyl protecting group;
for a time and under conditions effective to provide a compound of formula XIX.

In other embodiments, the invention is directed to processes for preparing a compound of formula XIX:

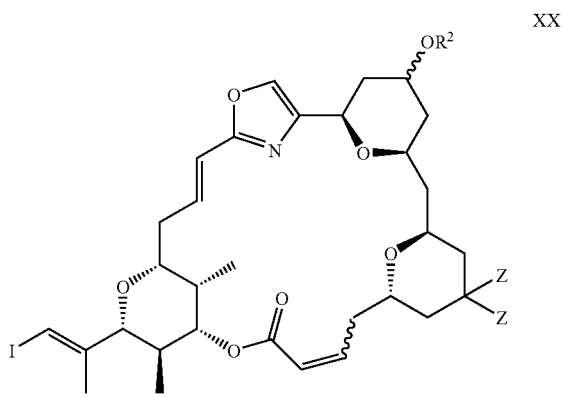

XX wherein:
each $R^2$ is independently H, alkyl, aralkyl, aryl, or an hydroxyl protecting group; and
each Z is H or taken together form an exocyclic methylene moiety, comprising the steps of:
contacting a compound of formula:

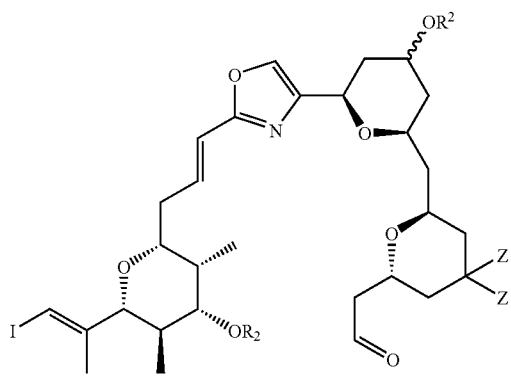

with a compound of formula:

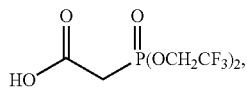

a lactonization agent, and a base for a time and under conditions effective to provide a compound of formula XX.

In other embodiments, the invention is directed to processes for preparing a compound of formula XXII:

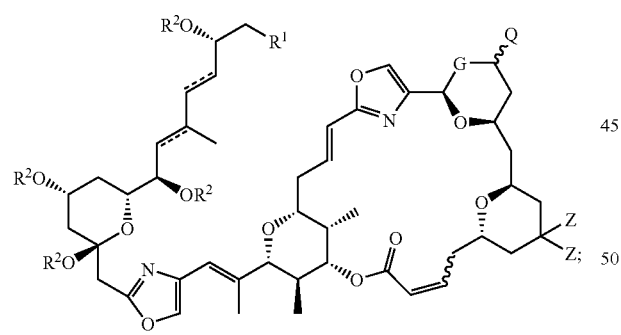

wherein:
G is —O— or —CH$_2$—;
Q is H or OR$^2$, provided that when G is —O—, then Q is H;
R$^1$ is alkyl, alkenyl, haloalkenyl, or alkynyl;
each R$^2$ is independently H, alkyl, aralkyl, aryl, or an hydroxyl protecting group;
each dotted line indicates independently the presence of a single or double bond; and
each Z is H or taken together form an exocyclic methylene moiety, comprising the steps of:
contacting a compound of formula XXIII:

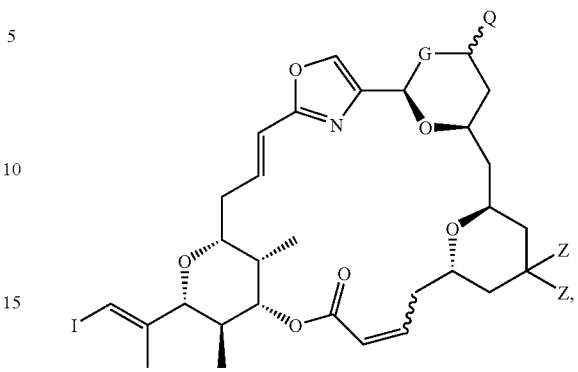

with a compound of formula XXIV:

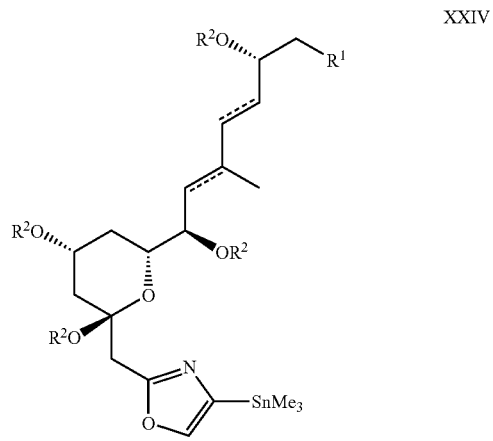

wherein:
R$^1$ is alkyl, alkenyl, haloalkenyl, or alkynyl; and
each R$^2$ is independently H, alkyl, aralkyl, aryl, or hydroxyl protecting group;
for a time and under conditions effective to provide a compound of formula XXII.

The present invention is also directed, in part, to processes for preparing a compound of formula XXIII:

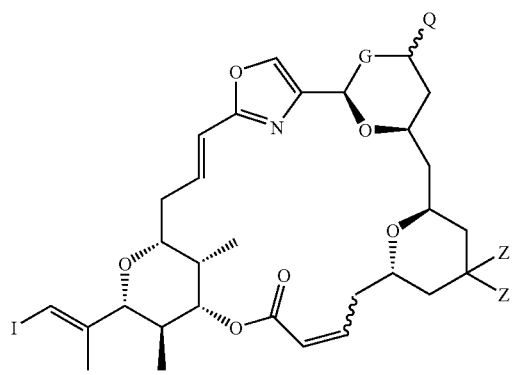

wherein:
each R² is independently H, alkyl, aralkyl, aryl, or an hydroxyl protecting group; and
each Z is H or taken together form an exocyclic methylene moiety, comprising the steps of:
contacting a compound of formula:

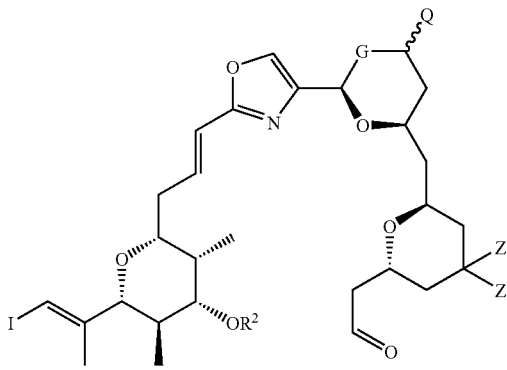

with a compound of formula:

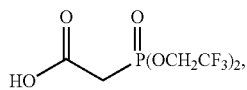

a lactonization agent, and a base for a time and under conditions effective to provide a compound of formula XXIII.

Although the compounds of the present invention may be administered as the pure chemicals, it is preferable to present the active ingredient as a pharmaceutical composition. The invention thus further provides a pharmaceutical composition comprising one or more of the cannabinoid receptor modulator compounds of the present invention, together with one or more pharmaceutically acceptable carriers therefore and, optionally, other therapeutic and/or prophylactic ingredients. The carrier(s) must be acceptable in the sense of being compatible with the other ingredients of the composition and not deleterious to the recipient thereof.

The compounds of formula XIX and/or XXII are preferably combined with a pharmaceutical carrier selected on the basis of the chosen route of administration and standard pharmaceutical practice as described, for example, in *Remington's Pharmaceutical Sciences* (Mack Pub. Co., Easton, Pa., 1980), the disclosure of which is hereby incorporated herein by reference, in its entirety.

In other preferred embodiments, the invention is directed, in part, to methods of inducing apoptosis in malignant cells, comprising the step of contacting said cells with an effective amount of a compound of the invention, such as, for example a compound of formula formula XIX, XX, XXI, XXII, XXIII, and/or XXIV. In certain more preferred embodiments, apoptosis occurs in vitro. In other more preferred embodiments, apoptosis occurs in vivo.

Among preferable embodiments included herein, the invention is directed, in part, to methods for inhibiting cancer cell division, comprising the step of contacting said cells with an effective amount of a compound of the invention.

In certain preferred embodiments, the invention is directed, in part, to methods for treating cancer in a patient in need thereof, comprising the step of administering to said patient an effective amount of a compound of the invention, such as for example, a compound of formula XIX, XX, XXI, XXII, XXIII, and/or XXIV; preferably wherein the cancer treated is selected from the group consisting of pancreatic, breast, central nervous system, non-small lung, colon, and prostate cancers.

Methods of Preparation

The previously disclosed compound I (Smith, et al., *J. Am. Chem. Soc.* 2001, 123, 10942) was provided (Scheme I) by the application of aspects of methodology of Keck, et al. (*J. Org. Chem.* 1995, 60, 5998) and Yamashita, et al. (*J. Am. Chem. Soc.* 2003, 125, 3793) from known aldehyde 2.100 of Boeckman, et al. (*J. Am. Chem. Soc.* 1987, 109, 7553).

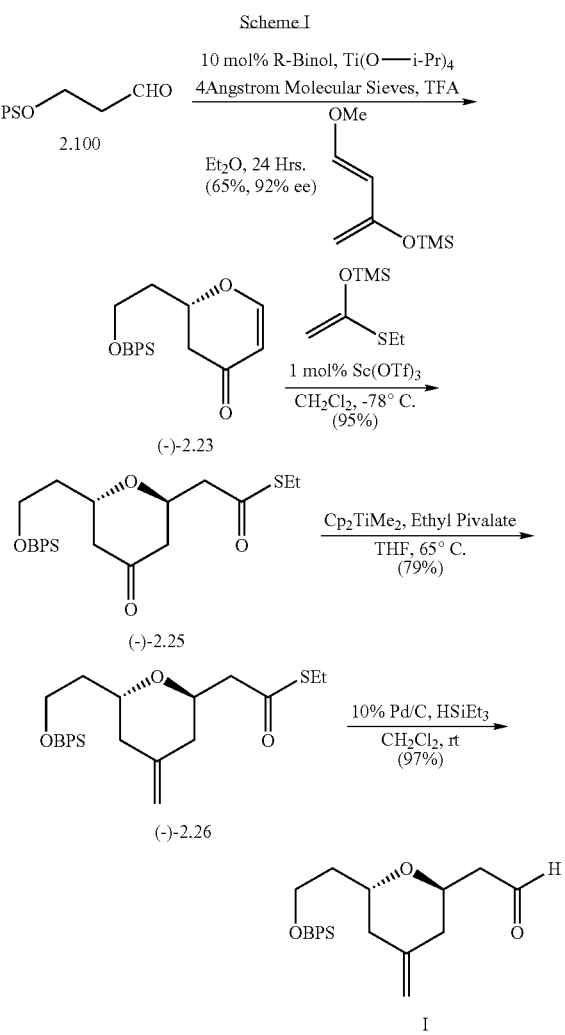

Compound I was transformed into II (Scheme II) by the application of aspects of methodology of Nagao, et al., *J. Chem. Soc. Com.* 1985, 1418, Petasis, et al., *Tetrahedron Lett.* 1996, 2279, and Smith, et al., *Org. Lett.* 1999, 1, 909. The oxazolyl aldehyde 3.48 utilized in the second reaction step (Scheme II) and tetrahydropyranone II were previously disclosed in Smith, et al. (*J. Am. Chem. Soc.* 2001, 123, 10942-53).

Scheme II

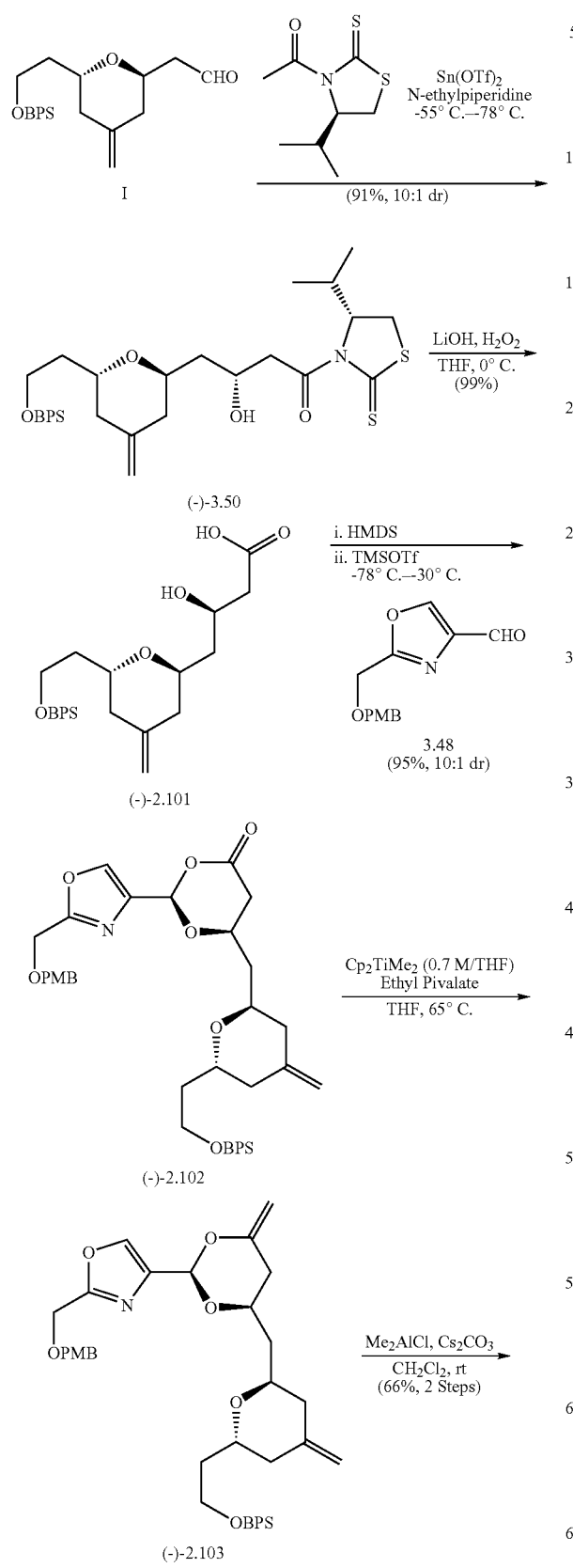

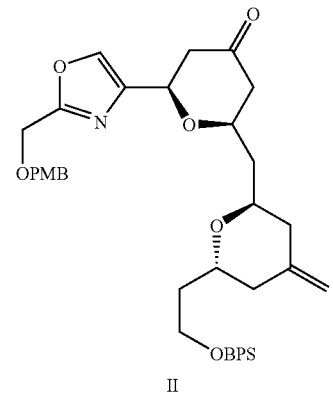

II was selectively reduced to the corresponding axial alcohol (−)-2.104 using K-Selectride (this isomer was utilized in the preparation of Phorboxazole A and all analogs with similar stereochemistry at this center) followed by protection of the secondary alcohol with tert-butyldimethylsilyl triflate. PMB Deprotection with DDQ followed by mesylation gave III [(−)-2.51] in 29% overall yield. Alternatively, the equatorial alcohol may be provided by reducing II with, for example sodium borohydride, by inference of borohydride reductions on similar substrates. Utilization of the equatorial alcohol, upon completion of the remaining steps described in Scheme III, would then provide the isomer used in the preparation of Phorboxazole B.

Scheme III

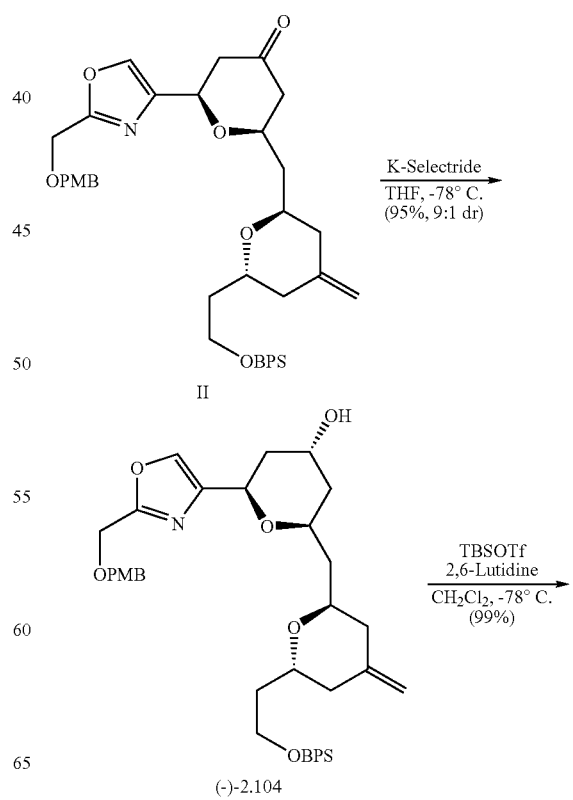

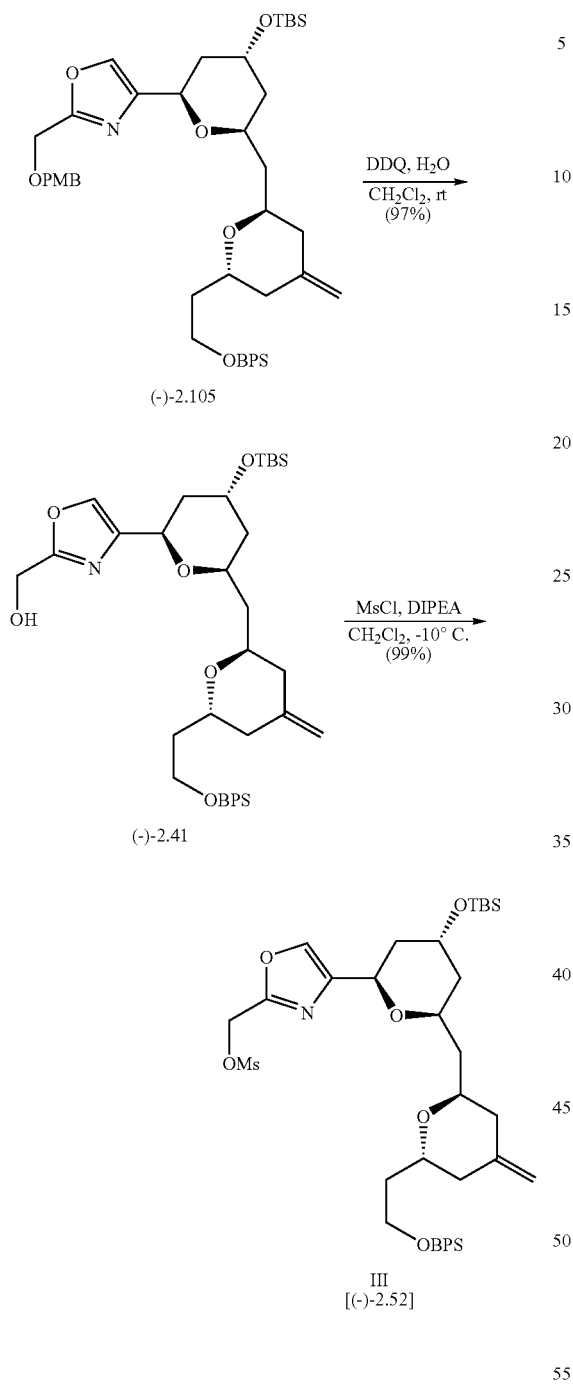

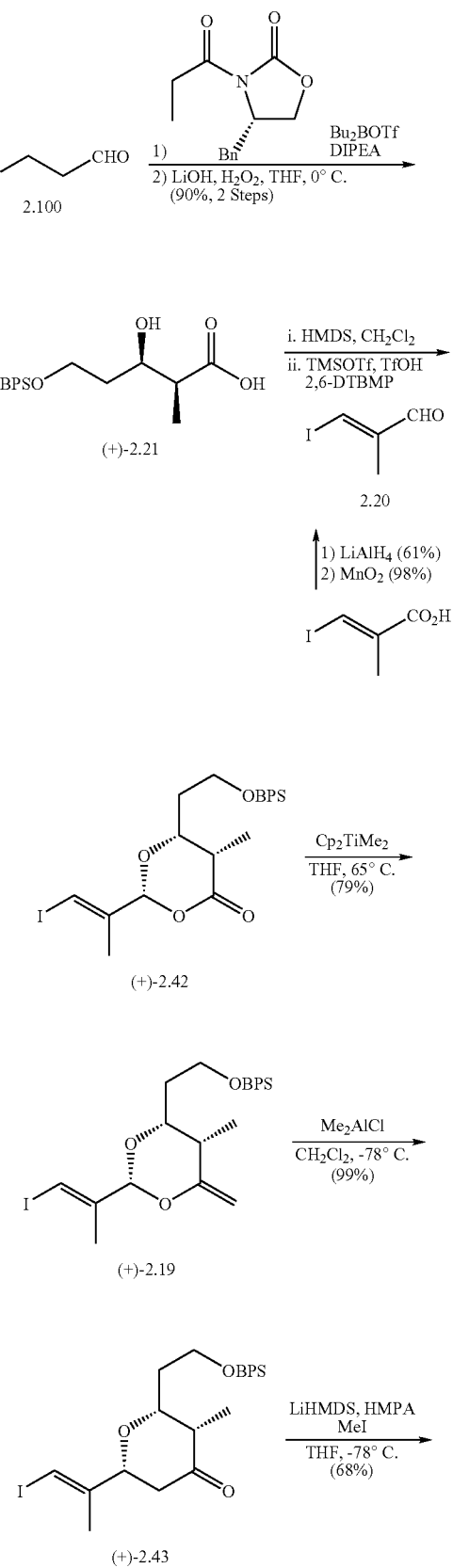

Intermediate IV [(+)-2.44] was prepared in 35% overall yield (Scheme IV) applying aspects of the chemistry of Evans, et al. (*J. Am. Chem. Soc.* 1981, 103, 2127) from known β-hydroxy carboxylic acid (+)-2.21 of Smith, et al. (*Org. Lett.* 1999, 1, 913). (In Scheme IV, the following abbreviations have these meanings: Bu$_2$BOTf is dibutylboron triflate, HMDS is hexamethyldisilazide, 2,6-DTBMP is 2,6-di-tert-butyl-4-methylpyridine, DMBCl is 3,4-dimethoxybenzyl chloride, and BORSM is based on recovered starting material.)

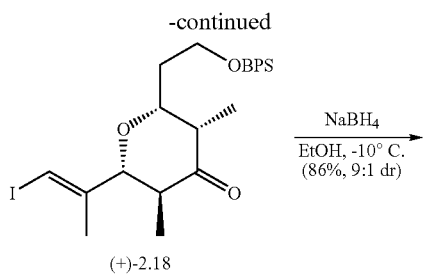

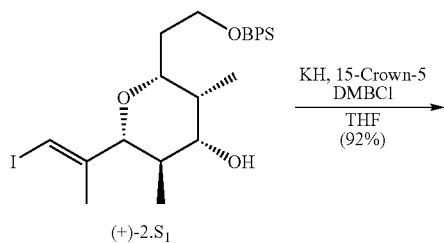

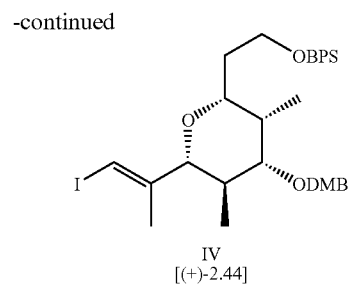

The chemistry of Liu, et al. (*J. Am. Chem. Soc.* 2000, 122, 1235) and Evans, et al. (*J. Am. Chem. Soc.* 2000, 122, 10033) was effectively applied for the preparation of VI [(+)-2.461] from III [(−)-2.52] and IV [(+)-2.44]. Removal of the silyl protecting group of IV with subsequent Dess-Martin oxidation of the primary alcohol gave aldehyde V [(+)-2.12] in 94% yield. V was then converted via Wittig olefination with the phosphonium salt derived from III [(−)-2.52] in DMF to provide VI [(+)-2.46] with 20:1 E/Z selectivity in 94% yield, as shown in Scheme V.

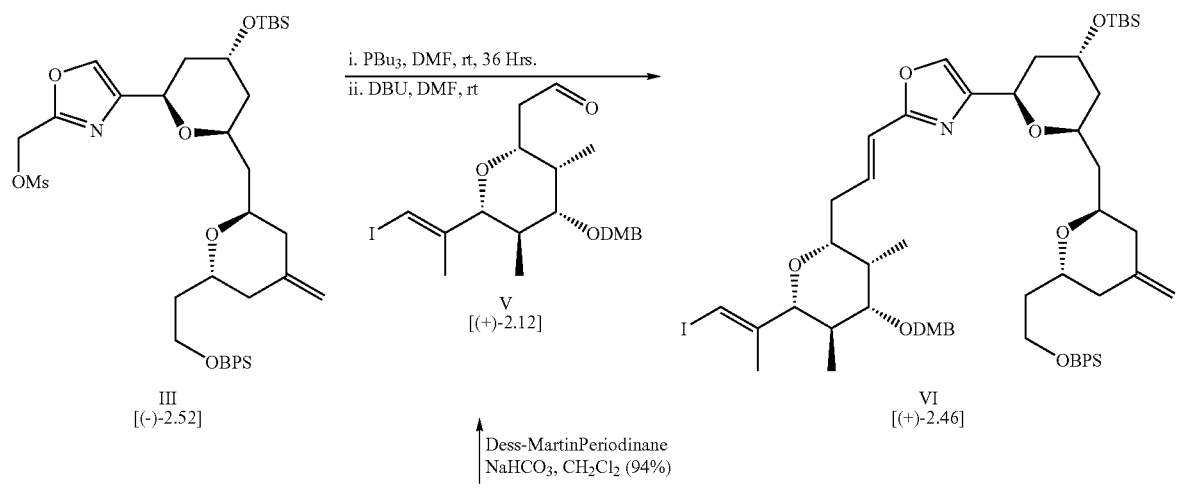

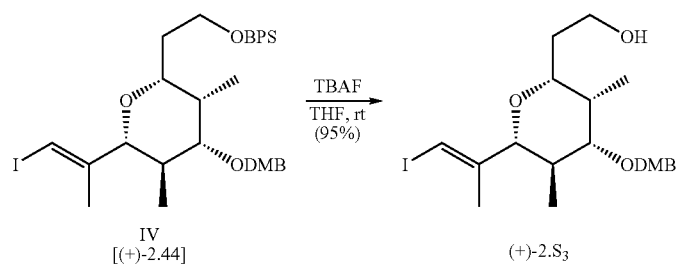

The silylated primary alcohol VI [(+)-2.46] was deprotected with KOH and then oxidized using Dess-Martin chemistry to give, after DMB removal with DDQ, the aldehyde of formula VII [(+)-2.10]. Phosphonate type Wittig reaction of VII [(+)-2.10] entailed coupling with the phosphonate carboxylic acid 3.45, and olefination to provide VIII [(+)-2.5] in 18% overall yield. The E and Z isomers of VIII [(+)-2.5] were separable using medium pressure column chromatography using silica gel (Scheme VI).

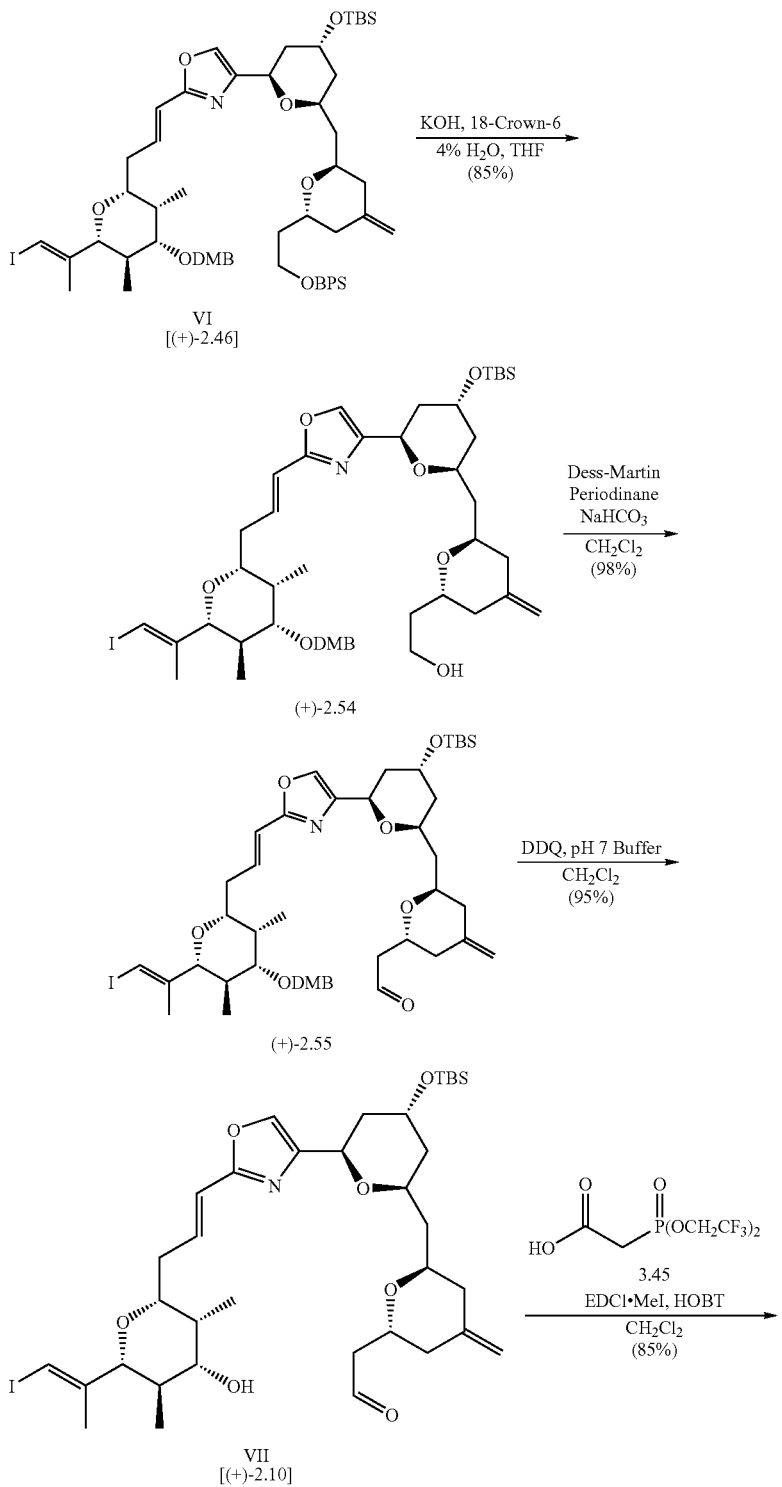

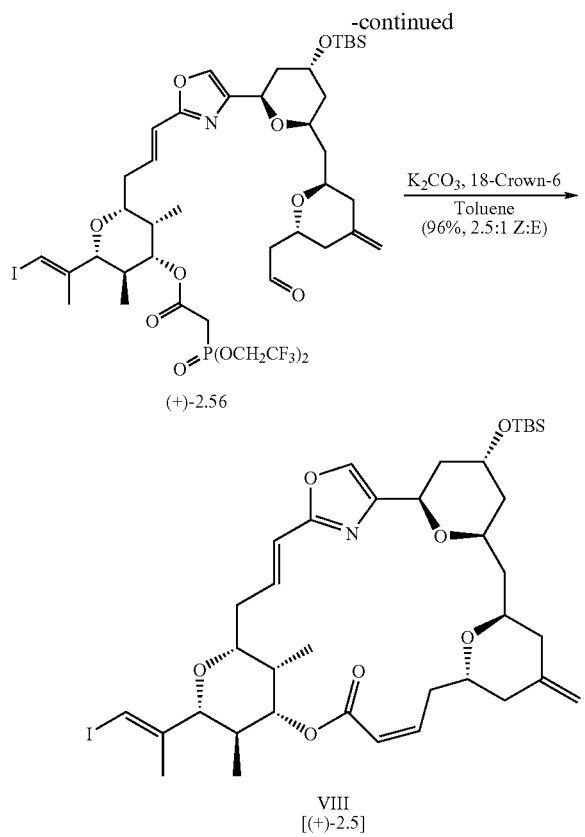
IX was reacted with a TMS protected acetylenyl stannane under conditions earlier disclosed in Smith, et al. (*Synlett.* 2001, 1543, and in *J. Am. Chem. Soc.* 2001, 123, 10942-53) and further converted to X [(−)-2.S$_5$]. X [(−)-2.S$_5$] was stannylated with hexamethylditin in the presence of a palladium catalyst to give XI [(−)-2.90]. TIPS stands for the silyl protecting group triisopropylsilyl in the schemes herein(Scheme VII).
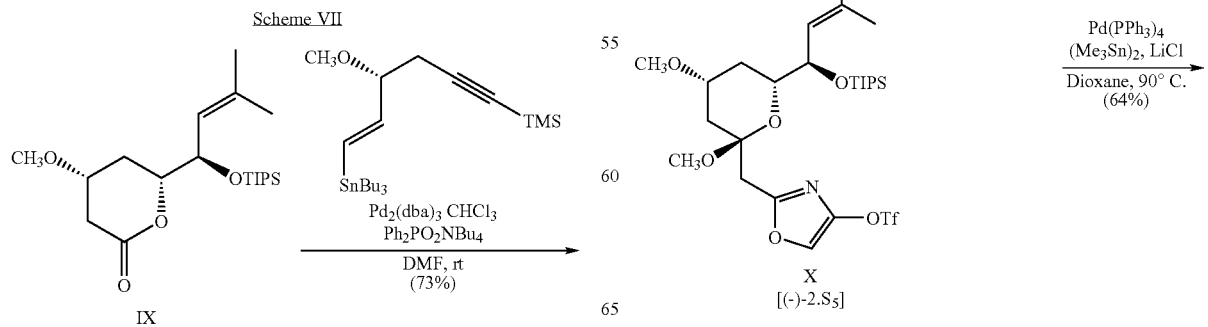

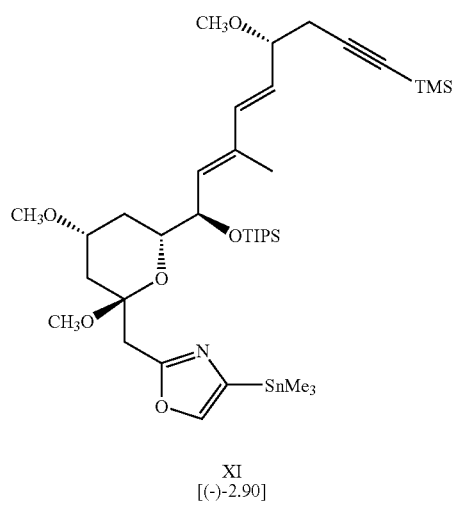
XI
[(−)-2.90]
Analogous to the chemistry used to prepare XI [(−)-2.90], compound IX was reacted with vinyl stannane IXa [3.24] (Scheme IX) to provide an intermediate which upon further transformation yielded XII [(−)-3.20] (Scheme VIII).
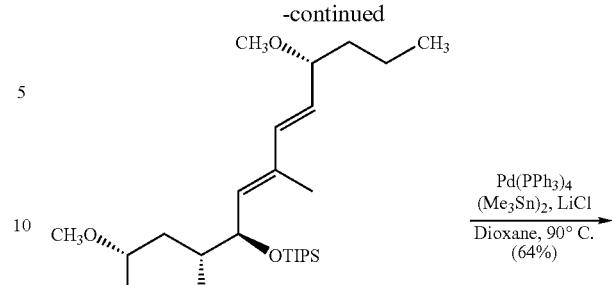
[(−)-3.S3]
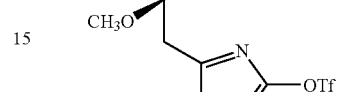
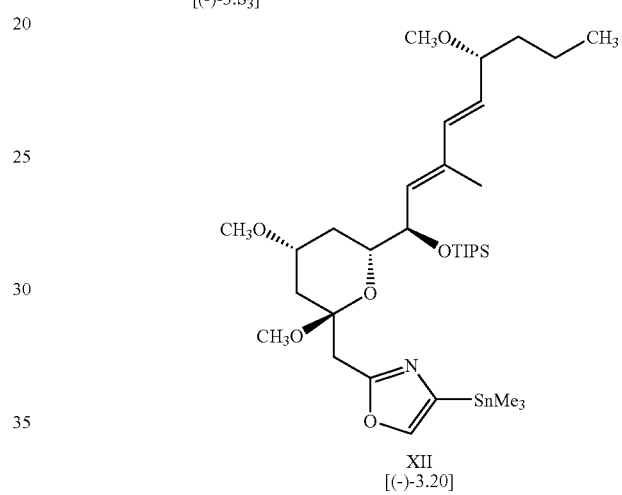
XII
[(−)-3.20]
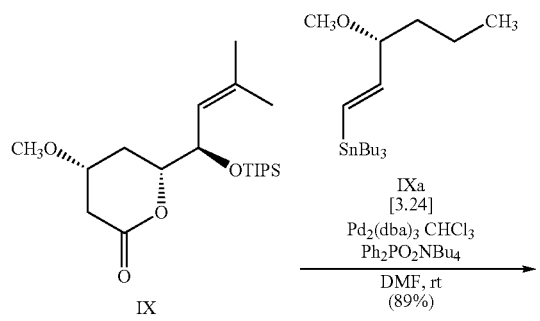
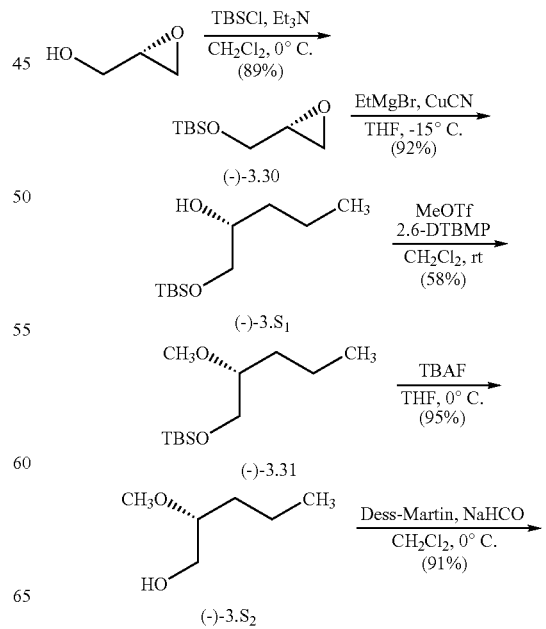

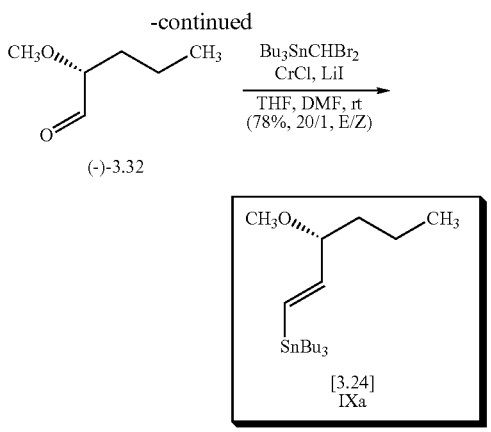

Abreviations
2,6-DTBMP: 2,6-di-tert-butylmethylpyridine
TBAF: tert-butylammonium fluoride Deprotection of the acetylene of X [(−)-2.S₅] (from Scheme VII) with silver nitrate to XIII [(−)-3.28] followed by partial hydrogenation gave an intermediate triflate which was stannylated with hexamethylditin in the presence of a palladium catalyst to give XIV [(−)-3.19] (Scheme X). In the partial hydrogenation step, 1-hexene was used as a hydrogen scavenger to protect against over-reduction of the intermediate triflate

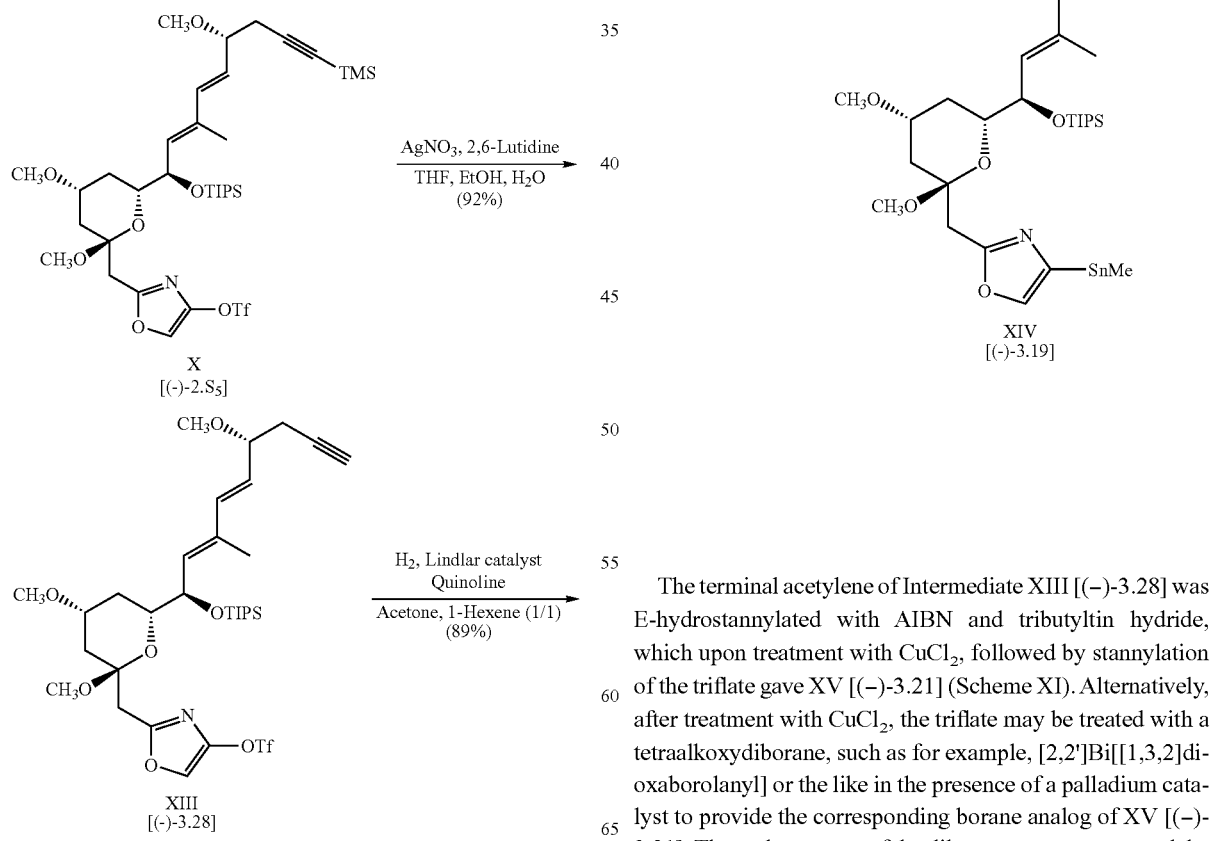

The terminal acetylene of Intermediate XIII [(−)-3.28] was E-hydrostannylated with AIBN and tributyltin hydride, which upon treatment with CuCl₂, followed by stannylation of the triflate gave XV [(−)-3.21] (Scheme XI). Alternatively, after treatment with CuCl₂, the triflate may be treated with a tetraalkoxydiborane, such as for example, [2,2']Bi[[1,3,2]dioxaborolanyl] or the like in the presence of a palladium catalyst to provide the corresponding borane analog of XV [(−)-3.21]. The carbon atoms of the diborane reagent may each be substituted with an alkyl or aryl substituent.

Scheme XI
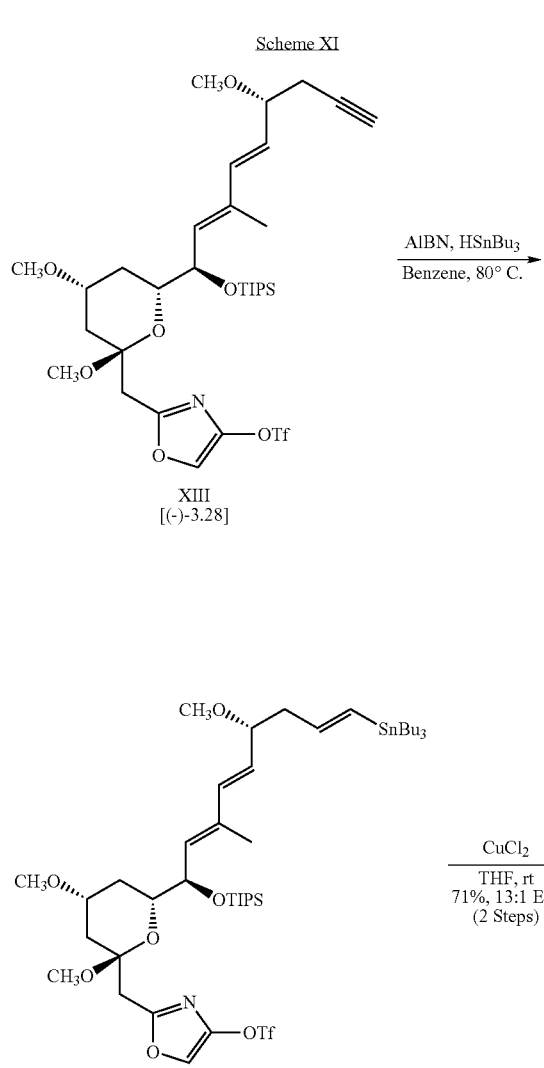
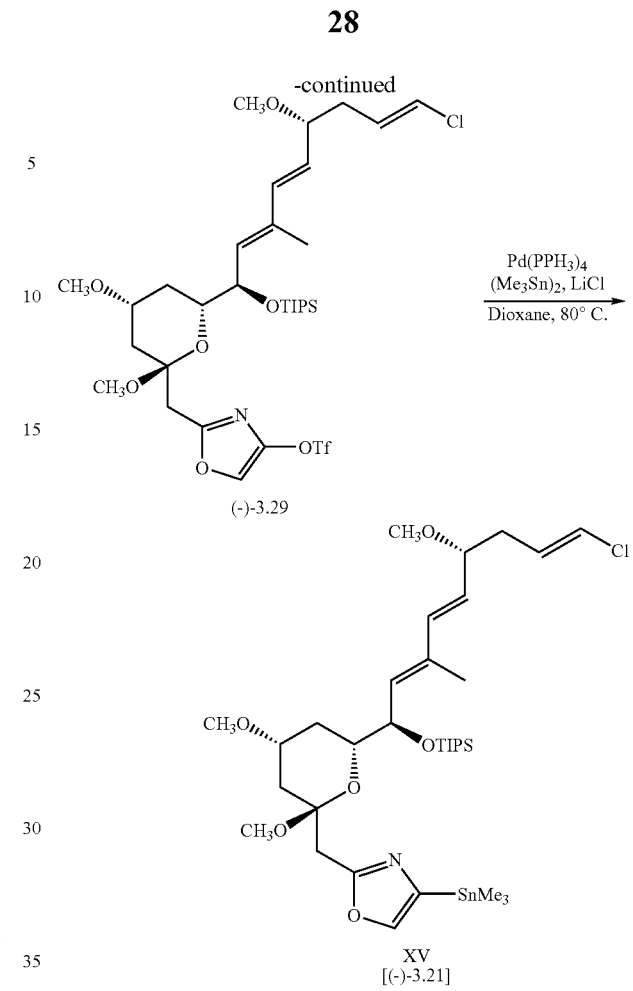
Stille coupling of VIII [(+)-2.5Z or (+)-2.5E] with XI [(−)-2.90], XII [(−)-3.20], XIV [(−)-3.19], or XV [(−)-3.21] or a borane analog thereof using a palladium catalyst, triphenylarsine, diphenylphosphonate salt and diisopropylethylamine in DMF gave the corresponding XVIa, [(+)-3.35 and (+)-3.39] XVIb [(+)-3.37], XVIc [(+)-3.36], XVId [(+)-3.38] or XVIe [(+)-3.40], respectively (Scheme XII).
SCHEME XII
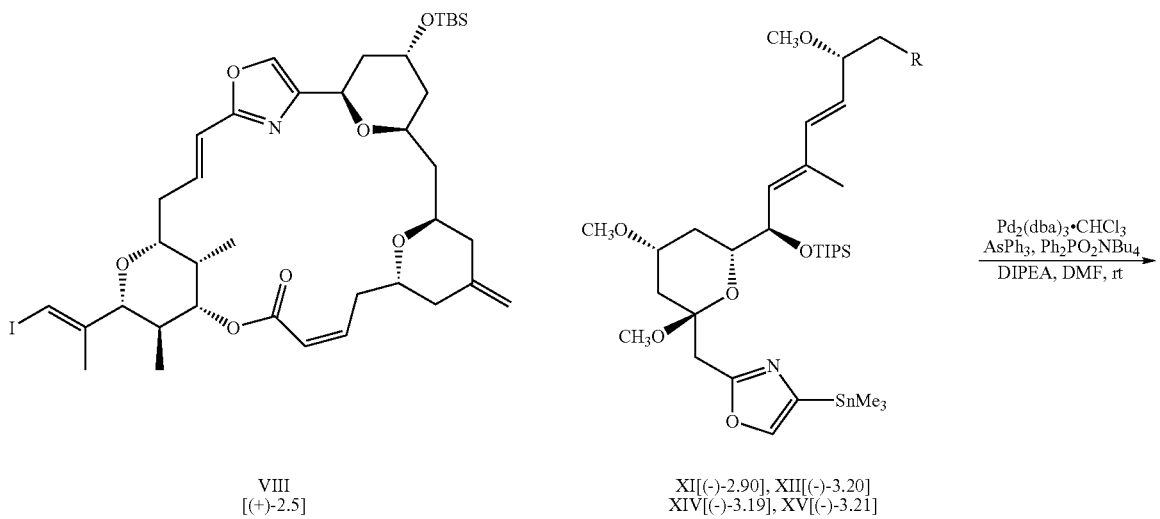

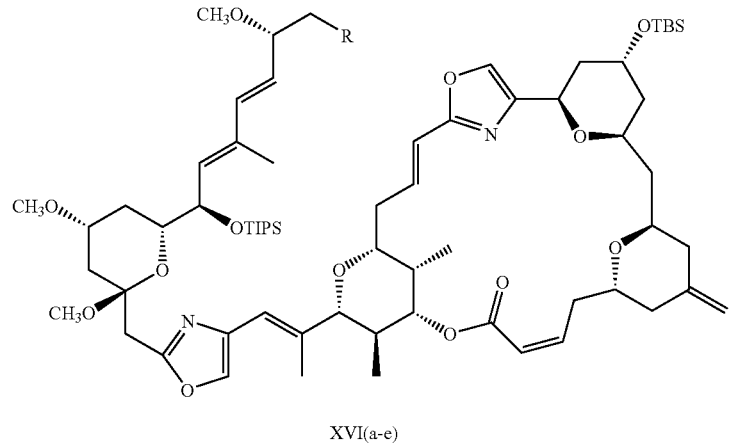

XVI(a-e)

| | C45–C46 Sidechain R= | Yield |
|---|---|---|
| a) | ⌇–C≡C–TMS | (+)-3.35 Z-Macrocycle: 68%<br>(+)-3.39 E-Macrocycle: 66% |
| b) | ⌇–CH(CH₃)–CH₂CH₃ type (ethyl branch) | (+)-3.37 Z-Macrocycle: 82% |
| c) | ⌇–CH=CH₂ (vinyl) | (+)-3.36 Z-Macrocycle: 77% |
| e) | | (+)-3.40 Central Pyran: 69% |
| d) | ⌇–CH=CH–Cl | (+)-3.38 Z-Macrocycle 87% |

Final elaboration of (+)-Phorboxazole A was carried by reacting XVIa [(+)-3.35] with silver nitrate to provide the bromo acetylene (+)-2.92. A palladium mediated hydrostannylation with tributyltin hydride, followed by treatment of the stannane with N-bromosuccinimide, subsequent desilylation of the secondary alcohols and deprotection of the lactol with aqueous hydrochloric acid to give the desired (+)-Phorboxazole A XVIII [(+)-1] (Scheme XIII).

Scheme XIII

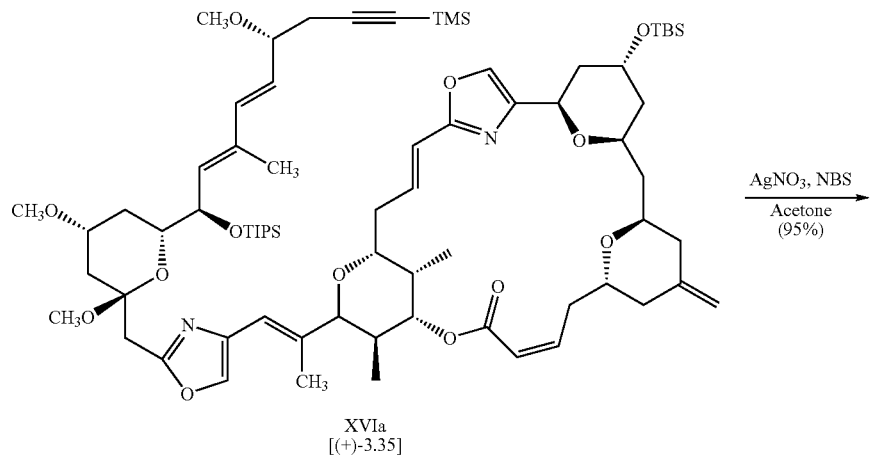

XVIa
[(+)-3.35]

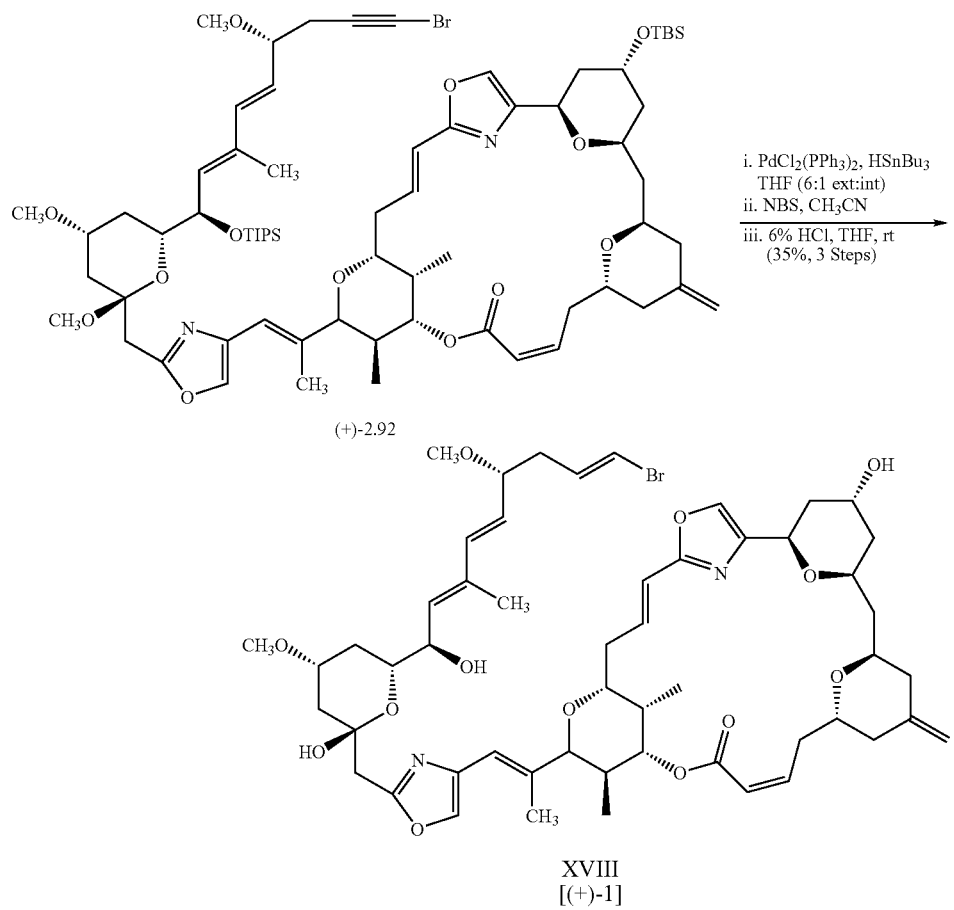

(+)-2.92

XVIII
[(+)-1]

The secondary alcohols in analogs XVI(a-e) were desilylated using tetrabutylammonium fluoride in THF. Deprotection of the of the lactol with aqueous hydrochloric acid gave the desired products XVII(a-e). The central pyran XVIIe [(−)-3.41] noted in Scheme XIV and below was prepared by coupling IV [(+)-2.44] with XIV [(−)-3.19] using conditions generally described in Scheme XII.

SCHEME XIV

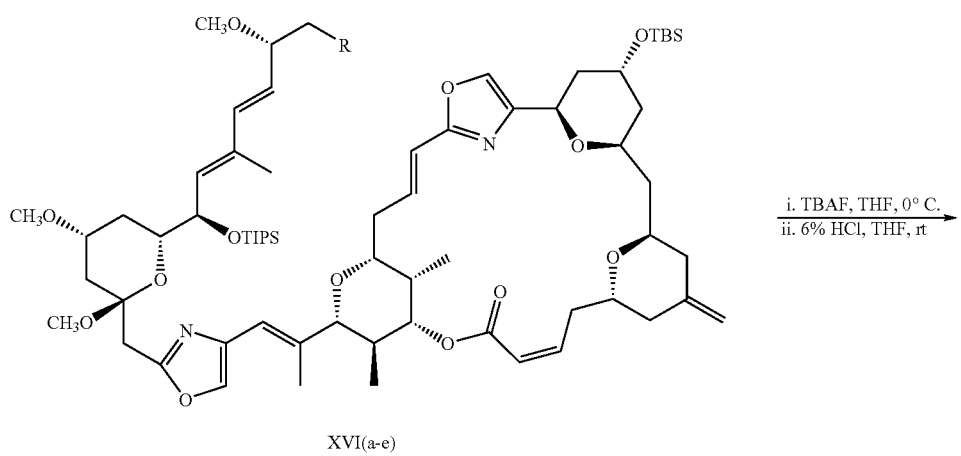

XVI(a-e)

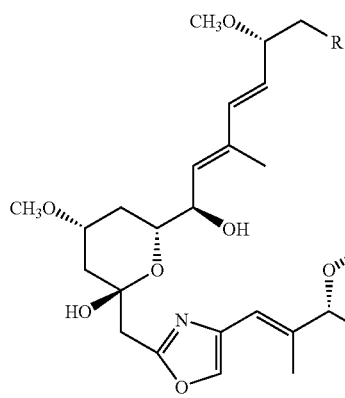
XVII(a-e)
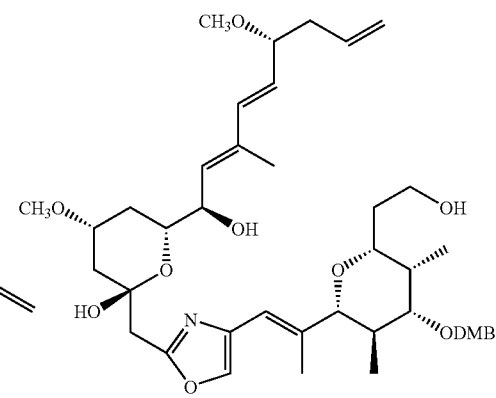
Central Pyran
XVIIe[(−)-3.41]
| | C45–C46 Sidechain R= | Yield |
|---|---|---|
| a) | ≡—CH₃ (propynyl) | Z-Macrocycle: 64% XVIIaZ [(+)−3.11]<br>E-Macrocycle: 69% XVIIaE [(+)−3.15] |
| b) | —CH₂CH₃ | Z-Macrocycle: 86% XVIIb [(−)-3.13] |
| c) | —CH=CH₂ | Z-Macrocycle: 67% XVIIc [(+)-3.12] |
| a) | | Central Pyran: 66% XVIIe [(−)-3.41] |
| d) | —CH=CH—Cl | Z-Macrocycle: 61% XVIId [(+)-3.14] |
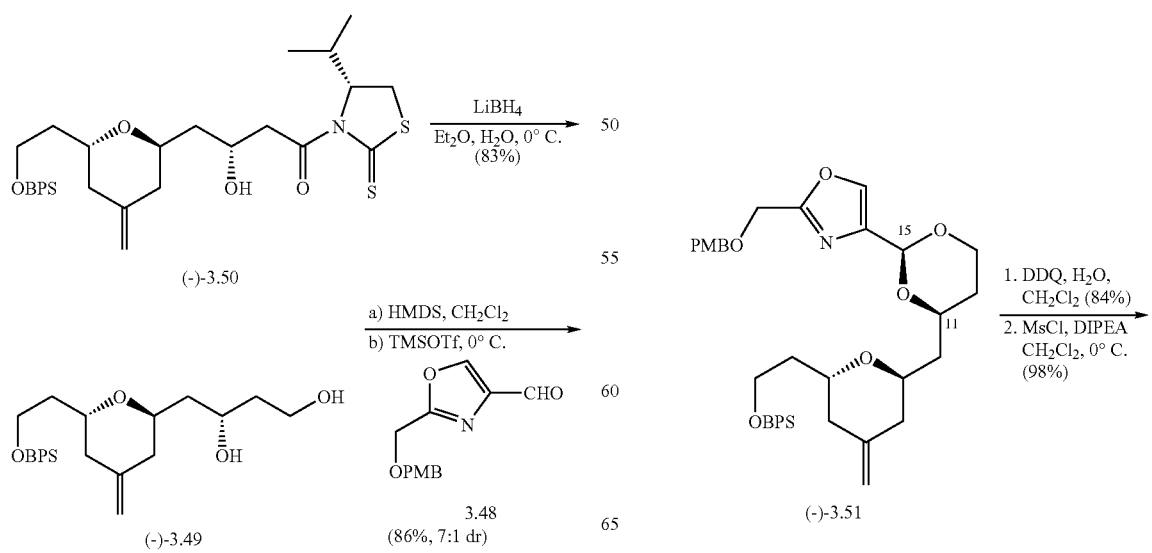
Scheme XV

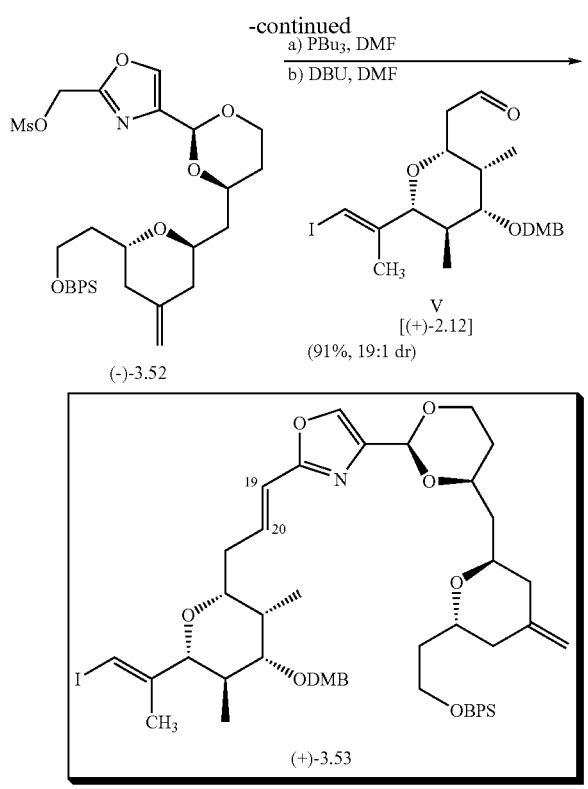

The synthesis of E and Z macrocycles (3.43Z and 3.43E) began with construction of the Wittig salt of 3.52 (Scheme XV). β-Hydroxy thioimide (−)-3.50, prepared by treatment of I (see Scheme II) with 1-(4-Isopropyl-2-thioxo-thiazolidin-3-yl)-ethanone in the presence of tin(II) triflate and ethyl piperidine (see Nagao, et al., *J. Chem. Soc. Com.* 1985, 1418, and Smith, et al, *Org. Lett.* 1999, 1, 909) was reduced to diol (−)-3.49 employing lithium borohydride (LiBH$_4$). Under Noyori condensation conditions, treatment of diol (−)-3.49 with HMDS afforded the corresponding bis-silylated diol (Noyori, R. et al., *Tetrahedron,* 1981, 37, 3899). When condensed with oxazole aldehyde 3.48, promoted by TMSOTf, acetal (−)-3.51 was produced as a mixture in 86% yield (ca. 7:1, cis:trans). After separation, exposure of (−)-3.51 to wet DDQ gave rise to the primary alcohol that, when treated with MsCl and DIPEA, afforded mesylate (−)-3.52 in 82% yield over the two steps. Construction of the C(19-20) E-olefin next called upon the productive one-flask Wittig salt formation/olefination protocol of Evans, et al. (*J. Am. Chem. Soc.* 2000, 122, 10033). To this end, treatment of mesylate (−)-3.52 with PBu$_3$, followed by aldehyde V [(+)-2.12] and DBU furnished tetracycle (+)-3.53 in 91% yield with excellent configurational control (ca. 19:1, E:Z).

Completion of both the E and Z-macrocycles (3.43Z and 3.43E) continued with removal of the BPS protecting group with TBAF, followed by oxidation of the resultant primary alcohol with the Dess-Martin periodinane to furnish aldehyde (+)-3.54 in good yield. Exposure to DDQ promoted the removal of the 3,4-dimethoxybenzyl (DMB) protecting group to furnish aldehyde-alcohol (+)-3.44 in an excellent 98% yield (Scheme XVI). While problematic in the

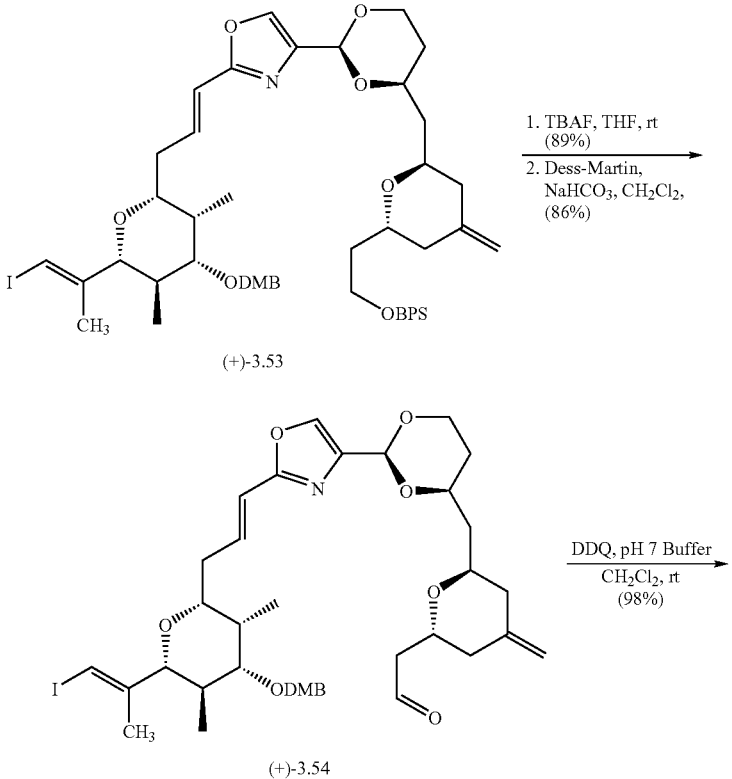

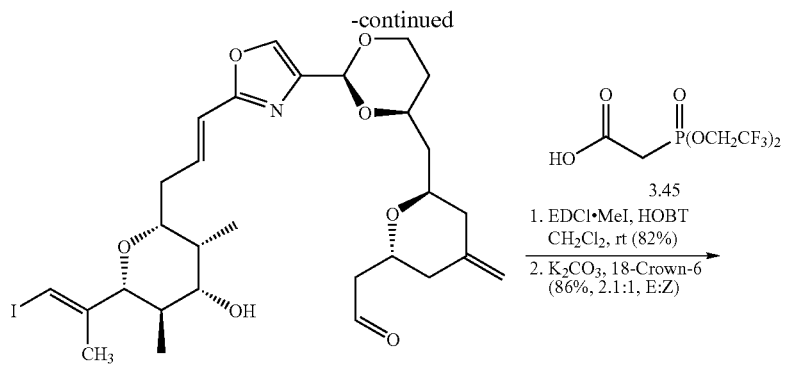

(+)-3.44 second generation synthesis of (+)-phorboxazole A, application of the Still modified Horner-Emmons olefination, Still, et al. (*Tetrahedron Lett.* 1983, 24, 4405), in the C(11-15) acetal series would advantageously provide access to both the Z and E-C(2-3) macrocycles. To this end, EDCl.MeI/HOBT promoted union of aldehyde-alcohol (+)-3.44 with phosphonate acid 3.45 gave rise to the corresponding phosphonate ester in 82% yield. Treatment with $K_2CO_3$ and 18-crown-6 promoted the intramolecular Still-Gennari olefination to provide Z and E-macrocycles (+)-3.43Z and (+)-3.43E respectively, in 88% combined yield, as a readily separable mixture (ca. 2.1:1, Z:E, only Z-isomer shown).

Addition of the Grignard reagent derived from oxazole 2.9 to dienyl lactone (−)-2.80 (derived from vinyl iodide IX in Scheme VII) gave rise to the C(33) hemiacetal (Scheme XVII). Immediate treatment with triethylsilyl trifluoromethanesulfonate (TESOTf) and 2,6-lutidine provided the C(33) TES protected hemiacetal (−)-3.56 in modest yield. Employing $Pd(PPh_3)_4$ and $(Me_3Sn)_2$, conversion to the fully elaborated trimethylstannane (−)-3.57 proceeded in 55% yield. This yield is significantly lower than observed in our (+)-phorboxazole A and C(45-46) analogue syntheses, presumably due to decomposition of the TES hemiacetal under the harsh reaction conditions.

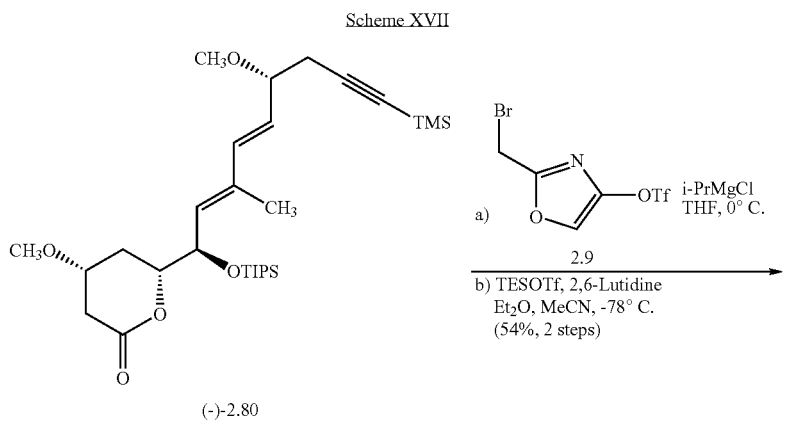

Scheme XVII

-continued

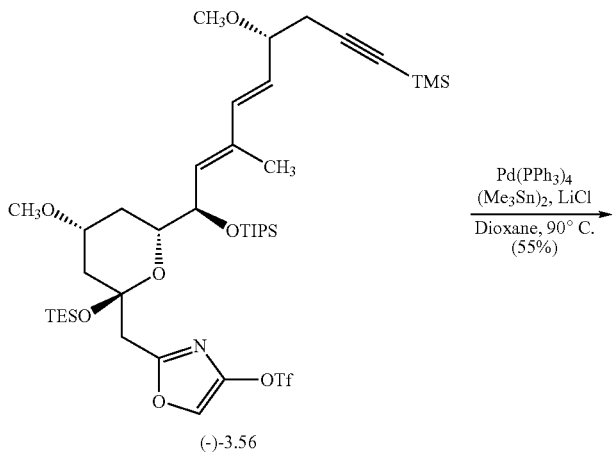

(-)-3.56

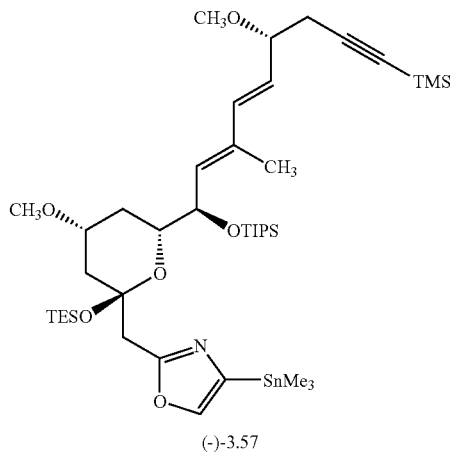

(-)-3.57

Continuing with the syntheses of 3.42Z and 3.42E, union of Z and E-acetal macrocycles (+)-3.43Z and (+)-3.43E with oxazole stannane (−)-3.57 under the phorboxazole Stille coupling protocol smoothly furnished the corresponding Z and E-coupled products (Scheme XVIII). Final treatment with 4 equivalents of TBAF promoted global removal of the C(46) TMS, C(38) TIPS and C(33) TES protecting groups to furnish C(11-15) acetal analogues XVIIfZ [(+)-3.42Z] and XVIIfE [(+)-3.42E] in 54% and 49% yield respectively (only Z-isomer shown, Smith, A. B., et al., (*Org. Lett.* 2006, 8, 797).

Scheme XVIII

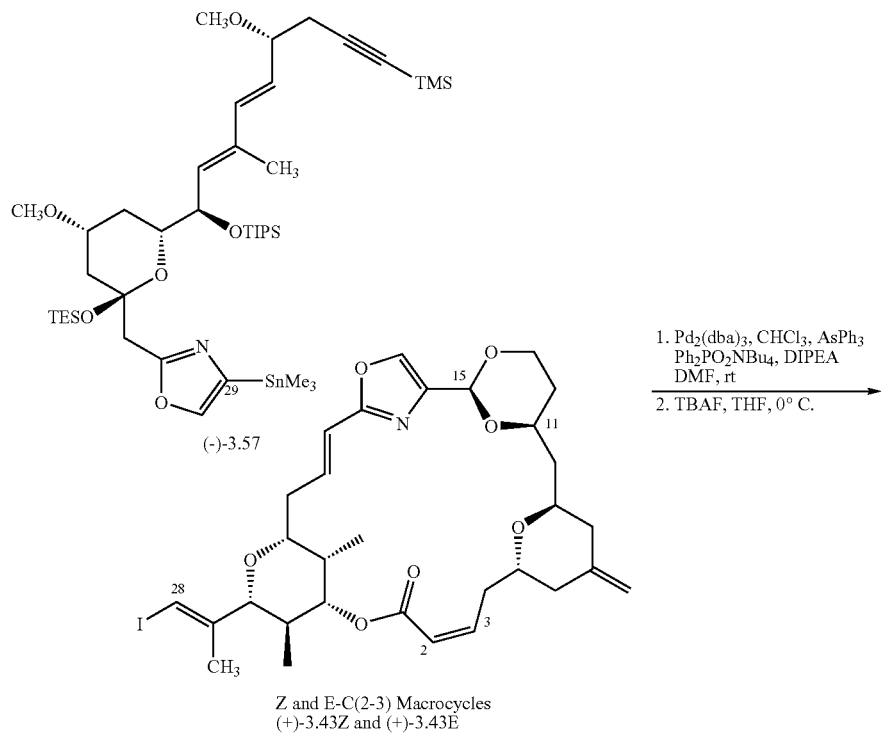

Z and E-C(2-3) Macrocycles
(+)-3.43Z and (+)-3.43E

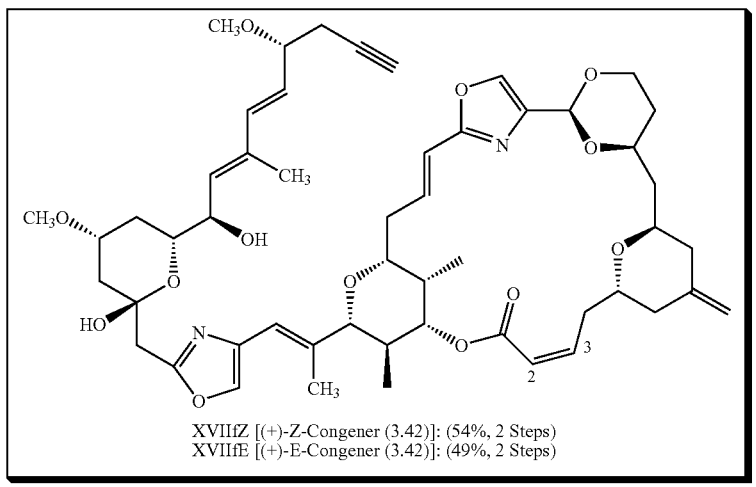

XVIIfZ [(+)-Z-Congener (3.42)]: (54%, 2 Steps)
XVIIfE [(+)-E-Congener (3.42)]: (49%, 2 Steps)

Experimental Procedures

Unless otherwise noted, all solvents were reagent grade. Diethyl ether ($Et_2O$) and tetrahydrofuran (THF) were freshly distilled from sodium/benzophenone under argon. N-Butyllithium and t-butyllithium were purchased from Aldrich. Reactions were magnetically stirred and monitored by thin layer chromatography (TLC) with 0.25 mm E. Merck pre-coated silica gel plates. Flash chromatography was performed with silica gel 60 (particle size 0.040-0.062 mm) supplied by Silicycle and Sorbent Technologies. Yields refer to chromatographically and spectroscopically pure compounds, unless otherwise stated. Infrared spectra were recorded on a JASCO Model FT/IR-480 Plus spectrometer. Proton and carbon-13 NMR spectra were recorded on a BRUKER AMX-500 spectrometer. Chemical shifts are reported relative to either chloroform (d 7.26) or benzene (d 7.15) for $^1$H-NMR and either chloroform (d 77.0) or benzene (d 128.0) for $^{13}$C NMR. Optical rotations were measured on a PERKIN-ELMER model 241 polarimeter. High resolution mass spectra were measured at the University of Pennsylvania Mass. Spectrometry Service Center.

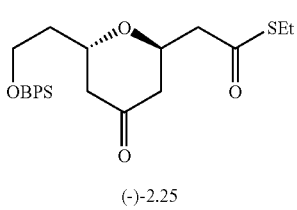

(−)-2.25 trans-Tetrahydropyranone Thiolester (−)-2.25:

To a solution of known enone (−)-2.23 (Smith, et al. *J. Am. Chem. Soc.* 2001, 123, 10942) (6.93 g, 18.2 mmol) and scandium triflate [Sc(OTf)$_3$] (89.3 mg, 0.182 mmol) in dichloromethane (91.2 mL) under argon was added dropwise, the TMS-enol ether derived from ethylthioacetate (4.83 g, 27.4 mmol) at −78° C. The reaction mixture was stirred for 15 minutes at −78° C. and then quenched via dropwise addition of methanol/pyridine (1:1, 100 mL) and warmed to room temperature. After one hour and thirty minutes the layers of the biphasic mixture were separated and the aqueous layer was extracted with dichloromethane (70 mL, 3×). The combined organic layers were dried over Na$_2$SO$_4$, filtered and concentrated under reduced pressure. Purification via silica gel chromatography (10% EtOAc/hexanes) afforded trans-tetrahydropyranone thiolester (−)-2.25 (8.39 g, 95%) as a light yellow oil: $[\alpha]_D^{20}$−9.1 (c 2.3, CHCl$_3$); IR (CHCl$_3$) 2931 (m), 2857 (m), 1719 (s), 1685 (s), 1472 (w), 1428 (m), 1112 (s), 998 (w), 823 (w), 739 (m), 614 (m) cm$^{-1}$; $^1$HNMR (500 MHz, CDCl$_3$) δ 7.65 (m, 4H), 7.38 (m, 6H), 4.50 (m, 1H), 4.41 (ddd, J=8.6, 5.7, 5.5 Hz, 1H), 3.79 (ddd, J=10.5, 7.8, 5.4 Hz, 1H), 3.71 (m, 1H), 2.84 (m, 3H), 2.65 (dd, J=14.9, 5.8 Hz, 1H), 2.58 (ddd, J=14.5, 5.3, 1.1 Hz, 1H), 2.53 (ddd, J=14.5, 4.7, 1.3 Hz, 1H), 2.33 (ddd, J=14.7, 7.6, 1.1 Hz, 1H), 2.30 (dd, J=14.5, 6.2, 1.3 Hz, 1H), 1.89 (m, 1H), 1.68 (m, 1H), 1.20 (app t, J=7.4 Hz, 3H), 1.05 (s, 9H); $^{13}$CNMR (125 MHz, CDCl$_3$) δ 206.2, 195.7, 135.5, 133.7, 133.6, 129.6, 129.5, 127.7, 70.0, 68.7, 59.9, 48.7, 46.5, 46.2, 36.7, 26.9, 23.5, 19.2, 14.5; high resolution mass spectrum (ES$^+$) m/z 507.2024 [(M+Na)$^+$; calcd. for C$_{27}$H$_{36}$O$_4$SSiNa: 507.2001].

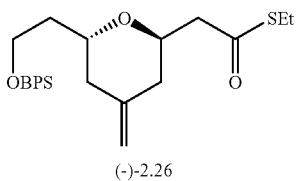

(−)-2.26 trans-Tetrahydropyran exo-Olefin (−)-2.26:

To a solution of thiolester (−)-2.25 (8.39 g, 17.3 mmol) and ethyl pivalate (0.503 mL, 3.11 mmol) in THF (14.7 mL) under argon at room temperature was added dimethyltitanocene (0.5 M/THF) (62.3 mL, 31.1 mmol) followed by heating to 55° C. with the exclusion of light. After twenty hours, the reaction mixture was cooled to room temperature, diluted with hexanes (6 mL) and filtered through a pad of Celite. The resultant filtrate was then concentrated under reduced pressure. The crude product was dissolved in chloroform (15 mL), washed with 1N hydrogen chloride solution (15 mL, 1×), dried over Na$_2$SO$_4$, filtered and concentrated under reduced pressure. Purification via silica gel chromatography (2.5% EtOAc/hexanes) afforded trans-tetrahydropyran exo-olefin (−)-2.26 (6.35 g, 79%) as a light yellow oil: $[\alpha]_D^{20}$−21.2 (c 1.1, CHCl$_3$); IR (CHCl$_3$) 3071 (m), 2931 (s), 1689 (s), 1685 (s), 1473 (w), 1428 (s), 1265 (w), 1112 (s), 998 (m), 894 (w), 823 (w), 739 (m), 702 (s) cm$^-$; $^1$HNMR (500 MHz, CDCl$_3$) δ 7.66 (m, 4H), 7.40 (m, 6H), 4.79 (s, 2H), 4.24 (m, 1H), 4.01 (m, 1H), 3.75 (m, 1H), 3.72 (m, 1H), 2.82 (m, 2H), 2.80 (dd, J=14.5, 7.2 Hz, 1H), 2.65 (dd, J=14.5, 6.4 Hz, 1H), 2.36 (m, 2H), 2.05 (dd, J=13.2, 6.1 Hz, 1H), 1.99 (dd, J=13.2, 6.5 Hz, 1H), 1.88 (m, 1H), 1.65 (m, 1H), 1.20 (app t, J=7.4 Hz, 3H), 1.05 (s, 9H); $^{13}$CNMR (125 MHz, CDCl$_3$) δ 196.8, 141.3, 135.5, 134.0, 133.9, 129.5, 129.4, 127.6, 111.0, 69.7, 69.3, 60.6, 47.8, 39.5, 39.1, 36.3, 26.9, 23.3, 19.2, 14.6; high resolution mass spectrum (ES$^+$) m/z 505.2229 [(M+Na)$^+$; calcd for C$_{28}$H$_{38}$O$_3$SSiNa: 505.2209].

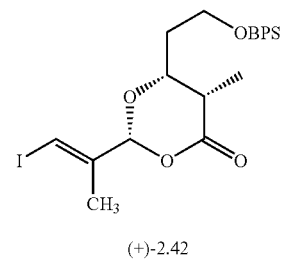

(+)-2.42

Dioxanone (+)-2.42:

Under argon, a solution of known β-hydroxy acid (+)-2.21 (Smith, et al. *Org. Lett.* 1999, 1, 913) (14.5 g, 37.6 mmol) in dichloromethane (114 mL) was treated with 1,1,1,3,3,3-hexamethyldisilazane (8.72 mL) at room temperature. After stirring twenty-four hours, the reaction was concentrated under reduced pressure followed by drying under vacuum (to remove excess 1,1,1,3,3,3-hexamethyldisilazane) to provide the corresponding bis-silylated β-hydroxy acid that was used without any further purification. Under argon, a solution of the bis-silylated β-hydroxy acid, 2,6-di-tert-butyl-4-methylpyridine (2,6-DTBMP) (386 mg, 1.88 mmol) and known freshly prepared E-C(2-3)-iodomethacrolein 2.20 (Ahmed, et al. *Tetrahedron Lett.* 1998, 39, 183) (9.94 g, 50.7 mmol) in dichloromethane (150 mL) at −78° C. was treated with trimethylsilyltrifluoromethylsulfonate (TMSOTf) (1.50 mL, 8.26 mmol). After 30 min, trifluoromethanesulfonic acid (TfOH) (300 mL, 3.38 mmol) was added dropwise and the reaction mixture stirred at −78° C. After two hours, the reaction was quenched via dropwise addition of pyridine (1.16 mL), warmed to room temperature and concentrated under reduced pressure. Purification via silylated silica gel chromatography (50% EtOAc/hexanes) afforded dioxanone (+)-2.42 (19.7 g, 93%, 20:1 dr) as a light yellow oil: $[\alpha]_D^{20}$+5.7 (c 1.4, CHCl$_3$); IR (CHCl$_3$) 2931 (m), 2857 (m), 1700 (s), 1472 (w), 1428 (m), 1112 (s), 822 (w) cm$^{-1}$; $^1$HNMR (500 MHz, CDCl$_3$) δ 7.62 (m, 4H), 7.39 (m, 6H), 6.63 (s, 1H), 5.53 (s, 1H), 4.28 (ddd, J=8.1, 4.3, 4.3 Hz, 1H), 3.78 (m, 2H), 2.70 (ddd, J=16.7, 9.3, 5.3 Hz, 1H), 1.83 (d, J=1.0 Hz, 3H), 1.72 (m, 2H), 1.23 (d, J=7.3 Hz, 3H), 1.04 (s, 9H); $^{13}$CNMR (125 MHz, CDCl$_3$) δ 171.4, 142.5, 135.5, 133.4, 133.3, 129.8, 129.7, 127.8, 102.3, 85.3, 73.4, 59.3, 39.4, 33.9, 26.8, 19.2, 18.7, 12.1; high resolution mass spectrum (ES$^+$) m/z 587.1093 [(M+Na)$^+$; calcd for C$_{26}$H$_{33}$O$_4$SiNa: 587.1091].

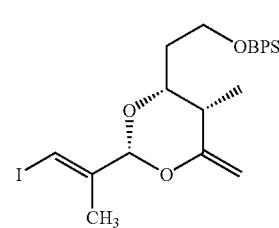

(+)-2.19

Enol Acetal (+)-2.19:

Under argon, a solution of dioxanone (+)-2.42 (7.58 g, 13.4 mmol) was treated with dimethyltitanocene (0.5 M/THF) (80.6 mL, 40.3 mmol), and the resultant solution was stirred at 55° C. in the absence of light. After twenty three hours, the reaction mixture was cooled to room temperature and diluted with hexanes (200 mL). The resultant yellow precipitate was filtered through a pad of Celite, and the filtrate was concentrated under reduced pressure. Flash chromatography on silylated silica gel (7% EtOAc/hexanes) furnished enol acetal (+)-2.19 (5.98 g, 79%) as a colorless oil: $[\alpha]_D^{20}$+29.8 (c 2.3, CHCl$_3$); IR (CHCl$_3$) 2930 (m), 2857 (m), 1653 (w), 1472 (w), 1428 (m), 1289 (w), 1259 (m), 1112 (s), 997 (m), 823 (w), 738 (m), 701 (s) cm$^{-1}$; $^1$HNMR (500 MHz, CDCl$_3$) δ 7.66 (m, 4H), 7.40 (m, 6H), 6.59 (d, J =0.7 Hz, 1H), 4.97 (s, 1H), 4.45 (s, 1H), 4.24 (s, 1H), 4.06 (m, 1H), 3.80 (ddd, J=10.2, 10.2, 4.8 Hz, 1H), 3.74 (ddd, J=10.2, 5.3, 5.0 Hz, 1H), 2.25 (dddd, J=13.9, 7.0, 7.0, 2.5 Hz, 1H), 1.90 (d, J=0.9 Hz, 3H), 1.81 (m, 1H), 1.68 (m, 1H), 1.15 (d, J=7.0 Hz, 3H), 1.06 (s, 9H); $^{13}$CNMR (125 MHz, CDCl$_3$) δ 162.2, 144.3, 135.5, 133.7, 133.6, 129.7, 129.6, 127.7, 102.6, 92.6, 83.6, 75.7, 59.8, 36.9, 34.9, 26.9, 19.2, 19.1, 13.5; high resolution mass spectrum (ES$^+$) m/z 585.1324 [(M+Na)$^+$; calcd for C$_{27}$H$_{35}$O$_3$SiNa: 585.1298].

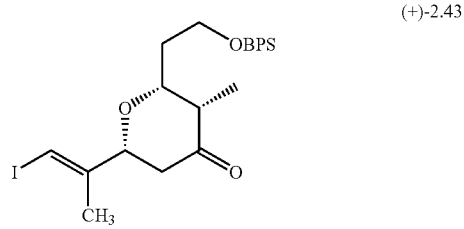

(+)-2.43

Tetrahydropyran (+)-2.43:

Under argon, a solution of enol acetal (+)-2.19 (5.27 g, 9.38 mmol) in dichloromethane (94 mL) was treated dropwise with Me$_2$AlCl (1.0 M/hexane) (11.25 mL, 11.25 mmol) at −78° C. After stirring for five minutes, the reaction mixture was warmed to 0° C. and stirred for three minutes. The reaction was then re-cooled to −78° C. and quenched with triethylamine (4.5 mL), followed by treatment with saturated aqueous sodium bicarbonate (70 mL) and warmed to room temperature with stirring. The resulting mixture was diluted with dichloromethane (150 mL) and 1N hydrogen chloride solution (70 mL) and the layers separated. The aqueous layer was extracted with dichloromethane (200 mL, 2×) and the combined organic extracts were dried over Na$_2$SO$_4$, filtered and concentrated under reduced pressure. Purification via silica gel chromatography (5% EtOAc/hexanes) provided tetrahydropyran (+)-2.43 (5.26 g, 99%) as a colorless oil: $[\alpha]_D^{20}$+66.4 (c 1.2, CHCl$_3$); IR (CHCl$_3$) 2929 (m), 2856 (m), 1719 (s), 1472 (w), 1428 (m), 1112 (s), 822 (w), 738 (m), 702 (s) cm$^{-1}$; $^1$HNMR (500 MHz, CDCl$_3$) δ 7.64 (m, 4H), 7.40 (m, 6H), 6.36 (dd, J=1.1, 1.0 Hz, 1H), 4.00 (dd, J=11.8, 2.4 Hz, 1H), 3.93 (ddd, J=9.1, 3.3, 2.7 Hz, 1H), 3.82 (ddd, J=10.2, 9.1, 4.7 Hz, 1H), 3.75 (ddd, J=10.2, 5.9, 4.4 Hz, 1H), 2.51 (dd, J=14.5, 11.8 Hz, 1H), 2.36 (m, 1H), 2.34 (ddd, J=14.5, 2.9, 1.2 Hz, 1H), 1.88 (m, 1H), 1.83 (d, J=0.9 Hz, 3H), 1.65 (m, 1H), 1.12 (d, J=7.2 Hz, 3H), 1.03 (s, 9H); $^{13}$CNMR (125 MHz, CDCl$_3$) δ 210.4, 146.0, 135.5, 133.7, 133.6, 129.7, 129.6, 127.7, 80.2, 79.2, 75.2, 60.0, 49.0, 42.7, 34.6, 26.8, 20.6, 19.2, 10.9; high resolution mass spectrum (ES$^+$) m/z 585.1291 [(M+Na)$^+$; calcd for C$_{27}$H$_{35}$O$_3$SiNa: 585.1298].

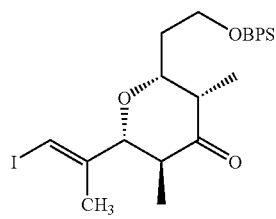

(+)-2.18

Methylated Tetrahydropyranone (+)-2.18:

Under argon, lithium hexamethyldisilazane (LiHMDS) (1.19 M/THF) (9.92 mL, 11.8 mmol) was diluted with THF (9.92 mL) at room temperature and cooled to −78° C. A solution of tetrahydropyranone (+)-2.43 (6.03 g, 10.7 mmol) in THF (53.5 mL) was added dropwise via cannula to the diluted lithium hexamethyldisilazane solution under stirring. After stirring for thirty minutes at −78° C., the solution was warmed to −20° C. and stirred for one hour. A cooled solution (−20° C.) of methyl iodide (2.00 mL, 32.2 mmol) and HMPA (5.60 mL, 32.2 mmol) in THF (21.5 mL) was added dropwise via cannula and the reaction mixture was stirred at −20° C. After two hours, the reaction was quenched with saturated aqueous ammonium chloride (130 mL), warmed to room temperature, stirred for thirty minutes and then extracted with diethyl ether (150 mL, 3×). The combined organic extracts were washed with saturated aqueous ammonium chloride (200 mL) and saturated aqueous sodium chloride (200 mL), dried over Na$_2$SO$_4$, filtered and concentrated under reduced pressure. Purification via silica gel chromatography (2.5% EtOAc/hexanes) furnished methylated tetrahydropyranone (+)-2.18 (4.20 g, 68%; 91% based on recovered starting material), as a colorless oil and starting material (+)-2.43 (1.53 g, 25%); $[\alpha]_D^{20}$+12.6 (c 1.1, CHCl$_3$); IR (CHCl$_3$) 2930 (m), 2857 (m), 1715 (s), 1457 (w), 1428 (m), 1282 (w), 1197 (w), 1112 (s), 822 (w), 738 (m), 701 (s) cm$^{-1}$; $^1$HNMR (500 MHz, CDCl$_3$) δ 7.64 (m, 4H), 7.40 (m, 6H), 6.25 (d, J=0.6 Hz, 1H), 3.93 (ddd, J=8.8, 4.0, 2.4 Hz, 1H), 3.77 (ddd, J=10.0, 10.0, 4.7 Hz, 1H), 3.70 (ddd, J=10.0, 4.9, 4.9 Hz, 1H), 3.66 (d, J=10.5 Hz, 1H), 2.65 (dddd, J=14.4, 10.5, 6.6, 3.9 Hz, 1H), 2.43 (dddd, J=11.8, 7.1, 4.7, 2.4 Hz, 1H), 1.90 (d, J=0.5 Hz, 3H), 1.85 (m, 1H), 1.64 (m, 1H), 1.15 (d, J=7.1 Hz, 3H), 1.04 (s, 9H), 0.86 (d, J=6.6 Hz, 3H); $^{13}$CNMR (125 MHz, CDCl$_3$) δ 211.8, 145.5, 135.5, 133.7, 133.6, 129.6, 129.4, 127.7, 88.0, 81.7, 75.7, 60.0, 49.3, 43.2, 34.6, 26.8, 19.2, 18.8, 11.2, 9.3; high resolution mass spectrum (ES$^+$) m/z 599.1467 [(M+Na)$^+$; calcd for C$_{28}$H$_{37}$O$_3$SiNa: 599.1454].

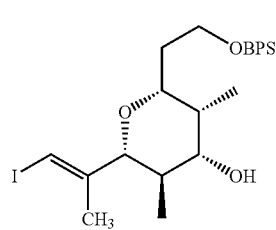

(+)-2.S$_1$

Secondary Alcohol (+)-2.S$_1$:

To a solution of methylated tetrahydropyranone (+)-2.18 (5.88 g, 10.2 mmol) in ethanol (51 mL) at −10° C. under argon was added sodium borohydride (772 mg, 20.4 mmol) in one portion. After stirring for thirty minutes, the reaction mixture was treated with saturated aqueous ammonium chloride (80 mL) followed by dilution with chloroform (100 mL). The resulting layers were separated, and the aqueous layer was extracted with chloroform (100 mL, 2×). The combined organic extracts were dried over Na$_2$SO$_4$, filtered and concentrated under reduced pressure. Purification via silica gel chromatography (10% EtOAc/hexanes→20% EtOAc/hexanes) afforded secondary alcohol (+)-2.S$_1$ (4.80 g, 81%, 6.8:1 dr) as a colorless oil and the secondary alcohol epimer (−)-2.S$_2$ (0.68 g, 12%). (+)-2.S$_1$: $[\alpha]_D^{20}$+15.9 (c 1.2, CHCl$_3$); IR (CHCl$_3$) 3446 (b), 2959 (m), 2929 (m), 2857 (m), 1471 (w), 1428 (m), 1389 (w), 1279 (w), 1112 (s), 1088 (s), 1053 (m), 822 (w), 737 (m), 701 (s) cm$^{-1}$; $^1$HNMR (500 MHz, CDCl$_3$) δ 7.65 (m, 4H), 7.40 (m, 6H), 6.19 (d, J=0.6 Hz, 1H), 3.77 (ddd, J=10.1, 8.3, 5.0 Hz, 1H), 3.69 (ddd, J=10.1, 5.5, 5.0 Hz, 1H), 3.67 (m, 1H), 3.44 (d, J=10.3 Hz, 1H), 3.43 (d, J=10.1 Hz, 1H), 1.82 (m, 2H), 1.81 (d, J=1.0 Hz, 3H), 1.64 (m, 2H), 1.05 (s, 9H), 0.90 (d, J=6.9 Hz, 3H), 0.81 (d, J=6.5 Hz, 3H); $^{13}$CNMR (125 MHz, CDCl$_3$) δ 146.5, 135.5, 133.9, 133.8, 129.7, 129.6, 127.6, 87.2, 80.6, 76.7, 75.0, 60.4, 38.4, 35.5, 34.7, 26.9, 19.3, 19.2, 13.2, 5.7; high resolution mass spectrum (ES$^+$) m/z 601.1626 [(M+Na)$^+$; calcd for C$_{28}$H$_{39}$O$_3$SiINa: 601.1611].

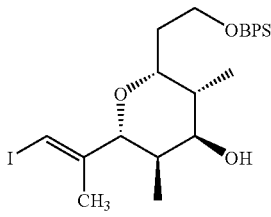

(−)-2.S$_2$ (−)-2.S$_2$; a light yellow oil; $[\alpha]_D^{20}$−2.4 (c 1.8, CHCl$_3$); IR (CHCl$_3$) 3474 (b), 3070 (w), 2960 (s), 2930 (s), 2857 (s), 1617 (w), 1589 (w), 1473 (m), 1428 (s), 1390 (m), 1278 (m), 1112 (s), 982 (m), 823 (m), 738 (m), 701 (s) cm$^{-1}$; $^1$HNMR (500 MHz, CDCl$_3$) δ 7.67 (m, 4H), 7.38 (m, 6H), 6.19 (d, J=0.7 Hz, 1H), 4.12 (m, 1H), 3.94 (d, J=10.6 Hz, 1H), 3.73 (m, 3H), 1.81 (d, J=1.0 Hz, 3H), 1.80 (m, 2H), 1.62 (m, 2H), 1.46 (br s, 1H), 1.06 (s, 9H), 0.93 (d, J=7.1 Hz, 3H), 0.76 (d, J=7.0 Hz, 3H); $^{13}$CNMR (125 MHz, CDCl$_3$) δ 147.1, 135.6, 134.0, 133.9, 129.5, 129.4, 127.6, 82.8, 80.2, 75.0, 70.0, 60.7, 39.3, 35.4, 32.0, 26.9, 19.3, 19.2, 13.3, 10.9; high resolution mass spectrum (ES$^+$) m/z 601.1617 [(M+Na)$^+$; calcd for C$_{28}$H$_{39}$O$_3$SiINa: 601.1611].

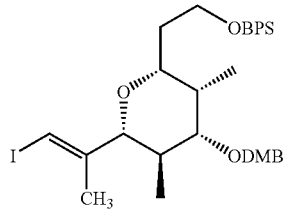

(+)-2.44

DMB Ether (+)-2.44:

To a solution of the alcohol (+)-2.S$_1$ (3.04 g, 5.26 mmol) in THF (52 mL) at 0° C. under argon was added 18-crown-6 (316 mL, 1.58 mmol), 35% potassium hydride (1.21 g, 10.5 mmol) and 3,4-dimethoxybenzyl chloride (1.47 g, 7.89 mmol) followed by warming to 65° C. After ten minutes, the reaction mixture was cooled to 0° C. and quenched with saturated aqueous ammonium chloride (70 mL). The resultant mixture was extracted with chloroform (100 mL, 3×) and the combined organic extracts were dried over Na$_2$SO$_4$, filtered and concentrated under reduced pressure. Purification via silica gel chromatography (50% CHCl$_3$/hexanes→100% CHCl$_3$) afforded a mixture of the desired DMB ether (+)-2.44 and 3,4-dimethoxybenzyl alcohol. A second silica gel flash chromatography (10% EtOAc/hexanes) provided pure DMB ether (+)-2.44 (3.52 g, 92%) as a colorless oil. $[\alpha]_D^{20}$+29.8 (c 1.8, CHCl$_3$); IR (CHCl$_3$) 2930 (m), 2856 (m), 1516 (s), 1463 (m), 1389 (w), 1266 (s), 1238 (m), 1156 (m), 1112 (s), 1030 (s), 822 (w), 738 (m), 702 (s) cm$^{-1}$; $^1$HNMR (500 MHz, CDCl$_3$) δ 7.66 (m, 4H), 7.40 (m, 6H), 6.87 (m, 3H), 6.17 (d, J=1.1 Hz, 1H), 4.57 (d, J=11.2 Hz, 1H), 4.30 (d, J=11.2 Hz, 1H), 3.88 (s, 3H), 3.87 (s, 3H), 3.78 (ddd, J=10.2, 8.6, 4.9 Hz, 1H), 3.72 (ddd, J=10.6, 10.2, 5.4 Hz, 1H), 3.63 (ddd, J=8.2, 4.8, 1.9 Hz, 1H), 3.43 (d, J=10.3 Hz, 1H), 3.17 (dd, J=10.4, 4.7 Hz, 1H), 2.08 (m, 1H), 1.83 (m, 1H), 1.80 (d, J=1.0 Hz, 3H), 1.77 (m, 1H), 1.68 (m, 1H), 1.06 (s, 9H), 0.93 (d, J=6.9 Hz, 3H), 0.80 (d, J=6.5 Hz, 3H); $^{13}$CNMR (125 MHz, CDCl$_3$) δ 149.0, 148.6, 146.7, 135.6, 133.9, 133.8, 131.1, 129.6, 129.4, 127.6, 120.2, 111.2, 110.9, 87.5, 83.2, 80.5, 74.9, 69.8, 60.6, 55.9, 55.8, 35.7, 34.2, 33.4, 26.9, 19.2, 19.1, 13.6, 6.0; high resolution mass spectrum (ES$^+$) m/z 751.2320 [(M+Na)$^+$; calcd for C$_{37}$H$_{49}$O$_5$SiINa: 751.2292].

(+)-2.S$_3$

Primary Alcohol (+)-2.S$_3$:

To a solution of BPS-protected tetrahydropyran (+)-2.44 (155.0 mg, 0.213 mmol) in THF (2.1 mL) under argon was added tetrabutylammonium fluoride (1.0 M/THF) (426 mL, 0.426 mmol) at room temperature. After stirring for one hour, the reaction mixture was treated with saturated aqueous sodium chloride (5 mL) and the solution was extracted with chloroform (10 mL, 3×). The combined organic extracts were dried over Na$_2$SO$_4$, filtered and concentrated under reduced pressure. Purification via silica gel chromatography (33% EtOAc/hexanes) afforded primary alcohol (+)-2.S$_3$ (101.4 mg, 97%) as a colorless oil. $[\alpha]_D^{20}$+51.4 (c 0.8, CHCl$_3$); IR (CHCl$_3$) 3452 (b), 2934 (m), 2879 (m), 1594 (w), 1516 (s), 1464 (m), 1419 (m), 1387 (m), 1265 (s), 1238 (s), 1156 (s), 1139 (s), 1093 (m), 1028 (s), 807 (w), 766 (w) cm$^{-1}$; $^1$HNMR (500 MHz, CDCl$_3$) δ 6.86 (m, 3H), 6.24 (d, J=0.9 Hz, 1H), 4.57 (d, J=11.3 Hz, 1H), 4.31 (d, J=11.3 Hz, 1H), 3.88 (s, 3H), 3.87 (s, 3H), 3.76 (m, 2H), 3.62 (ddd, J=9.8, 2.5, 2.3 Hz, 1H), 3.55 (d, J=10.3 Hz, 1H), 3.18 (dd, J=10.4, 4.7 Hz, 1H), 2.31 (br s, 1H), 2.04 (m, 1H), 1.97 (m, 1H), 1.80 (d, J=1.0 Hz, 3H), 1.79 (m, 1H), 1.53 (m, 1H), 0.98 (d, J=6.9 Hz, 3H), 0.80 (d, J=6.5 Hz, 3H); $^{13}$CNMR (125 MHz, CDCl$_3$) δ 149.0, 148.7, 146.1, 130.9, 120.2, 111.2, 110.9, 87.6, 82.6, 81.2, 78.7, 69.9, 61.7, 55.9, 55.8, 35.1, 34.8, 33.2, 19.1, 13.5, 6.2; high resolution mass spectrum (ES+) m/z 513.1096 [(M+Na)+; calcd for $C_{21}H_{31}O_5INa$: 513.1114].

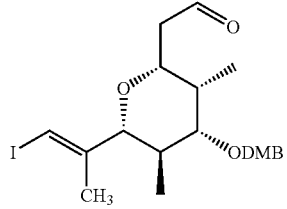

(+)-2.12

Aldehyde (+)-2.12:

To a solution of primary alcohol (+)-2.S$_3$ (0.415 g, 0.848 mmol) in dichloromethane (8.5 mL) under argon was added methylsulfoxide (0.902 mL, 12.7 mmol) and triethylamine (0.589 mL, 4.2 mmol) followed by cooling to 0° C. SO$_3$.Pyridine complex (0.337 g, 2.10 mmol) was added in one portion and after stirring for ten minutes, the reaction was warmed to room temperature. After two hours, the reaction was quenched with water (5 mL), and extracted with diethyl ether (10 mL, 3×). The combined organic extracts were dried over Na2SO4, filtered and concentrated under reduced pressure. Purification via silica gel chromatography (40% EtOAc/hexanes) afforded aldehyde (+)-2.12 (0.384 g, 92%) as a white solid. mp. 98-100° C.; [α]$_D^{20}$+36.7 (c 0.3, CHCl$_3$); IR (CHCl$_3$) 2959 (w), 2926 (m), 2848 (m), 1725 (s), 1516 (s), 1464 (m), 1263 (s), 1157 (m), 1075 (m), 1029 (s) cm−1; $^1$HNMR (500 MHz, CDCl$_3$) δ 9.74 (app t, J=1.9 Hz, 1H), 6.84 (m, 3H), 6.22 (d, J=1.0 Hz, 1H), 4.56 (d, J=11.3 Hz, 1H), 4.30 (d, J=11.3 Hz, 1H), 3.95 (ddd, J=8.6, 4.5, 2.2 Hz, 1H), 3.87 (s, 3H), 3.86 (s, 3H), 3.53 (d, J=10.3 Hz, 1H), 3.20 (dd, J=10.4, 4.6 Hz, 1H), 2.74 (ddd, J=16.8, 8.6, 1.9 Hz, 1H), 2.42 (ddd, J=16.8, 4.5, 1.9 Hz, 1H), 2.10 (m, 1H), 1.78 (d, J=1.1 Hz, 3H), 1.76 (m, 1H), 0.95 (d, J=6.9 Hz, 3H), 0.79 (d, J=6.5 Hz, 3H); $^{13}$CNMR (125 MHz, CDCl$_3$) δ 200.7, 148.9, 148.6, 145.9, 130.7, 120.2, 111.1, 110.9, 87.5, 82.3, 81.1, 73.2, 69.9, 55.9, 55.7, 46.7, 34.1, 33.0, 19.1, 13.5, 6.0; high resolution mass spectrum (ES+) m/z 511.0935 [(M+Na)+; calcd for $C_{21}H_{29}O_5INa$: 511.0957].

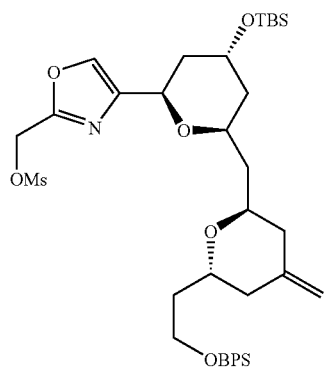

(−)-2.52

Mesylate (−)-2.52:

To known alcohol (−)-2.41 (Smith, et al. J. Am. Chem. Soc. 2001, 123, 10942) (0.419 g, 0.595 mmol), stirring in dichloromethane (37 mL) under an argon atmosphere at −10° C. was added diisopropylethylamine (0.21 mL, 1.2 mmol) followed by the dropwise addition of methanesulfonyl chloride (0.055 mL, 0.714 mmol). After forty minutes the reaction mixture was purified directly via silica gel chromatography (15% EtOAc/hexanes→30% EtOAc/hexanes) to afford mesylate (−)-2.52 (0.461 g, 99%) as a colorless oil. [α]$_D^{20}$−10.5 (c 1.0, CHCl$_3$); IR (CHCl$_3$) 2951 (b), 2856 (s), 1363 (s), 1552 (s), 1177 (s), 1111 (s), 1034 (b), 958 (s), 836 (s) cm−1; $^1$HNMR (500 MHz, CDCl$_3$) δ 7.65 (m, 4H), 7.55 (s, 1H), 7.39 (m, 6H), 5.24 (s, 2H), 4.86 (d, J=9.6 Hz, 1H), 4.72 (s, 2H), 4.20 (app t, J=2.6 Hz, 1H), 4.01 (m, 2H), 3.75 (m, 1H), 3.70 (m, 1H), 3.07 (s, 3H), 2.35 (dd, J=13.2, 4.5 Hz, 1H), 2.31 (dd, J=13.2, 4.2 Hz, 1H), 2.03 (dd, J=13.1, 5.9 Hz, 1H), 1.97 (dd, J=13.2, 6.8 Hz, 1H), 1.89 (m, 2H), 1.82 (m, 1H), 1.74 (app t, J=11.8 Hz, 1H), 1.65 (m, 2H), 1.52 (m, 3H), 1.04 (s, 9H), 0.91 (s, 9H), 0.07 (s, 6H); $^{13}$C NMR (125 MHz, CDCl$_3$) δ 156.6, 143.8, 142.4, 136.9, 135.7, 134.1, 134.0, 129.7, 129.6, 127.8, 110.3, 69.4, 69.2, 69.0, 67.5, 64.8, 62.2, 60.8, 39.8, 39.5, 39.4, 39.2, 38.6, 38.5, 36.7, 27.0, 26.0, 19.4, 18.2, −4.5, −4.6; high resolution mass spectrum (ES+) m/z 806.3529 [(M+Na)+; calcd for $C_{41}H_{61}NO_8SSi_2Na$: 806.3517].

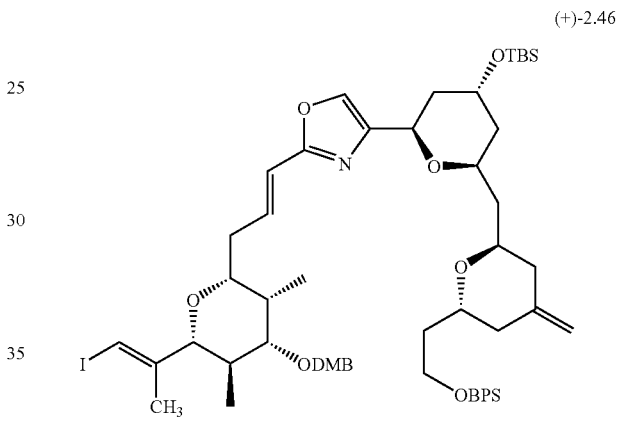

(+)-2.46

C(19-20)-E-Olefin (+)-2.46:

To a solution of mesylate (−)-2.52 (0.707 g, 0.901 mmol) in anhydrous DMF (192 mL) at room temperature under argon was added dropwise, tri-n-butylphosphine (0.901 mL, 3.61 mmol). After thirty six hours at room temperature, aldehyde (+)-2.12 (0.439 g, 0.901 mmol) in anhydrous DMF (103 mL) was added dropwise via cannula followed by dropwise addition of 1,8-diazabicyclo[5.4.0]undec-7-ene (DBU) (0.272 mL, 1.80 mmol). After stirring at room temperature for three hours, the reaction mixture was diluted with diethyl ether (80 mL) and poured into water (120 mL). The layers were separated and the aqueous layer was extracted with diethyl ether (50 mL, 5×). The combined organic extracts were washed with saturated aqueous sodium chloride (50 mL), dried over MgSO$_4$, filtered and concentrated under reduced pressure. Purification via silica gel chromatography (20% EtOAc/hexanes) afforded the C(19-20)-E-olefin product (+)-2.46 (1.01 g, 96%, 20:1, E:Z) as a white foam. [α]$_D^{20}$+22.7 (c 1.0, CHCl$_3$); IR (neat) 2967 (b), 2930 (s), 1487 (m), 1258 (s), 1110 (s), 776 (s) cm−1; $^1$HNMR (500 MHz, CDCl$_3$) δ 7.64 (m, 4H), 7.35 (m, 6H), 6.89 (d, J=1.9 Hz, 1H), 6.82 (dd, J=8.2, 1.9 Hz, 1H), 6.58 (m, 1H), 6.32 (d, J=16.0 Hz, 1H), 6.23 (s, 1H), 4.82 (dd, J=11.2, 1.9 Hz, 1H), 4.70 (s, 2H), 4.56 (d, J=11.2 Hz, 1H), 4.26 (d, J=11.2 Hz, 1H), 4.24, (m, 1H), 3.95 (m, 3H), 3.87 (s, 3H), 3.65 (m, 2H), 3.50 (d, J=10.4 Hz, 1H), 3.45 (ddd, J=14.1, 7.1, 1.8 Hz, 1H), 3.12 (dd, J=10.4, 4.5 Hz, 1H), 2.52 (m, 1H), 2.34 (m, 3H), 2.08 (m, 1H), 2.00 (dd, J=13.0, 7.0 Hz, 1H), 1.93 (dd, J=13.0, 7.0 Hz, 1H), 1.86 (m, 2H), 1.82 (s, 3H), 1.80 (m, 2H), 1.75 (m, 4H), 1.61 (m, 3H), 1.48 (m, 3H), 1.06 (s, 9H), 0.97 (d, J=6.7 Hz, 3H), 0.91 (s, 9H), 0.76 (d, J=6.3 Hz, 3H), 0.06 (s, 6H); $^{13}$CNMR (125 MHz, CDCl$_3$) δ 160.7, 149.0, 148.6, 146.3, 143.3, 142.3, 135.6, 135.5, 135.1, 134.2, 133.9, 133.8, 130.9, 129.5, 127.6, 120.2, 118.8, 111.1, 110.1, 87.5, 82.8, 80.9, 77.4, 77.2, 69.9, 69.0, 68.8, 67.4, 64.7, 60.6, 55.9, 55.7, 39.6, 39.3, 39.2, 38.9, 38.2, 36.6, 36.2, 33.7, 33.5, 33.3, 30.3, 26.8, 25.8, 19.1, 18.0, 13.5, 5.7, −4.8, −4.9; high resolution mass spectrum (ES$^+$) m/z 1182.4735 [(M+Na)$^+$; calcd for C$_{61}$H$_{86}$INO$_9$Si$_2$Na: 1182.4886].

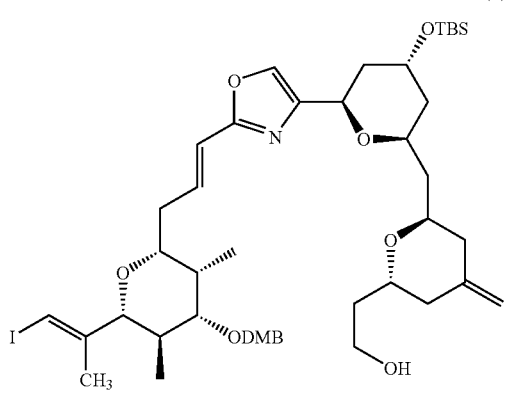

(+)-2.54

Primary Alcohol (+)-2.54:

Under an argon atmosphere, a solution of C(19-20)-E-olefin product (+)-2.46 (0.153 g, 0.132 mmol) in THF (18 mL) was added dropwise via cannula to a solution of potassium hydroxide (0.627 g, 11.0 mmol), and 18-crown-6 (1.04 g, 3.95 mmol) in THF (20 mL) and water (1.5 mL) at 0° C. After forty minutes, the solution was warmed to room temperature and after five hours, the reaction mixture was poured over saturated aqueous sodium chloride (25 mL) and extracted with ethyl acetate (15 mL, 3×). The combined organic extracts were dried over MgSO$_4$ and concentrated in vacuo. Purification via silica gel chromatography (40% EtOAc/hexanes) afforded primary alcohol (+)-2.54 (0.106 g, 87%) as a colorless oil. [α]$_D^{20}$+25.0 (c 1.0, CHCl$_3$); IR (neat) 2927 (b), 2831 (s), 1516 (s), 1464 (m), 1258 (b), 1031 (m), 835 (s) cm$^{-1}$; $^1$HNMR (500 MHz, CDCl$_3$) δ 7.46 (s, 1H), 6.82 (m, 3H), 6.59 (ddd, J=15.6, 8.6, 6.7 Hz, 1H), 6.33 (d, J=16.0 Hz, 1H), 6.23 (s, 1H), 4.83 (dd, J=10.8, 2.6 Hz, 1H), 4.76 (s, 1H), 4.72 (s, 1H), 4.56 (d, J=11.5 Hz, 1H), 4.27 (m, 1H), 4.26 (d, J=11.2 Hz, 1H), 4.06 (m, 1H), 4.01 (m, 1H), 3.95 (m, 1H), 3.87 (s, 6H), 3.71 (m, 2H), 3.50 (d, J=10.1 Hz, 1H), 3.45 (ddd, J=13.1, 6.7, 1.9 Hz, 1H), 3.13 (dd, J=10.1, 4.5 Hz, 1H), 2.52 (m, 1H), 2.33 (m, 3H), 2.26 (dd, J=13.4, 4.1 Hz, 1H), 2.08 (m, 1H), 2.00 (m, 2H), 1.92 (m, 1H), 1.82 (s, 3H), 1.76 (m, 4H), 1.48 (m, 4H), 0.95 (d, J=7.1 Hz, 3H), 0.91 (s, 9H), 0.78 (d, J=6.7 Hz, 3H), 0.08 (s, 3H), 0.07 (s, 3H); $^{13}$CNMR (125 MHz, CDCl$_3$) δ 161.3, 149.0, 148.6, 146.5, 142.8, 142.1, 141.8, 136.6, 134.6, 131.2, 120.5, 118.5, 111.5, 111.3, 110.6, 87.8, 83.1, 81.1, 77.7, 77.3, 70.8, 70.2, 70.1, 67.3, 65.0, 60.4, 56.2, 56.0, 40.3, 39.4, 39.0, 38.9, 38.1, 36.5, 36.4, 33.9, 33.5, 26.1, 19.4, 18.1, 13.7, 5.9, −4.6; high resolution mass spectrum (ES$^+$) m/z 944.3605 [(M+Na)$^+$; calcd for C$_{45}$H$_{68}$INO$_9$SiNa: 944.3652].

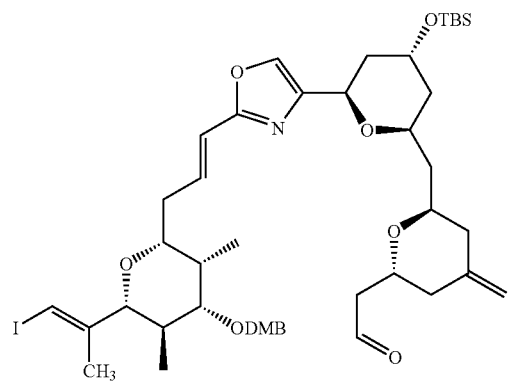

(+)-2.55

Aldehyde (+)-2.55:

To a solution of alcohol (+)-2.54 (61.0 mg, 0.066 mmol) in dichloromethane (24 mL) under argon at 0° C. was added solid sodium bicarbonate (5.5 mg, 0.066 mmol) followed by Dess-Martin periodinane (56.0 mg, 0.132 mmol). After thirty minutes, the reaction was warmed to room temperature and after two total hours of reaction, the solution was poured into saturated aqueous sodium bicarbonate (15 mL) and the layers were separated. The aqueous layer was extracted with dichloromethane (15 mL, 3×), dried over MgSO$_4$ and concentrated under reduced pressure. Purification via silica gel chromatography (30% EtOAc/hexanes) afforded aldehyde (+)-2.55 (59.4 mg, 98%) as a colorless oil. [α]$_D^{20}$+35.0 (c 1.0, CHCl$_3$); IR (neat) 2931 (b), 2851 (s), 1724 (s), 1510 (s), 1461 (s), 1366 (m), 1257 (b), 1098 (b), 1028 (s), 914 (b), 834 (s) cm$^{-1}$; $^1$HNMR (500 MHz, CDCl$_3$) δ 9.74 (app t, J=2.6 Hz, 1H), 7.47 (s, 1H), 6.82 (m, 3H), 6.59 (m, 1H), 6.32 (s, 1H), 4.83 (dd, J=8.9, 5.2 Hz, 1H), 4.79 (s, 1H), 4.77 (s, 1H), 4.56 (d, J=11.2 Hz, 1H), 4.31 (m, 1H), 4.25 (d, J=10.8 Hz, 1H), 4.24 (m, 1H), 4.00 (m, 2H), 3.87 (s, 6H), 3.49 (d, J=10.4 Hz, 1H), 3.45 (ddd, J=7.4, 7.4, 1.8 Hz, 1H), 3.12 (dd, J=10.0, 4.8 Hz, 1H), 2.64 (dd, J=7.8, 3.0 Hz, 1H), 2.61 (dd, J=7.8, 2.6 Hz, 1H), 2.52 (m, 1H), 2.48 (dd, J=6.0, 2.2 Hz, 1H), 2.45 (dd, J=6.0, 1.9 Hz, 1H), 2.32 (m, 3H), 2.08 (m, 2H), 1.95 (m, 2H), 1.82 (s, 2H), 1.75 (m, 3H), 1.43 (m, 3H), 0.95 (d, J=7.1 Hz, 3H), 0.91 (s, 9H), 0.79 (d, J=6.7 Hz, 3H), 0.07 (s, 3H), 0.06 (s, 3H); $^{13}$CNMR (125 MHz, CDCl$_3$) δ 200.9, 160.9, 149.0, 148.6, 146.3, 143.1, 140.9, 136.1, 135.3, 134.2, 131.9, 120.2, 118.7, 111.1, 110.9, 87.5, 82.8, 80.9, 77.4, 77.1, 69.9, 69.6, 69.1, 67.3, 67.2, 64.6, 55.9, 55.7, 47.7, 39.6, 38.9, 38.8, 38.0, 36.2, 33.6, 33.3, 29.6, 25.8, 19.1, 13.5, 5.7, −4.9, −5.0; high resolution mass spectrum (ES$^+$) m/z 942.3552 [(M+Na)$^+$; calcd for C$_{45}$H$_{66}$INO$_9$SiNa: 942.3455].

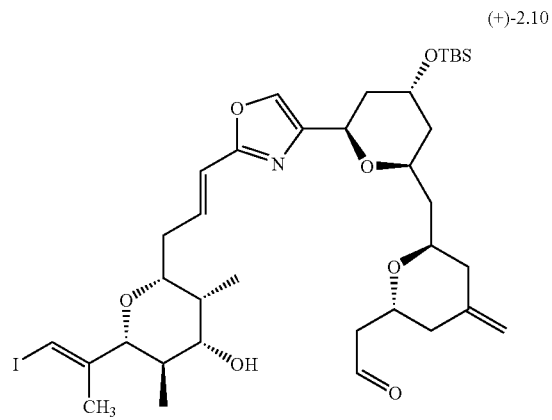

(+)-2.10

Secondary Alcohol-Aldehyde (+)-2.10:

To a solution of aldehyde (+)-2.55 (59.4 mg, 0.064 mmol) in dichloromethane (10 mL) and pH 7 buffer (2.7 mL) under an argon atmosphere at room temperature was added 2,3-dichloro-5,6-dicyano-1,4-benzoquinone (DDQ) (29.3 mg, 0.129 mmol). After stirring for four hours, the reaction was poured over saturated aqueous sodium bicarbonate (10 mL), extracted with dichloromethane (8 mL, 3×), dried over $MgSO_4$, filtered and concentrated under reduced pressure. Purification via silica gel chromatography (25% EtOAc/hexanes) afforded secondary alcohol-aldehyde (+)-2.10 (50.6 mg, 95%) as a colorless oil. $[\alpha]_D^{20}$+34.0 (c 0.1, $CHCl_3$); IR (neat) 3429 (b), 2924 (s), 2853 (s), 1725 (s), 1461 (s), 1377 (m), 1252 (s), 1098 (s), 1049 (b), 900 (b), 835 (s), 776 (s) $cm^{-1}$; $^1$HNMR (500 MHz, $CDCl_3$) δ 9.74 (app t, J=2.2 Hz, 1H), 7.45 (s, 1H), 6.56 (m, 1H), 6.30 (d, J=16.0 Hz, 1H), 6.24 (s, 1H), 4.81 (app t, J=7.4 Hz 1H), 4.79 (s, 1H), 4.77 (s, 1H), 4.31 (m, 1H), 4.24 (br s, 1H), 3.99 (m, 2H), 3.48 (m, 1H), 3.47 (d, J=10.3 Hz, 1H), 3.41 (dd, J=10.4, 4.8 Hz, 1H), 2.64 (dd, J=7.8, 2.6 Hz, 1H), 2.51 (m, 1H), 2.48 (dd, J=6.0, 2.2 Hz, 1H), 2.39 (dd, J=6.0, 1.9 Hz, 1H), 2.29 (m, 3H), 1.96 (m, 3H), 1.88 (m, 1H), 1.83 (s, 3H), 1.80 (m, 2H), 1.44 (m, 4H), 0.94 (d, J=6.7 Hz, 3H), 0.91 (s, 9H), 0.80 (d, J=6.7 Hz, 3H), 0.07 (s, 3H), 0.06 (s, 3H); $^{13}$CNMR (125 MHz, $CDCl_3$) δ 200.9, 161.3, 146.6, 143.6, 135.8, 134.7, 119.2, 111.6, 87.8, 81.4, 78.2, 70.1, 69.6, 67.8, 67.7, 65.1, 48.2, 40.1, 39.5, 39.4, 39.3, 39.1, 38.6, 38.4, 36.4, 35.1, 30.1, 26.3, 19.7, 18.5, 13.6, 5.9, −4.3, −4.4; high resolution mass spectrum (ES$^+$) m/z 792.2767 [(M+Na)$^+$; calcd for $C_{36}H_{56}INO_7SiNa$: 792.2736].

(+)-2.56

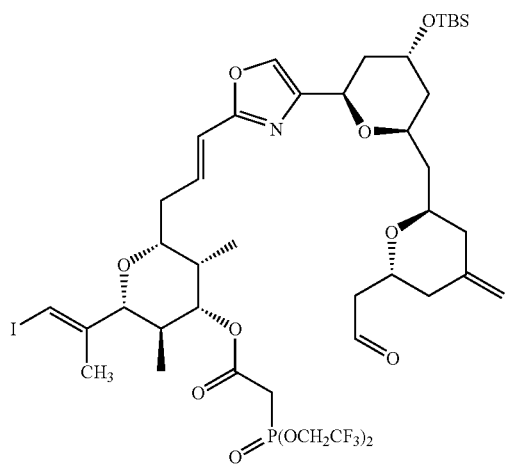

Phosphonate Ester (+)-2.56:

To a solution of secondary alcohol-aldehyde (+)-2.10 (30.5 mg, 0.039 mmol) in dichloromethane (7.3 mL) under an argon atmosphere at room temperature was added dropwise via cannula, trifluoroethylphosphonate acid 3.45 (59.0 mg, 0.195 mmol) as a solution in dichloromethane (7.3 mL) and allowed to stir for five minutes. 1-[3-(dimethylamino)propyl]-3-ethylcarbodiimide methiodide (EDCI.MeI) (58.9 mg, 0.198 mmol) followed by hydroxybenzatriazole (HOBT) (catalytic) were added and the reaction was allowed to stir at room temperature. After thirty minutes, the reaction solution was concentrated under reduced pressure to ½ volume and purified directly via silica gel chromatography (40% EtOAc/hexanes) to afford phosphonate ester (+)-2.56 (38.3 mg, 93%) as a colorless oil. $[\alpha]_D^{20}$+20.0 (c 0.1, $CHCl_3$); IR (neat) 2928 (b), 1734 (s), 1268 (s), 1174 (s), 1098 (m), 963 (s), 893 (b), 835 (s), 775 (s) $cm^{-1}$; $^1$HNMR (500 MHz, $CDCl_3$) δ 9.74 (app t, J=2.2 Hz, 1H), 7.45, (s, 1H), 6.53 (m, 1H), 6.29 (d, J=16 Hz, 1H), 6.28 (s, 1H), 4.82 (app t, J=7.1 Hz, 1H), 4.79 (s, 1H), 4.77 (s, 1H), 4.72 (dd, J=11.2, 4.8 Hz, 1H), 4.39 (m, 4H), 4.31 (m, 1H), 4.24 (br s, 1H), 3.99 (m, 2H), 3.56 (m, 2H), 3.19 (s, 1H), 3.14 (s, 1H), 2.64 (dd, J=7.4, 2.6 Hz, 1H), 2.60 (dd, J=7.8, 2.9 Hz, 1H), 2.55 (m, 1H), 2.45 (m, 2H), 2.25 (m, 3H), 2.07 (m, 2H), 1.96 (m, 4H), 1.86 (m, 2H), 1.84 (m, 2H), 1.83 (s, 3H), 1.61 (m, 2H), 1.46 (m, 3H), 0.95 (d, J=6.7 Hz, 3H), 0.91, (s, 9H), 0.72 (d, J=6.4 Hz, 3H), 0.07 (s, 3H), 0.06 (s, 3H); $^{13}$CNMR (125 MHz, $CDCl_3$) δ 200.9, 163.9, 160.7, 145.3, 143.1, 140.8, 134.6, 134.2, 119.0, 111.1, 87.1, 81.7, 80.5, 77.1, 77.0, 69.6, 69.0, 67.3, 67.2, 64.6, 62.5, 62.4, 47.7, 39.6, 38.9, 38.8, 38.7, 38.1, 35.8, 35.2, 34.6, 33.5, 32.0, 29.6, 25.8, 19.1, 18.0, 12.9, 6.0, −4.9, −5.0; high resolution mass spectrum (ES$^+$) m/z 1078.2700 [(M+Na)$^+$; calcd for $C_{45}H_{68}INO_9SiNa$: 1078.2657].

(+)-2.5

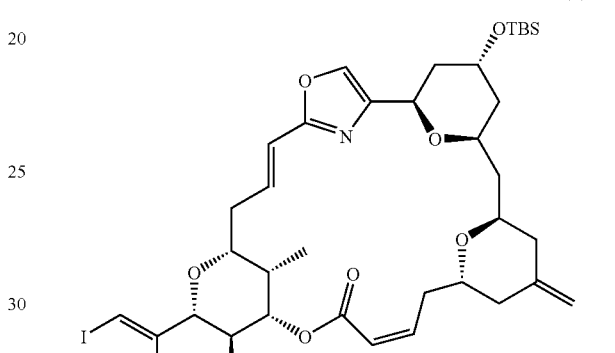

Z-C(2-3)-Macrocycle (+)-2.5:

To a flask charged with freshly distilled toluene (34 mL) at room temperature under argon was added 18-crown-6 (0.710 g, 2.70 mmol) and potassium carbonate (79.0 mg, 0.576 mmol). After stirring for three hours, a solution of phosphonate ester (+)-2.56 (50.7 mg, 0.048 mmol) in toluene (34 mL) was added dropwise via cannula and allowed to stir at room temperature. After three hours, the reaction mixture was poured into saturated aqueous sodium chloride (30 mL) and the resultant layers of the biphasic mixture were separated. The aqueous layer was extracted with ethyl acetate (20 mL, 3×) and the combined organic extracts were dried over $MgSO_4$ and concentrated in vacuo. Purification by preparative thin layer chromatography (30% EtOAc/hexanes) afforded Z-C(2-3)-macrocycle (+)-2.5 (22.2 mg, 68% yield) as a white foam and E-C(2-3)-macrocycle (+)-2.S$_4$ (10.5 mg, 29%) as a light yellow oil. Total (32.7 mg, 96%, 2.5:1 Z:E). Z-C(2-3)-Macrocycle (+)-2.5: $[\alpha]_D^{20}$+47.5 (c 0.3, $CHCl_3$); IR (neat) 2926 (s) 2854 (s), 1718 (s), 1252 (s), 1186 (s), 1091 (s), 1034 (m), 835 (s) $cm^{-1}$; $^1$HNMR (500 MHz, $C_6D_6$) δ 6.94 (s, 1H), 6.84 (m, 1H), 6.16 (d, J=15.9 Hz, 1H), 6.02 (s, 1H), 5.76 (dd, J=13.4, 11.2 Hz, 1H), 5.43 (ddd, J=10.4, 10.4, 2.8 Hz, 1H), 5.16 (s, 1H), 4.95 (d, J=11.3 Hz, 1H), 4.72 (s, 1H), 4.48 (dd, J=15.5, 11.2 Hz, 1H), 4.38 (m, 1H), 4.24 (app t, J=10.8 Hz, 1H), 4.06 (m, 1H), 4.00 (app t, J=2.5 Hz, 1H), 3.94 (m, 1H), 3.27 (m, 1H), 3.24 (d, J=10.2 Hz, 1H), 3.04 (d, J=11.9 Hz, 1H), 2.57 (app t, J=6.4 Hz, 1H), 2.41 (d, J=3.1 Hz, 1H), 2.32 (m, 2H), 2.09 (ddd, J=13.1, 11.8, 5.0 Hz, 1H), 1.99 (app t, J=11.8 Hz, 1H), 1.94 (d, J=12.9 Hz, 1H), 1.84 (m, 1H), 1.79 (d, J=0.9 Hz, 3H), 1.63 (m, 3H), 1.47 (d, J=13.4 Hz, 1H), 1.33 (m, 2H), 0.93 (d, J=6.8 Hz, 3H), 0.92 (s, 9H), 0.57 (d, J=6.5 Hz, 3H), 0.00 (s, 3H), −0.01 (s, 3H); $^{13}$CNMR (125 MHz, $C_6D_6$) δ 165.7, 161.6, 146.7, 145.8, 143.8, 143.0, 134.1, 133.8, 121.2, 120.2, 110.4, 88.1, 81.5, 79.7, 78.8, 73.6, 69.9, 69.3, 67.6, 65.8, 42.4, 40.5, 39.9, 37.9, 36.3, 34.7, 33.0, 32.3, 31.1, 26.3, 19.6, 18.6, 13.3, 6.5, −4.4, −4.5; high resolution mass spectrum (ES+) m/z 816.2741 [(M+Na)+; calcd for $C_{38}H_{56}INO_7SiNa$: 816.2763].

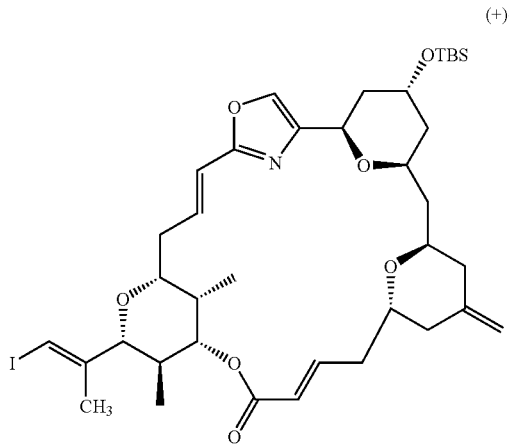

(+)-2.S4

E-C(2-3)-Macrocycle (+)-2.S4: $[\alpha]_D^{20}$+26.7 (c 0.9, CHCl3); IR (neat) 2933 (b), 2794 (s), 1718 (s), 1654 (s), 1252 (m), 1152 (s), 1087 (m), 1024 (s), 833 (s), 775 (s) cm$^{-1}$; 1HNMR (500 MHz, $C_6D_6$) δ 7.20 (m, 1H), 6.90 (s, 1H), 6.83 (m, 1H), 6.11 (d, J=15.7 Hz, 1H), 6.01 (d, J=15.2 Hz, 1H), 5.95 (s, 1H), 4.93 (d, J=11.6 Hz, 1H), 4.94 (m, 1H), 4.67 (s, 1H), 4.58 (s, 1H), 4.34 (br s, 1H), 3.99 (s, 1H), 3.90 (app q, J=7.1 Hz, 1H), 3.37 (app t, J=9.1 Hz, 1H), 3.31 (m, 1H), 3.19 (d, J=10.0 Hz, 1H), 2.41 (d, J=13.9 Hz, 1H), 2.26 (m, 2H), 2.12 (d, J=10.6 Hz, 1H), 2.08 (d, J=10.5 Hz, 1H), 2.02 (m, 1H), 1.89 (dd, J=13.0, 2.6 Hz, 1H), 1.80 (m, 3H), 1.75 (d, J=1.0 Hz, 3H), 1.67 (m, 3H), 1.61 (m, 1H), 1.35 (m, 2H), 0.96 (m, 9H), 0.74 (d, J=6.7 Hz, 3H), 0.66 (d, J=6.5 Hz, 3H), 0.00 (s, 3H), −0.01 (s, 3H); 13CNMR (125 MHz, $C_6D_6$) δ 167.3, 162.4, 147.6, 146.9, 143.9, 142.8, 135.7, 134.6, 124.1, 119.2, 111.4, 88.1, 81.5, 78.8, 77.4, 71.0, 70.0, 68.7, 66.4, 66.2, 41.6, 41.3, 40.4, 38.8, 38.6, 38.5, 35.8, 35.3, 33.2, 26.6, 26.5, 19.8, 18.8, 13.6, 6.1, −4.2; high resolution mass spectrum (ES+) m/z 816.2788 [(M+Na)+; calcd for $C_{38}H_{56}INO_7SiNa$: 816.2763].

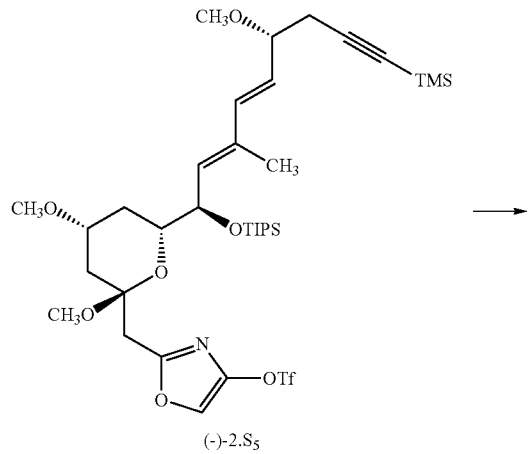

(−)-2.S5

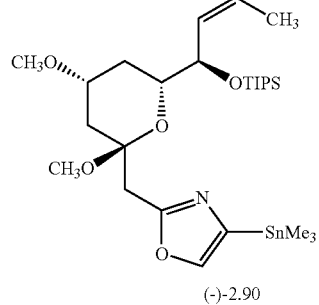

(−)-2.90

C(45-46)-TMS-Alkynyl Sidechain (−)-2.90:

Known oxazole triflate, (−)-2.S5 (Smith, et al. *J. Am. Chem. Soc.* 2001, 123, 10942) (69.6 mg, 0.089 mmol) was combined with hexamethylditin (0.026 mL, 0.125 mmol) in a 100 mL sealed tube and azeotroped from benzene (5 mL, 3×) followed by drying under vacuum for one hour. In a glove bag, under an inert argon atmosphere to the sealed tube was added, flame dried lithium chloride (60.0 mg, 1.40 mmol), tetrakis(triphenylphosphine)palladium [Pd(PPh3)4] (15.0 mg, 0.013 mmol) and dioxane (0.90 mL), (freeze pump thawed, 3×). The reaction was heated to 90° C. behind a blast shield and after fifteen hours, the reaction was cooled to room temperature and purified directly via silica gel chromatography (15% EtOAc/hexanes) to afford C(45-46)-TMS-alkynyl sidechain (−)-2.90 (46.4 mg, 64%) as a colorless oil. $[\alpha]_D^{20}$−37.5 (c 0.1, $CH_2Cl_2$); IR (neat) 2927 (s), 2865 (s), 1462 (m), 1248 (s), 1093 (b), 843 (s) cm$^{-1}$; 1HNMR (500 MHz, CDCl3) δ 7.45 (s, 1H), 6.24 (d, J=15.7 Hz, 1H), 5.55 (dd, J=15.6, 7.6 Hz, 1H), 5.43 (d, J=8.8 Hz, 1H), 4.63 (dd, J=8.7, 6.1 Hz, 1H), 3.78 (app q, J=3.2 Hz, 1H), 3.57 (m, 3H), 3.34 (s, 3H), 3.31 (s, 3H), 3.29 (s, 3H), 3.03 (d, J=14.9 Hz, 1H), 2.58 (dd, J=16.7, 5.7 Hz, 1H), 2.44 (dd, J=16.7, 6.8 Hz, 1H), 2.20 (dddd, J=12.7, 4.6, 4.5, 1.6 Hz, 1H), 2.00 (dd, J=12.2, 4.4 Hz, 1H), 1.78 (d, J=0.9 Hz, 3H), 1.37 (dd, J=12.6, 11.2 Hz, 1H), 1.06 (m, 22H), 0.31 (s, 9H), 0.14 (s, 9H); 13CNMR (125 MHz, CDCl3) δ 160.9, 145.1, 137.2, 134.1, 133.0, 127.4, 103.2, 99.9, 86.4, 80.6, 73.8, 73.5, 71.7, 56.5, 55.5, 47.8, 39.2, 35.6, 32.0, 29.6, 27.0, 18.0, 17.9, 13.6, 12.3, 0.04; high resolution mass spectrum (ES+) m/z 820.3400 [(M+Na)+; calcd for $C_{37}H_{67}NO_6Si_2SnNa$: 820.3426].

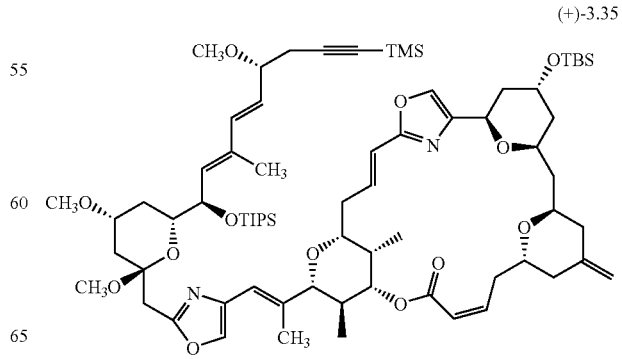

(+)-3.35

Protected C(45-46)-TMS-Alkynyl-Phorboxazole (+)-3.35:

Vinyliodide macrocycle (+)-2.5 (13.8 mg, 0.017 mmol) and C(45-46)-TMS-alkynyl side chain (−)-2.90 (21.0 mg, 0.026 mmol) were combined in a flame dried round bottom flask (5 mL), azeotroped from benzene (2 mL, 3×) and dried under vacuum for two hours. To the flask under an argon atmosphere were added tris(dibenzylideneacetone)dipalladium-chloroform adduct [$Pd_2(dba)_3 \cdot CHCl_3$] (3.6 mg, 0.003 mmol), triphenylarsine ($AsPh_3$) (6.4 mg, 0.021 mmol) and $Ph_2PO_2NBu_4$. (12 mg, 0.026 mmol) followed by introduction of DMF (0.17 mL, sparged with argon, thirty minutes) and diisopropylethylamine (0.003 mL, 0.017 mmol). After the reaction was allowed to stir for sixteen hours at room temperature, the light brown reaction mixture was introduced directly onto a silica gel column, (20% EtOAc/hexanes→30% EtOAc/hexanes) to afford protected C(45-46)-TMS-alkynyl-phorboxazole (+)-3.35 (14.9 mg, 68%) as a light yellow oil. $[\alpha]_D^{20}$+1.3 (c 0.2, $CHCl_3$); IR (neat) 2925 (b), 1718 (s), 1456 (b), 1250 (s), 1187 (s), 1091 (s), 1053 (b), 840 (s) cm$^{-1}$; $^1$HNMR (500 MHz, $C_6D_6$) δ 6.96 (s, 1H), 6.90 (m, 1H), 6.37 (s, 1H), 6.32 (d, J=15.7 Hz, 1H), 6.20 (d, J=15.9 Hz, 1H), 5.79 (dd, J=11.2, 2.3 Hz, 1H), 5.69 (dd, J=15.7, 7.3 Hz, 1H), 5.57 (d, J=8.9 Hz, 1H), 5.47 (ddd, J=10.7, 10.5, 2.9 Hz, 1H), 5.18 (s, 1H), 4.96 (dd, J=11.3, 2.0 Hz, 1H), 4.77 (m, 2H), 4.62 (dd, J=11.2, 4.4 Hz, 1H), 4.39 (m, 1H), 4.25 (app t, J=10.4 Hz, 1H), 4.08 (m, 1H), 4.03 (d, J=2.6 Hz, 1H), 3.95 (m, 1H), 3.76 (m, 1H), 3.69 (app t, J=6.9 Hz, 1H), 3.68 (m, 1H), 3.52 (dd, J=9.4, 4.6 Hz, 1H), 3.45 (d, J=10.1 Hz, 1H), 3.41 (s, 3H), 3.34 (d, J=14.7 Hz, 1H), 3.28 (app t, J=4.8 Hz, 1H), 3.23 (app t, J=5.0 Hz, 1H), 3.09 (s, 3H), 3.08 (s, 3H), 3.04 (d, J=11.4 Hz, 1H), 2.95 (d, J=14.8 Hz, 1H), 2.66 (app t, J=6.3 Hz, 1H), 2.60 (m, 1H), 2.58 (dd, J=16.7, 5.7 Hz, 1H), 2.44 (dd, J=16.7, 6.8 Hz, 1H), 2.42 (m, 2H), 2.37 (dd, J=12.8, 5.5 Hz, 1H), 2.17 (dd, J=10.0, 7.7 Hz, 1H), 2.10 (m, 1H), 2.09 (d, J=0.6 Hz, 3H), 2.02 (d, J=11.8 Hz, 1H), 1.98 (d, J=13.0 Hz, 1H), 1.77 (d, J=0.8 Hz, 3H), 1.65 (m, 3H), 1.49 (d, J=13.2 Hz, 1H), 1.35 (m, 3H), 1.17 (m, 22H), 1.05 (d, J=6.9 Hz, 3H), 0.94 (s, 9H), 0.77 (d, J=6.5 Hz, 3H), 0.24 (s, 9H), 0.03 (s, 3H), 0.01 (s, 3H); $^{13}$CNMR (125 MHz, $C_6D_6$) δ 165.8, 161.7, 160.0, 145.5, 143.8, 143.0, 139.2, 138.2, 137.3, 136.8, 135.0, 134.4, 133.8, 133.5, 121.4, 120.1, 119.5, 110.5, 104.6, 100.8, 90.0, 86.8, 81.0, 80.2, 78.7, 74.7, 74.1, 73.7, 72.7, 69.9, 69.3, 67.7, 65.9, 56.7, 55.6, 48.3, 42.4, 40.5, 40.4, 40.0, 37.9, 36.4, 36.3, 34.9, 33.1, 32.4, 31.2, 30.5, 27.9, 26.3, 18.7, 18.6, 14.6, 14.1, 13.7, 13.2, 6.6, 1.7, 0.6, −4.5, −4.4; high resolution mass spectrum (ES$^+$) m/z 1321.7641 [(M+Na)$^+$; calcd for $C_{72}H_{114}N_2O_{13}Si_3Na$: 1321.7626].

Bromoalkyne (+)-2.92:

Protected C(45-46)-TMS-alkynyl-phorboxazole (+)-3.35 (4.4 mg, 0.0034 mmol) was introduced into a flame dried round bottom flask, azeotroped from benzene (2 mL, 3×) and dried under vacuum. After one hour, under an argon atmosphere, (+)-3.35 was stirred in HPLC grade acetone (2.1 mL) at 0° C. After five minutes, silver nitrate (catalytic) followed by N-bromosuccinimide (NBS) (3.3 mg, 0.018 mmol) were added and after thirty minutes, the reaction mixture was warmed to room temperature. After two hours and thirty minutes of total reaction time, the reaction solution was re-cooled to 0° C. and quenched via dropwise addition of saturated aqueous sodium thiosulfate (2 mL), stirred until the initial yellow color dissipated and then poured into saturated aqueous sodium bicarbonate (5 mL). The layers of the biphasic mixture were separated and the aqueous layer was extracted with dichloromethane (8 mL, 3×), dried over $MgSO_4$, filtered and concentrated under reduced pressure. Purification via silica gel chromatography (40% EtOAc/hexanes) afforded bromoalkyne (+)-2.92 (4.2 mg, 95%) as a white amorphous solid. $[\alpha]_D^{20}$+3.1 (c 0.04, $CH_2Cl_2$); IR (neat) 2921 (b), 2861 (s), 1719 (s), 1461 (m), 1371 (m), 1187 (s), 1093 (s), 884 (w); $^1$HNMR (500 MHz, $C_6D_6$) δ 7.20 (s, 1H), 6.95 (s, 1H), 6.88 (m, 1H), 6.35 (s, 1H), 6.23 (d, J=15.8 Hz, 1H), 6.19 (d, J=15.8 Hz, 1H), 5.79 (dd, J=11.2, 2.5 Hz, 1H), 5.54 (d, J=10.7 Hz, 1H), 5.53 (dd, J=15.3, 7.3 Hz, 1H), 5.45 (ddd, J=10.7, 10.7, 2.7 Hz, 1H), 5.17 (s, 1H), 4.95 (d, J=11.2 Hz, 1H), 4.74 (s, 1H), 4.73 (m, 1H), 4.61 (dd, J=11.2, 4.3 Hz, 1H), 4.39 (m, 1H), 4.23 (m, 1H), 4.06 (m, 1H), 4.02 (m, 1H), 3.97 (m, 1H), 3.75 (ddd, J=12.1, 7.8, 1.8 Hz, 1H), 3.69 (m, 1H), 3.54 (dd, J=13.2, 6.6 Hz, 1H), 3.43 (d, J=9.9 Hz, 1H), 3.40 (s, 3H), 3.33 (d, J=14.7 Hz, 1H), 3.07 (s, 3H), 3.04 (s, 3H), 2.94 (d, J=14.8 Hz, 1H), 2.65 (m, 1H), 2.56 (dd, J=12.9, 3.3 Hz, 1H), 2.42 (m, 4H), 2.37 (dd, J=16.7, 5.7 Hz, 1H), 2.24 (dd, J=16.6, 6.7 Hz, 1H), 2.14 (m, 1H), 2.08 (s, 3H), 2.03 (d, J=11.4 Hz, 1H), 1.97 (m, 1H), 1.70 (d, J=0.8 Hz, 3H), 1.63 (m, 5H), 1.48 (d, J=13.3 Hz, 1H), 1.34 (m, 5H), 1.16 (m, 21H), 1.04 (d, J=6.8 Hz, 3H), 0.92 (s, 9H), 0.76 (d, J=6.4 Hz, 3H), 0.09 (s, 3H), −0.01 (s, 3H); $^{13}$CNMR (125 MHz, $C_6D_6$) δ 165.1, 161.1, 159.4, 144.9, 143.2, 142.3, 138.7, 137.6, 137.1, 136.1, 134.1, 133.9, 133.2, 133.1, 120.8, 119.6, 118.8, 109.8, 100.3, 89.4, 80.2, 79.6, 78.2, 77.1, 74.1, 73.1, 72.0, 69.3, 68.6, 67.1, 65.3, 56.0, 55.0, 47.7, 47.6, 41.8, 39.9, 39.8, 39.7, 39.3, 37.3, 35.7, 35.5, 34.3, 32.5, 31.8, 30.5, 29.9, 26.9, 25.7, 18.0, 17.8, 13.9, 13.4, 13.1, 12.7, 6.0, −5.0, −5.1; high resolution mass spectrum (ES$^+$) m/z 1327.6339 [(M+Na)$^+$; calcd for $C_{69}H_{105}O_{13}N_2Si_2BrNa$: 1327.6343].

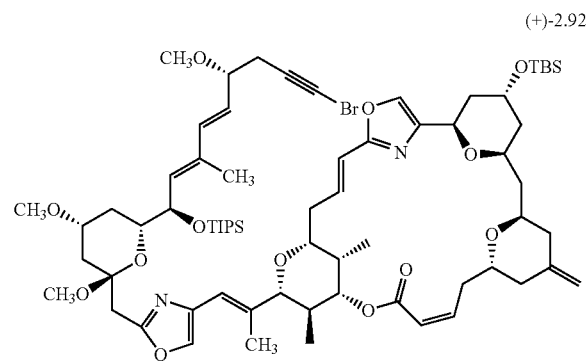

(+)-2.92

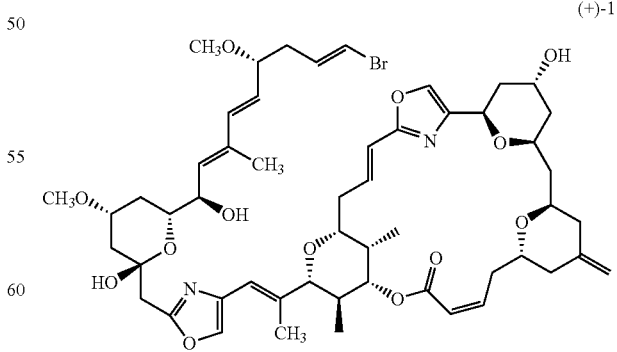

(+)-1

Phorboxazole A (+)-1:

In a flame dried round bottom flask, bromoalkyne (+)-2.92 (4.2 mg, 0.0032 mmol) was azeotroped from benzene (2 mL, 3×) and dried under vacuum. After one hour, under an argon atmosphere at room temperature, (+)-2.92 was dissolved in freshly distilled THF (1.5 mL) followed by the addition of bis(triphenylphosphine)palladium(II)chloride [PdCl$_2$(PPh$_3$)$_2$] (0.25 mL, 0.0006 mmol of stock solution; 2.0 mg/1.0 mL THF) and tri-n-butyltin hydride (0.002 mL, 0.0071 mmol). After fifteen minutes, tri-n-butyltin hydride (0.002 mL, 0.0071 mmol) was added and allowed to stir for twenty minutes at which time, the reaction was quenched via dropwise addition of saturated aqueous sodium bicarbonate (5 mL). The layers of the bisphasic mixture were separated and the aqueous layer was extracted with dichloromethane (8 mL, 3×). The combined organic extracts were dried over MgSO$_4$, filtered and concentrated under reduced pressure. Filtration through a plug of silica gel (20% EtOAc/hexanes) and concentration under reduced pressure afforded vinylstannane 2.S$_6$.

Vinylstannane 2.S$_6$, under an argon atmosphere was dissolved in anhydrous acetonitrile (2.0 mL) and cooled to 0° C. After five minutes, N-bromosuccinimide (NBS) (1.8 mg, 0.001 mmol) was added and following thirty minutes, the reaction was quenched via dropwise addition of saturated aqueous sodium thiosulfate (3 mL) and stirred until the resultant yellow color dissipated. The solution was poured into saturated aqueous sodium bicarbonate (5 mL) and extracted with dichloromethane (5 mL, 4×). The combined organic extracts were dried over MgSO$_4$, filtered and concentrated under reduced pressure. Filtration through a plug of silica gel (40% EtOAc/hexanes) and concentration under reduced pressure afforded protected phorboxazole A 2.S$_7$.

Protected phorboxazole A 2.S$_7$ under an argon atmosphere was dissolved in freshly distilled THF (1.7 mL) followed by the dropwise addition of 6% HCl (0.67 mL) at room temperature. After ninety six hours, the reaction mixture was cooled to 0° and poured into saturated aqueous sodium bicarbonate (5 mL) and extracted with dichloromethane (5 mL, 3×) followed by ethyl acetate (5 mL, 3×). The combined organic extracts were dried over MgSO$_4$, filtered and concentrated under reduced pressure. Purification via silica gel chromatography (100% EtOAc→10% methanol/EtOAc) afforded phorboxazole A (+)-1 (1.1 mg, 6:1-C(46):C(45) vinyl bromide). Further purification via reverse phase HPLC (ZORBAX C$_{18}$ column, acetonitrile/H$_2$O (55/45) eluent) afforded phorboxazole A (+)-1 (0.90 mg, 35% over 3-steps after HPLC purification) which matched the $^1$HNMR, [α]$_D^{20}$, and high resolution mass spectrum of natural (+)-phorboxazole A: [α]$_D^{20}$+ 43.4(c 0.04, CH$_2$Cl$_2$), high resolution mass spectrum (ES$^+$) m/z 1045.4029 [(M+Na)$^+$; calcd for C$_{53}$H$_{71}$N$_2$O$_{13}$Na: 1045.4037].

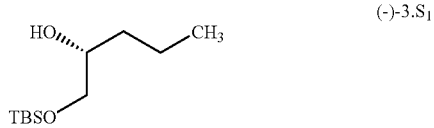

(-)-3.S$_1$

Alcohol (-)-3.S$_1$:

Dry copper(I)cyanide (23 mg, 0.259 mmol) was added to a solution of ethylmagnesium bromide (1.0M/THF) (16.2 mL, 16.2 mmol) in freshly distilled THF (26 mL) at 0° C. under argon. After stirring for five minutes, the solution was cooled to -15° C. where known epoxide (-)-3.30 (Cywin, et al. *J. Org. Chem.* 1991, 56, 2953) (2.45 g, 12.9 mmol) in freshly distilled THF (10.0 mL) was added dropwise via cannula. After stirring for fifteen minutes, the reaction mixture was poured into saturated aqueous ammonium chloride (20 mL), extracted with ethyl acetate (15 mL, 3×), dried over MgSO$_4$, filtered and concentrated in vacuo. Purification via silica gel chromatography (5% EtOAc/hexanes) afforded alcohol (-)-3.S$_1$ (2.59 g, 92%) as a colorless oil. [α]$_D^{20}$-41.7 (c 0.67, CHCl$_3$); IR (neat) 2927 (m), 1465 (s), 1254 (s), 1097 (s), 838 (s), 780 (s) cm$^{-1}$; $^1$HNMR (500 MHz, CDCl$_3$) δ 3.64 (m, 1H), 3.62 (dd, J=9.6, 2.3 Hz, 1H), 3.38 (ddd, J=8.9, 7.9, 0.7 Hz, 1H), 2.38 (br s, 1H), 1.41 (m, 4H), 0.93 (app t, J=6.8 Hz, 3H), 0.90 (s, 9H), 0.07 (s, 6H); $^{13}$CNMR (125 MHz, CDCl$_3$) δ 71.5, 67.2, 34.9, 25.8, 18.7, 18.2, 14.1, -5.3, -5.4; high resolution mass spectrum (CI, NH$_3$) m/z 219.1777 [(M)$^+$; calcd for C$_{11}$H$_{26}$O$_2$Si: 219.1701].

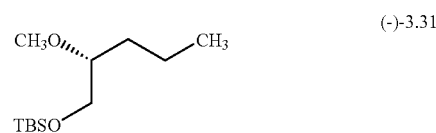

(-)-3.31

TBS Ether (-)-3.31:

To a stirred solution of (-)-3.S$_1$ (1.24 g, 5.70 mmol) in dichloromethane (9.6 mL) under argon at room temperature was added 2,6-di-tert-butyl-4-methylpyridine (2,6-DTBMP) (1.75 g, 8.50 mmol) in one portion followed by the dropwise addition of methyltrifluoromethylsulfonate (3.22 mL, 28.5 mmol). After stirring for seventeen hours at room temperature, the light brown reaction mixture was filtered through a pad of Celite followed by washing with dichloromethane (10 mL, 3×). The filtrate was washed with saturated aqueous sodium bicarbonate (20 mL) and the resultant aqueous layer was extracted with dichloromethane (15 mL, 3×). The combined organic extracts were dried over MgSO$_4$, filtered and concentrated in vacuo. Purification via silica gel chromatography (10% Et$_2$O/hexanes) afforded (-)-3.31 (0.77 g, 58%) as a colorless oil. [α]$_D^{20}$-32.6 (c 0.41, CHCl$_3$); IR (neat) 2951 (m), 2857 (s), 1463 (s), 1249 (s), 1103 (b), 842 (s), 780 (s) cm$^{-1}$; $^1$HNMR (500 MHz, CDCl$_3$) δ 3.61 (dd, J=10.5, 5.7 Hz, 1H), 3.54 (dd, J=10.5, 4.9 Hz, 1H), 3.40 (s, 3H), 3.18 (m, 1H), 1.42 (m, 4H), 0.91 (app t, J=7.1 Hz, 3H), 0.89 (s, 9H), 0.05 (s, 6H); $^{13}$CNMR (125 MHz, CDCl$_3$) δ 82.0, 65.5, 58.1, 33.8, 26.1, 18.8, 14.4, -2.7, -5.1, -5.2; high resolution mass spectrum (CI, NH$_3$) m/z 233.4439 [(M)$^+$; calcd for C$_{12}$H$_{28}$O$_2$Si: 233.4441].

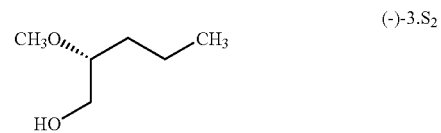

(-)-3.S$_2$

Alcohol (-)-3.S$_2$:

To a stirred solution of (-)-3.31 (0.12 g, 0.517 mmol) in freshly distilled THF (10.3 mL) at 0° C. under argon was added dropwise, tetrabutylammonium fluoride (1.0 M/THF) (0.78 mL, 0.780 mmol). After stirring for one hour, the reaction was quenched via dropwise addition of saturated aqueous sodium chloride (5 mL) and allowed to warm to room temperature. The layers of the biphasic mixture were separated and the aqueous layer was extracted with ethyl acetate (7 mL, 3×). The combined organic layers were dried over MgSO$_4$, filtered and concentrated in vacuo. Purification via silica gel chromatography (40% Et$_2$O/pentane) afforded alcohol (-)-3.S$_2$ (57.9 mg, 95%) as a colorless oil. [α]$_D^{20}$- 32.7 (c 0.49, CHCl$_3$); IR (neat) 3246 (b), 2953 (m), 1463 (s), 1378 (b), 1139 (s), 1095 (b), 1056 (s), 812 (s) cm$^{-1}$; $^1$HNMR (500 MHz, CDCl$_3$) δ 3.68 (dd, J=11.5, 3.3 Hz, 1H), 3.47 (dd, J=11.5, 6.5 Hz, 1H), 3.41 (s, 3H), 3.26 (m, 2H), 1.92 (br s, 1H), 1.56 (m, 1H), 1.38 (m, 2H), 0.94 (app t, J=7.3, 3H); $^{13}$CNMR (125 MHz, CDCl$_3$) δ 81.6, 64.2, 57.3, 32.7, 18.8, 14.5; high resolution mass spectrum (CI, NH$_3$) m/z 119.0991 [(M)$^+$; calcd for C$_6$H$_{14}$O$_2$: 119.0994].

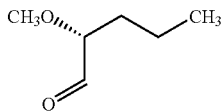

(−)-3.32

Aldehyde (−)-3.32:

To a stirred solution of (−)-3.S$_2$ (0.23 g, 1.94 mmol) in dichloromethane (98 mL) at 0° C. under argon was added, in one portion, solid sodium bicarbonate (0.41 g, 4.9 mmol) followed by portion wise addition of Dess-Martin periodinane (4.17 g, 9.80 mmol). After ten minutes, the reaction was warmed to room temperature and stirred for two hours, at which point the reaction was quenched via dropwise addition of saturated aqueous sodium bicarbonate (35 mL). The layers of the biphasic solution were separated and the aqueous layer extracted with dichloromethane (15 mL, 3×). The combined organic extracts were dried over MgSO$_4$, filtered and concentrated in vacuo. Purification via silica gel chromatography, (10% Et$_2$O/pentane) afforded (−)-3.32 (0.21 g, 91%) as an amorphous solid. [α]$_D^{20}$−34.8 (c 0.52, CHCl$_3$); IR (neat) 2925 (m), 1737 (s), 1458 (b), 1098 (b) cm−1; $^1$HNMR (500 MHz, CDCl$_3$) δ 9.65 (dd, J=1.9, 0.7 Hz, 1H), 3.56 (ddd, J=6.2, 5.4, 1.9 Hz, 1H), 3.44 (d, J=0.8 Hz, 3H), 1.63 (m, 2H), 1.43 (m, 2H), 0.93 (app t, J=7.4 Hz, 3H); $^{13}$CNMR (125 MHz, CDCl$_3$) δ 204.5, 86.0, 58.7, 32.3, 18.4, 14.3; high resolution mass spectrum (CI, NH$_3$) m/z 117.0143 [(M)$^+$; calcd for C$_6$H$_{12}$O$_2$: 117.0138].

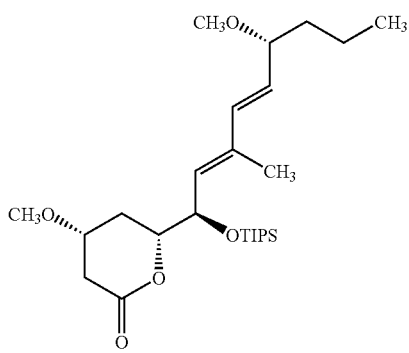

(−)-3.33

Lactone (−)-3.33:

To a solution of chromium(II)chloride (1.41 g, 11.5 mmol) in freshly distilled THF (4.5 mL) at room temperature under an argon atmosphere was added dropwise, anhydrous DMF (0.87 mL). The resultant brown solution was vigorously stirred for thirty minutes, at which point a solution of aldehyde (−)-3.32 (0.13 g, 1.12 mmol) and tributyl(dibromomethyl)stannane (Bu$_3$SnCHBr$_2$) (1.14 g, 2.50 mmol) in freshly distilled THF (4.5 mL) were added dropwise via cannula. The solution was covered with aluminum foil to preclude exposure to light. Flame dried lithium iodide (0.59 g, 4.50 mmol) in freshly distilled THF (4.5 mL) was added dropwise via syringe and the reaction mixture was stirred at room temperature. After twenty four hours, the reaction was quenched via dropwise addition of water (5 mL). The layers of the biphasic solution were separated and the aqueous layer was extracted with diethyl ether (10 mL, 3×). The combined organic layers were washed with water (5 mL), saturated aqueous sodium chloride (5 mL), dried over MgSO$_4$, filtered and concentrated in vacuo to afford a light green oil. Due to decomposition upon silica gel chromatography, 3.24 was carried on crude (78%, 20:1, E:Z by $^1$HNMR [C$_6$D$_6$] analysis of the crude isolate).

Vinyl stannane 3.24 (0.136 g, 0.34 mmol) and known vinyl iodide IX (Smith, et al. *J. Am. Chem. Soc.* 2001, 123, 10942) (0.041 g, 0.084 mmol) were combined in a round bottom flask, azeotroped from benzene (5 mL, 3×) and dried under vacuum for thirty minutes. To the flask under an argon atmosphere were added, Ph$_2$PO$_2$NBu$_4$ (0.039 g, 0.084 mmol) and tris(dibenzylideneacetone)dipalladium-chloroform adduct [Pd$_2$(dba)$_3$.CHCl$_3$] (8.7 mg, 0.0084 mmol) followed by anhydrous DMF (0.85 mL, sparged with argon, one hour). After four hours at room temperature, the reaction was purified directly via silica gel chromatography (20% EtOAc/hexanes) to afford (−)-3.33 (0.47 g, 89%) as a colorless oil. [α]$_D^{20}$−12.0 (c 0.05, CHCl$_3$); IR (neat) 2941 (b), 2868 (s), 1748 (s), 1460 (s), 1371 (b), 1240 (b), 1093 (b), 884 (s), 795 (s), 680 (s) cm$^{-1}$; $^1$HNMR (500 MHz, CDCl$_3$) δ 6.16 (d, J=15.7 Hz, 1H), 5.51 (dd, J=15.7, 7.8 Hz, 1H), 5.44 (d, J=8.8 Hz, 1H), 4.79 (dd, J=8.8, 4.7 Hz, 1H), 4.23 (ddd, J=8.5, 7.5, 3.4 Hz, 1H), 3.69 (m, 1H), 3.58 (app q, J=6.6 Hz, 1H), 3.36 (d, J=0.9 Hz, 3H), 3.26 (d, J=0.8 Hz, 3H), 2.89 (dd, J=17.2, 5.8 Hz, 1H), 2.40 (m, 2H), 1.81 (s, 3H), 1.59 (m, 2H), 1.43 (m, 1H), 1.31 (m, 2H), 1.04 (m, 21H), 0.91 (app t, J=7.2 Hz, 3H); $^{13}$CNMR (125 MHz, CDCl$_3$) δ 169.8, 136.2, 136.1, 130.6, 130.0, 82.4, 80.4, 72.7, 70.3, 56.5, 56.2, 37.9, 37.1, 29.8, 18.8, 18.1, 14.2, 13.8, 12.5; high resolution mass spectrum (ES$^+$) m/z 491.3170 [(M+Na)$^+$; calcd for C$_{26}$H$_{48}$O$_5$SiNa: 491.3168].

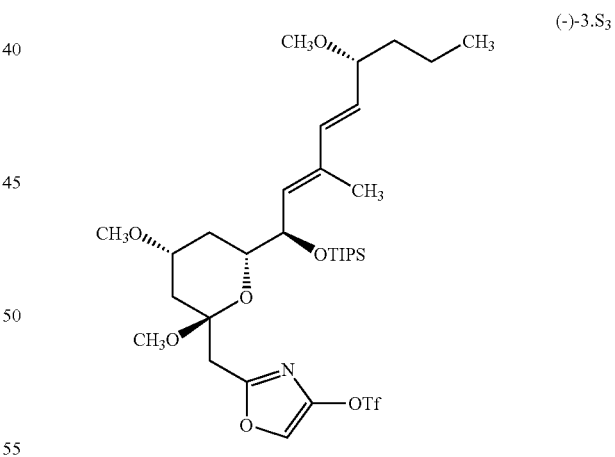

(−)-3.S$_3$

Mixed Methyl Ketal (−)-3.S$_3$:

To lactone (−)-3.33 (29.0 mg, 0.063 mmol) in a flame dried round bottom flask under argon at room temperature in freshly distilled THF (3.0 mL) was added oxazole 2.9 (0.12 g, 0.380 mmol) and the solution cooled to 0° C. iso-Propylmagnesium chloride (2.0 M/THF, 0.079 mL, 0.157 mmol) was then added dropwise over thirty minutes. After stirring for twenty minutes, another addition of iso-propylmagnesium chloride (2.0 M/THF, 0.04 mL, 0.076 mmol) was introduced over twenty minutes. After a third addition of iso-propylmagnesium chloride (0.04 mL, 0.076 mmol) and stirring for thirty minutes, the reaction was quenched via dropwise addition of saturated aqueous sodium bicarbonate (3 mL). The solution was warmed to room temperature, at which point the layers of the biphasic mixture were separated and the aqueous layer was extracted with ethyl acetate (5 mL, 3×). The combined organic extracts were dried over MgSO$_4$, filtered and concentrated in vacuo. The resultant pale yellow oil was then dissolved in anhydrous methanol (7.3 mL) followed by the addition of p-TsOH.H$_2$O (7 mg, 0.038 mmol) under an argon atmosphere. After stirring for twenty hours at room temperature, the reaction was quenched via dropwise addition of aqueous saturated sodium bicarbonate (8 mL). The biphasic mixture was extracted with ethyl acetate (5 mL, 3×) and the combined organic extracts were dried over MgSO$_4$, filtered and concentrated in vacuo. Purification via silica gel chromatography (20% EtOAc/hexanes) afforded (−)-3.S$_3$ (21.1 mg, 47%) over the two steps as a colorless oil. [α]$_D^{20}$−13.2 (c 0.61, CHCl$_3$); IR (neat) 2935 (b), 2867 (s), 1593 (s), 1433 (s), 1375 (b), 1224 (s), 1137 (s), 1098 (b), 860 (b) cm$^{-1}$; $^1$HNMR (500 MHz, CDCl$_3$) δ 7.60 (s, 1H), 6.15 (d, J=15.7 Hz, 1H), 5.47 (dd, J=15.7, 7.9 Hz, 1H), 5.38 (d, J=8.9, Hz, 1H), 4.64 (dd, J=8.9, 6.2 Hz, 1H), 3.56 (m, 3H), 3.31 (s, 3H), 3.30 (s, 3H), 3.27 (s, 3H), 3.26 (d, J=15.5 Hz, 1H), 2.99 (d, J=14.9 Hz, 1H), 2.17 (dddd, J=12.6, 4.6, 4.6, 1.5 Hz, 1H), 1.99 (dd, J=12.2, 4.3, Hz, 1H), 1.77 (d, J=0.9 Hz, 3H), 1.62 (m, 1H), 1.44 (m, 1H), 1.34 (m, 3H), 1.07 (m, 22H), 0.92 (app t, J=7.3 Hz, 3H); $^{13}$CNMR (125 MHz, CDCl$_3$) δ 159.0, 145.0, 136.6, 134.6, 132.3, 129.8, 127.1, 99.9, 82.6, 74.4, 73.6, 71.9, 56.4, 55.8, 48.1, 39.4, 37.9, 36.2, 32.3, 18.8, 18.2, 18.1, 14.2, 13.8, 12.6; high resolution mass spectrum (ES$^+$) m/z 736.3152 [(M+Na)$^+$; calcd for C$_{32}$H$_{54}$NO$_9$SSiNa: 736.3137].

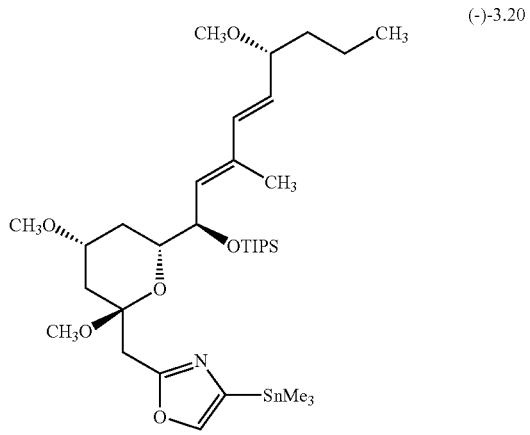

(−)-3.20

C(45-46)-Alkyl Stannane Sidechain (−)-3.20:

Oxazole triflate (−)-3.S$_3$ (42 mg, 0.059 mmol) was combined with hexamethylditin (0.017 mL, 0.082 mmol) in a sealed tube (100 mL), azeotroped from benzene (5 mL, 3×) and dried under vacuum for one hour. To the sealed tube in a glove bag under an argon atmosphere was added flame dried lithium chloride (40 mg, 0.940 mmol), tetrakis(triphenylphosphine)palladium [Pd(PPh$_3$)$_4$] (10 mg, 0.008 mmol) and anhydrous dioxane (0.60 mL, freeze pump thawed, 3×). The tube was sealed and the reaction vessel heated to 90° C. behind a blast shield. After twelve hours, the reaction was cooled to room temperature and purified directly via silica gel chromatography (15% EtOAc/hexanes) to afford (−)-3.20 (27.5 mg, 64%) as a colorless oil. [α]$_D^{20}$−14.6 (c 0.57, CH$_2$Cl$_2$); IR (neat) 2930 (s), 2870 (s), 1462 (s), 1378 (b), 1087 (b), 879 (s), 775 (b); $^1$HNMR (500 MHz, C$_6$D$_6$) δ 7.21 (s, 1H), 6.23 (d, J=15.7 Hz, 1H), 5.56 (dd, J=15.7, 7.7 Hz, 1H), 5.53 (d, J=8.4 Hz, 1H), 4.73 (dd, J=8.8, 6.3 Hz, 1H), 3.74 (m, 1H), 3.67 (m, 1H), 3.52 (app q, J=6.8 Hz, 1H), 3.46 (d, J=14.9 Hz, 1H), 3.43 (s, 3H), 3.17 (s, 3H), 3.06 (s, 3H), 3.05 (d, J=14.7 Hz, 1H), 2.57 (dddd, J=12.6, 4.5, 4.4, 1.4 Hz, 1H), 2.14 (dd, J=12.2, 2.2 Hz, 1H), 1.73 (s, 3H), 1.68 (app q, J=6.5 Hz, 1H), 1.47 (m, 2H), 1.35 (m, 3H), 1.14 (m, 21H), 0.88 (app t, J=7.3 Hz, 3H), 0.24 (s, 9H); $^{13}$CNMR (125 MHz, C$_6$D$_6$) δ 161.5, 145.4, 136.7, 135.1, 133.1, 130.9, 100.9, 82.8, 74.7, 74.2, 72.9, 56.5, 55.6, 48.3, 40.6, 38.8, 36.4, 33.2, 19.4, 18.7, 18.6, 14.6, 14.1, 13.2, −9.3; high resolution mass spectrum (ES$^+$) m/z 752.3370 [(M+Na)$^+$; calcd for C$_{34}$H$_{63}$NO$_6$SiSnNa: 752.3345].

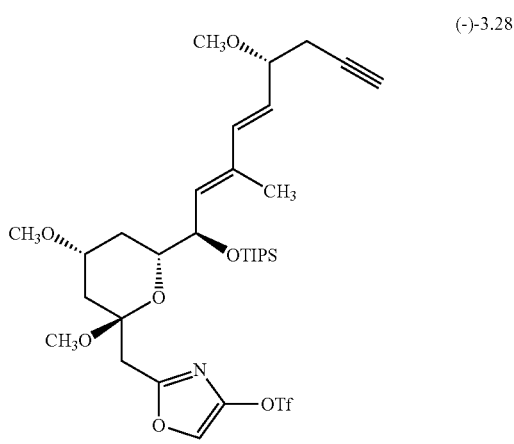

(−)-3.28

Terminal Alkyne Sidechain (−)-3.28:

To a solution of oxazole triflate (−)-2.S$_5$ (43 mg, 0.055 mmol) under an argon atmosphere in freshly distilled THF (1 mL), absolute ethanol (1 mL), and water (1 mL) was added 2,6-lutidine (0.086 ml) at room temperature. After stirring for five minutes, silver nitrate (93.0 mg, 0.550 mmol) was added as one portion. After fifteen hours, the reaction was quenched via dropwise addition of 1N potassium dihydrogenphosphate (KH$_2$PO$_4$) (5 mL). After stirring for five minutes at room temperature, the yellow biphasic mixture was poured into saturated aqueous sodium chloride (10 mL) and extracted with ethyl acetate (10 mL, 3×). The combined organic extracts were dried over MgSO$_4$, filtered and concentrated in vacuo. Purification via silica gel chromatography (30% EtOAc/hexanes) afforded terminal alkyne sidechain (−)-3.28 (35.5 mg, 91%) as a pale yellow oil. [α]$_D^{20}$−31.1 (c 0.09, CHCl$_3$); IR (neat) 2941 (b), 2868 (s), 1591 (s), 1434 (s), 1230 (s), 1141 (s), 1093 (s), 1015 (s), 858 (s), 800 (b); $^1$HNMR (500 MHz, CDCl$_3$) δ 7.60 (s, 1H), 6.25 (d, J=15.7 Hz, 1H), 5.57 (dd, J=15.6, 7.7 Hz, 1H), 5.43 (d, J=8.9 Hz, 1H), 4.61 (dd, J=8.9, 6.3 Hz, 1H), 3.79 (app q, J=6.0 Hz, 1H), 3.56 (m, 2H), 3.32 (s, 3H), 3.31 (s, 3H), 3.30 (s, 3H), 3.25 (d, J=14.9 Hz, 1H), 2.98 (d, J=14.9 Hz, 1H), 2.49 (m, 2H), 2.17 (dddd, J=12.6, 4.6, 4.5, 1.7, Hz, 1H), 1.99 (app t, J=2.6Hz, 1H), 1.78 (d, J=1.1 Hz, 3H), 1.37 (dd, J=12.6, 11.1 Hz, 1H), 1.06 (m, 23H); $^{13}$CNMR (125 MHz, CDCl$_3$) δ 158.9, 144.9, 137.7, 134.4, 133.2, 127.5, 127.1, 99.9, 80.8, 80.6, 74.3, 73.5, 71.8, 70.1, 56.8, 55.8, 48.2, 39.3, 36.1, 32.2, 25.9, 18.2, 18.1, 13.8, 12.6; high resolution mass spectrum (ES$^+$) m/z 732.2795 [(M+Na)$^+$; calcd for C$_{32}$H$_{50}$F$_3$NO$_9$SSiNa: 732.2826].

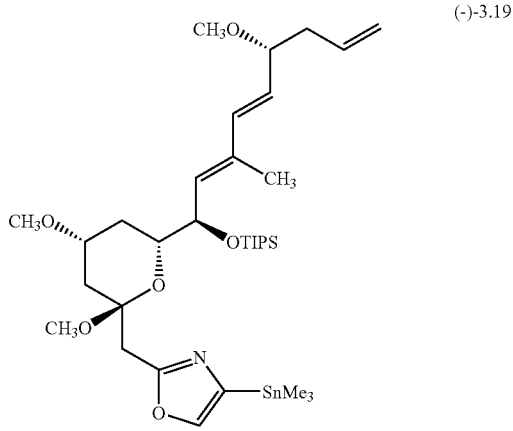

(−)-3.19

C(45-46)-Alkenyl Stannane Sidechain (−)-3.19:

To a stirring solution of alkyne (−)-3.28 (37.0 mg, 0.052 mmol) in acetone (3.5 mL) and 1-hexene (3.5 mL) at room temperature under an argon atmosphere were added quinoline (0.061 ml, 0.520 mmol), and Lindlar's catalyst (5% Pd/CaCO$_3$, poisoned with Pb) (20 mg, 0.010 mmol). Under vigorous stirring, the reaction vessel was fitted with a hydrogen balloon and stirred at room temperature. After three hours, the reaction was quenched with 1N hydrogen chloride solution (5 mL) and allowed to stir for one minute. The biphasic solution was filtered through a pad of Celite, and washed with acetone (10 mL, 3×). The layers of the biphasic mixture were separated and the aqueous layer was extracted with ethyl acetate (10 mL, 3×). The combined organic extracts were dried over MgSO$_4$, filtered and concentrated under reduced pressure. Crude C(45-46)-alkene 3.27 (27 mg, 0.038 mmol) was then combined with hexamethylditin (0.011 mL, 0.053 mmol) in a sealed tube (100 mL), azeotroped from benzene (5 mL, 3×) and dried under vacuum for one hour. In a glove bag under an inert argon atmosphere was added flame dried lithium chloride (25 mg, 0.600 mmol), tetrakis(triphenylphosphine)palladium [Pd(PPh$_3$)$_4$] (6 mg, 0.006 mmol) and dioxane (0.5 mL, freeze pump thawed, 3×). The tube was sealed and heated to 90° C. behind a blast shield. After fifteen hours, the reaction was cooled to room temperature and the reaction mixture was introduced directly onto a silica gel column, (15% EtOAc/hexanes) to afford (−)-3.19 (26.4 mg, 69%, 2-steps) as a colorless oil. $[\alpha]_D^{20}$ −12.6 (c 0.92, CH$_2$Cl$_2$); IR (neat) 2935 (s), 2867 (s), 1559 (s), 1457 (s), 1300 (b), 1093 (s), 966 (s), 882 (s), 775 (b) cm$^{-1}$; $^1$HNMR (500 MHz, C$_6$D$_6$) δ 7.21 (s, 1H), 6.21 (d, J=15.7 Hz, 1H), 5.90 (m, 1H), 5.54 (dd, J=15.7, 7.7 Hz, 1H), 5.51 (d, J=7.2 Hz, 1H), 5.06 (s, 1H), 5.04 (d, J=2.0 Hz, 1H), 4.72 (dd, J=8.8, 6.3 Hz, 1H), 3.73 (dd, J=10.2, 6.2 Hz, 1H), 3.67 (m, 1H), 3.55 (dd, J=13.6, 6.5 Hz, 1H), 3.44 (d, J=18.2 Hz, 1H), 3.42 (s, 3H), 3.13 (s, 3H), 3.05 (s, 3H), 3.04 (d, J=12.7 Hz, 1H), 2.56 (dd, J=12.7, 3.0 Hz, 1H), 2.43 (m, 1H), 2.28 (m, 1H), 2.12 (d, J=10.0 Hz, 1H), 1.71 (s, 3H), 1.67 (app t, J=12.6 Hz, 1H), 1.30 (app q, J=11.9 Hz, 1H), 1.13 (m, 21 H), 0.24 (s, 9H); $^{13}$CNMR (125 MHz, C$_6$D$_6$) δ 161.7, 145.6, 138.6, 137.2, 135.7, 135.1, 133.5, 130.2, 117.3, 101.1, 82.8, 74.9, 74.4, 73.1, 56.6, 55.8, 48.5, 41.3, 40.7, 36.6, 33.4, 18.8, 18.7, 14.3, 13.4; high resolution mass spectrum (ES$^+$) m/z 750.3220 [(M+Na)$^+$; calcd for C$_{34}$H$_{61}$NO$_6$SiSnNa: 750.3213].

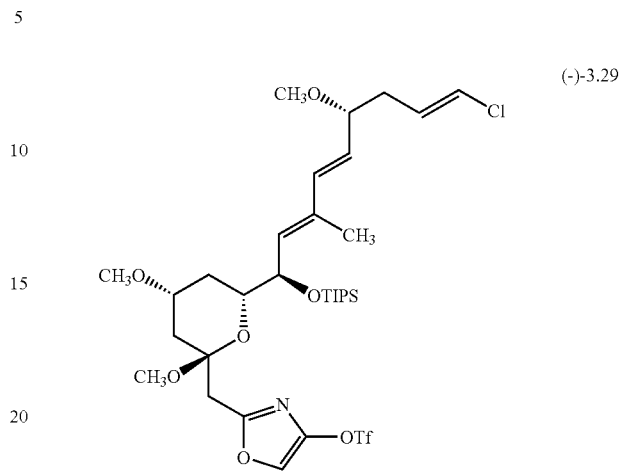

(−)-3.29

C(45-46)-E-Chloroalkene (−)-S$_5$:

To a solution of terminal alkyne (−)-3.28 (32 mg, 0.045 mmol) in anhydrous benzene (1.3 mL) at room temperature under an argon atmosphere was added 2,2'-azobis(2-methylpropionitrile) (AIBN) (1 mg, 0.009 mmol) in one portion, followed by the dropwise addition of tri-n-butyltin hydride (0.024 ml, 0.09 mmol) and the reaction was heated to 85° C. After four hours, the reaction was cooled to room temperature, diluted with dichloromethane (3 mL) and concentrated in vacuo. The resultant crude vinyl stannane (26 mg, 0.026 mmol), as a colorless oil, was then dissolved in freshly distilled THF (1 mL). Copper(II)chloride (8 mg, 0.057 mmol) was added in one portion and the resultant yellow solution was stirred at room temperature under an argon atmosphere. After fifteen hours, the reaction was quenched via dropwise addition of saturated aqueous sodium bicarbonate (5 mL). The layers of the resultant biphasic mixture were separated and the aqueous layer was extracted with dichloromethane (5 mL, 4×). The combined organic extracts were dried over MgSO$_4$, filtered and concentrated in vacuo. Purification via silica gel chromatography, (25% EtOAc/hexanes) afforded C(45-46)-E-chloroalkene (+)-3.29 (21.5 mg, 64%, 13:1, E:Z, 2 steps) as a colorless oil. $[\alpha]_D^{20}$ −31.3 (c 0.41, CHCl$_3$); IR (neat) 2942 (b), 2864 (s), 1594 (s), 1432 (s), 1231 (s), 1138 (s), 1094 (b), 854 (b); $^1$HNMR (500 MHz, CDCl$_3$) δ 7.60 (s, 1H), 6.17 (d, J=15.7 Hz, 1H), 6.00 (d, J=13.3 Hz, 1H), 5.89 (m, 1H), 5.45 (dd, J=15.7, 7.8 Hz, 1H), 5.42 (d, J=9.4 Hz, 1H), 4.60 (dd, J=8.8, 6.2 Hz, 1H), 3.64 (app q, J=6.5 Hz, 1H), 3.56 (m, 2H), 3.31 (s, 3H), 3.30 (s, 3H), 3.27 (s, 3H), 3.25 (d, J=14.9 Hz, 1H), 2.98 (d, J=14.9 Hz, 1H), 2.37 (m, 1H), 2.27 (m, 1H), 2.17 (dd, J12.6, 3.5 Hz, 1H), 1.99 (ddd, J=10.0, 4.2, 2.1 Hz, 1H), 1.76 (s, 3H), 1.38 (d, J=12.3 Hz, 1H), 1.36 (d, J=11.4 Hz, 1H), 1.06 (m, 21H); $^{13}$CNMR (125 MHz, CDCl$_3$) δ 159.0, 145.0, 137.4, 134.3, 133.1, 129.8, 128.3, 127.1, 119.1, 99.9, 81.7, 74.3, 73.5, 71.8, 56.5, 55.7, 48.1, 39.3, 37.4, 36.1, 32.2, 18.2, 18.1, 13.8, 12.6; high resolution mass spectrum (ES$^+$) m/z 769.3469 [(M+Na)$^+$; calcd for C$_{32}$H$_{51}$F$_3$NO$_9$SSiClNa: 769.3474].

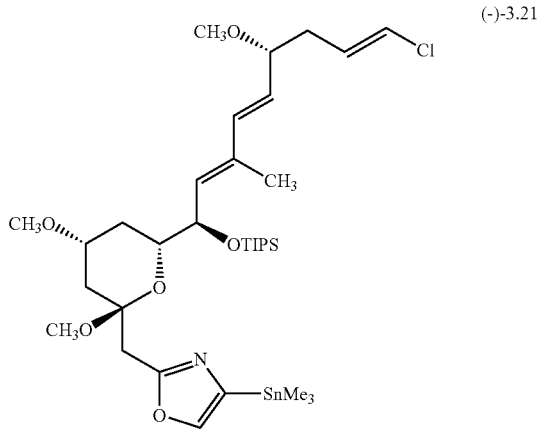

(−)-3.21

C(45-46)-E-Chloroalkenyl Stannane Sidechain (−)-3.21:

C(45-46)-E-chloroalkene (−)-3.29 (0.42 g, 0.059 mmol) was combined with hexamethylditin (0.017 mL, 0.082 mmol) in a sealed tube (100 mL), azeotroped from benzene (5 mL, 3×) and dried for one hour under vacuum. In a glove bag under an inert argon atmosphere was added flame dried lithium chloride (39 mg, 0.941 mmol) followed by tetrakis(triphenylphosphine)palladium [Pd(PPh$_3$)$_4$] (10 mg, 0.009 mmol) and dioxane (0.6 mL, freeze pump thawed, 3×). The tube was sealed and the reaction mixture heated to 80° C. behind a blast shield. After twelve hours, the reaction was cooled to room temperature and introduced directly onto a silica gel column, (15% EtOAc/hexanes) to afford C(45-46)-E-chloroalkene stannane sidechain (−)-3.21 (30.5 mg, 68%) as a colorless oil. [α]$_D^{20}$−28.4 (c 0.32, CH$_2$Cl$_2$); IR (neat) 2940 (s), 2863 (s), 1556 (s), 1460 (s), 1378 (b), 1244 (s), 1095 (b), 990 (s), 883 (s), 773 (s), 681 (s); $^1$HNMR (500 MHz, C$_6$D$_6$) δ 7.21 (s, 1H) 6.12 (d, J=15.7 Hz, 1H), 5.90 (ddd, J=13.3, 7.5, 7.4 Hz, 1H), 5.69 (d, J=13.3 Hz, 1H), 5.51 (d, J=8.9 Hz, 1H), 5.38 (dd, J=15.7, 7.8 Hz, 1H), 4.72 (dd, J=8.8, 6.3 Hz, 1H), 3.74 (m, 1H), 3.66 (m, 1H), 3.45 (d, J=14.9 Hz, 1H), 3.43 (s, 3H), 3.35 (app q, J=6.4 Hz, 1H), 3.06 (s, 3H), 3.03 (s, 3H), 2.56 (dd, J=12.7 3.0 Hz, 1H), 2.12 (m, 2H), 1.99 (app q, J=6.1 Hz, 1H), 1.68 (s, 3H), 1.30 (dd, J=23.6, 11.9 Hz, 2H), 1.14 (m, 22H), 0.24 (s, 9H); $^{13}$CNMR (125 MHz, C$_6$D$_6$) δ 161.5, 145.4, 137.5, 134.7, 133.8, 130.5, 129.3, 119.5, 100.9, 81.9, 74.7, 74.2, 72.8, 56.4, 55.6, 48.3, 40.5, 37.8, 36.4, 33.2, 18.7, 18.6, 14.1, 13.2, −9.3; high resolution mass spectrum (ES$^+$) m/z 784.2787 [(M+Na)$^+$; calcd for C$_{34}$H$_{60}$ClNO$_6$SiSnNa: 784.2645].

Protected C(45-46)-TMS-Alkynyl-Phorboxazole (+)-3.35:

Vinyliodide macrocycle (+)-2.5 (13.8 mg, 0.017 mmol) and C(45-46)-TMS-alkyne stannane sidechain (−)-2.90 (21.0 mg, 0.026 mmol) were combined in a flame dried round bottom flask (5 mL), azeotroped from benzene (2 mL, 3×) and dried under vacuum for two hours. To the flask under an argon atmosphere was added tris(dibenzylideneacetone)dipalladium-chloroform adduct [Pd$_2$(dba)$_3$·CHCl$_3$] (3.6 mg, 0.003 mmol), triphenylarsine (AsPh$_3$) (6.4 mg, 0.021 mmol) and Ph$_2$PO$_2$NBu$_4$ (12 mg, 0.026 mmol) followed by introduction of DMF (0.17 mL, sparged with argon, thirty minutes) and diisopropylethylamine (0.003 mL, 0.017 mmol). After the reaction was allowed to stir for sixteen hours at room temperature, the light brown reaction mixture was introduced directly onto a silica gel column, (20% EtOAc/hexanes→30% EtOAc/hexanes) to afford protected C(45-46)-TMS-alkynyl-phorboxazole (+)-3.35 (14.9 mg, 68%) as a light yellow oil. [α]$_D^{20}$+1.36 (c 0.22, CHCl$_3$); IR (neat) 2925.8 (b), 1718 (s), 1456 (b), 1250 (s), 1187 (s), 1091 (s), 1053 (b), 840 (s) cm$^{-1}$; $^1$HNMR (500 MHz, C$_6$D$_6$) δ 6.96 (s, 1H), 6.90 (m, 1H), 6.37 (s, 1H), 6.32 (d, J=15.7 Hz, 1H), 6.20 (d, J=15.9 Hz, 1H), 5.79 (dd, J=11.2, 2.3 Hz, 1H), 5.69 (dd, J=15.7, 7.3 Hz, 1H), 5.57 (d, J=8.9 Hz, 1H), 5.47 (ddd, J=10.7, 10.5, 2.9 Hz, 1H), 5.18 (s, 1H), 4.96 (dd, J=11.3, 2.0 Hz, 1H), 4.77 (m, 2H), 4.62 (dd, J=11.2, 4.4 Hz, 1H), 4.39 (m, 1H), 4.25 (app t, J=10.4 Hz, 1H), 4.08 (m, 1H), 4.03 (d, J=2.6 Hz, 1H), 3.95 (m, 1H), 3.76 (m, 1H), 3.69 (app t, J=6.9 Hz, 1H), 3.68 (m, 1H), 3.52 (dd, J=9.4, 4.6 Hz, 1H), 3.45 (d, J=10.1 Hz, 1H), 3.41 (s, 3H), 3.34 (d, J=14.7 Hz, 1H), 3.28 (app t, J=4.8 Hz, 1H), 3.23 (app t, J=5.0 Hz, 1H), 3.09 (s, 3H), 3.08 (s, 3H), 3.04 (d, J=11.4 Hz, 1H), 2.95 (d, J=14.8 Hz, 1H), 2.66 (app t, J=6.3 Hz, 1H), 2.60 (m, 1H), 2.58 (dd, J=16.7, 5.7 Hz, 1H), 2.44 (dd, J=16.7, 6.8 Hz, 1H), 2.42 (m, 2H), 2.37 (dd, J=12.8, 5.5 Hz, 1H), 2.17 (dd, J=10.0, 7.7 Hz, 1H), 2.10 (m, 1H), 2.09 (d, J=0.6 Hz, 3H), 2.02 (d, J=11.8 Hz, 1H), 1.98 (d, J=13.0 Hz, 1H), 1.77 (d, J=0.8 Hz, 3H), 1.65 (m, 3H), 1.49 (d, J=13.2 Hz, 1H), 1.35 (m, 3H), 1.17 (m, 22H), 1.05 (d, J=6.9 Hz, 3H), 0.94 (s, 9H), 0.77 (d, J=6.5 Hz, 3H), 0.24 (s, 9H), 0.03 (s, 3H), 0.01 (s, 3H); $^{13}$CNMR(125 MHz, C$_6$D$_6$) δ 165.8, 161.7, 160.0, 145.5, 143.8, 143.0, 139.2, 138.2, 137.3, 136.8, 135.0, 134.4, 133.8, 133.5, 121.4, 120.1, 119.5, 110.5, 104.6, 100.8, 90.0, 86.8, 81.0, 80.2, 78.7, 74.7, 74.1, 73.7, 72.7, 69.9, 69.3, 67.7, 65.9, 56.7, 55.6, 48.3, 42.4, 40.5, 40.4, 40.0, 37.9, 36.4, 36.3, 34.9, 33.1, 32.4, 31.2, 30.5, 27.9, 26.3, 18.7, 18.6, 14.6, 14.1, 13.7, 13.2, 6.6, 1.7, 0.6, −4.5, −4.4;high resolution mass spectrum (ES$^+$) m/z 1321.7641 [(M+Na)$^+$; calcd for C$_{72}$H$_{114}$N$_2$O$_{13}$Si$_3$Na: 1321.7626].

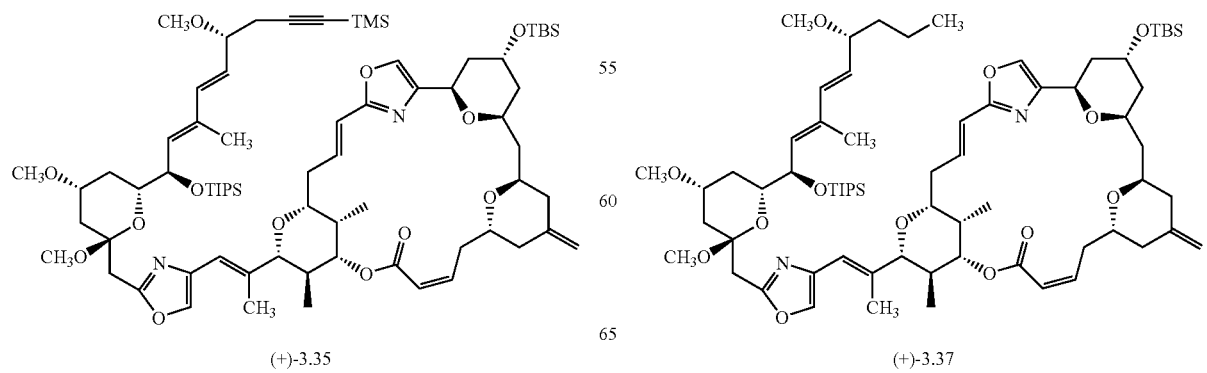

(+)-3.35    (+)-3.37

Protected C(45-46)-Alkyl-Phorboxazole (+)-3.37:

To a flame dried round bottom flask (5 mL), vinyl iodide macrocycle (+)-2.5 (10.7 mg, 0.013 mmol) was combined with the C(45-46)-alkyl side chain (−)-3.20 (14.7 mg, 0.020 mmol), azeotroped from benzene (3 mL, 3×) and dried under vacuum. After two hours, under an argon atmosphere, tris(dibenzylideneacetone)dipalladium-chloroform adduct [$Pd_2(dba)_3 \cdot CHCl_3$] (2.8 mg, 0.0027 mmol), triphenylarsine ($AsPh_3$) (4.9 mg, 0.016 mmol) and $Ph_2PO_2NBu_4$ (9.3 mg, 0.020 mmol) were added followed by anhydrous DMF (0.14 mL, sparged with argon, one hour) and diisopropylethylamine (0.002 mL, 0.014 mmol). After two minutes, the black solution turned light brown and was stirred at room temperature. After sixteen hours, the light brown reaction mixture was purified directly via silica gel chromatography, (25% EtOAc/hexanes) to afford protected C(45-46)-alkyl-phorboxazole (+)-3.37 (13.5 mg, 82%) as an off white foam. $[\alpha]_D^{20}$ −7.3 (c 0.65, $CHCl_3$); IR (neat) 2930 (s), 2865 (s), 1717 (s), 1459 (b 1382 (b), 1188 (s), 1095 (s), 1055 (b), 881 (s), 837 (s); $^1$HNMR (500 MHz, $C_6D_6$) δ 7.14 (s, 1H), 6.95 (s, 1H), 6.89 (m, 1H), 6.36 (s, 1H), 6.24 (d, J=15.7 Hz, 1H), 6.18 (d, J=15.9 Hz, 1H), 5.78 (dd, J=11.1, 2.5 Hz, 1H), 5.57 (dd, J=11.1, 2.5 Hz, 1H), 5.54 (d, J=9.1 Hz, 1H), 5.43 (ddd, J=10.7, 10.7, 2.6 Hz, 1H), 5.19 (s, 1H), 4.95 (d, J=11.2 Hz, 1H), 4.74 (m, 2H), 4.61 (dd, J=15.5, 4.3 Hz, 1H), 4.39 (br s, 1H), 4.24 (app t, J=10.3 Hz, 1H), 4.07 (m, 1H), 4.01 (d, J=2.8 Hz, 1H), 3.96 (m, 1H), 3.77 (dd, J=6.2, 1.7 Hz, 1H), 3.71 (m, 1H), 3.52 (dd, J=12.7, 6.8 Hz, 1H), 3.43 (d, J=12.6 Hz, 1H), 3.41 (s, 3H), 3.39 (m, 2H), 3.35 (d, J=14.8 Hz, 1H), 3.17 (s, 3H), 3.06 (s, 3H), 2.94 (d, J=14.8 Hz, 1H), 2.65 (app t, J=5.7 Hz, 1H), 2.57 (dd, J=12.7, 3.5 Hz, 1H), 2.39 (m, 4H), 2.17 (dd, J=10.1, 7.9 Hz, 1H), 2.08 (s, 3H), 2.04 (m, 2H), 1.97 (app t, J=14.2 Hz, 1H), 1.74 (s, 3H), 1.65 (m, 3H), 1.48 (m, 3H), 1.37 (m, 4H), 1.15 (m, 23H), 1.04 (d, J=6.8Hz, 3H), 0.92 (s, 9H), 0.89 (app t, J=7.3 Hz, 3H), 0.76 (d, J=6.4 Hz, 3H), 0.01 (s, 3H), −0.01 (s, 3H); $^{13}$CNMR (125 MHz, $C_6D_6$) δ 165.9, 161.9, 160.2, 145.8, 144.0, 143.2, 139.4, 138.4, 137.0, 136.9, 135.3, 134.5, 134.0, 133.2, 131.1, 121.6, 120.4, 119.7, 110.7, 101.0, 90.2, 83.0, 80.4, 78.9, 74.9, 74.4, 73.9, 72.9, 70.1, 69.4, 67.9, 66.1, 56.7, 55.8, 48.5, 42.6, 40.7, 40.6, 40.2, 39.0, 38.1, 36.5, 35.1, 33.4, 33.3, 32.6, 31.3, 30.7, 26.6, 26.5, 19.6, 18.9, 18.7, 14.8, 14.3, 13.9, 13.3, 6.8, −4.2, −4.3; high resolution mass spectrum (ES$^+$) m/z 1253.7355 [(M+Na)$^+$; calcd for $C_{69}H_{110}N_2O_{13}Si_2Na$: 1253.7442].

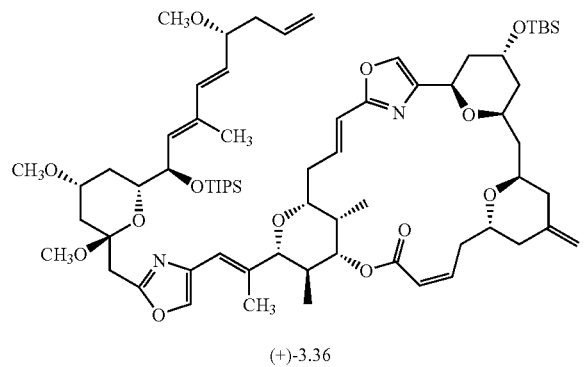

(+)-3.36

Protected C(45-46)-Alkenyl-Phorboxazole (+)-3.36:

In a flame dried round bottom flask (5 mL), vinyl iodide macrocycle (+)-2.5 (7.0 mg, 0.009 mmol) and C(45-46)-alkenyl sidechain (−)-3.19 (9.6 mg, 0.013 mmol) were combined, azeotroped from benzene (3 mL, 3×) and dried under reduced pressure. After one hour, under an inert argon atmosphere, tris(dibenzylideneacetone)dipalladium-chloroform adduct [$Pd_2(dba)_3 \cdot CHCl_3$] (1.8 mg, 0.0017 mmol), triphenylarsine ($AsPh_3$) (3.2 mg, 0.011 mmol) and $Ph_2PO_2NBu_4$ (6.1 mg, 0.013 mmol) were added followed by anhydrous DMF (0.1 mL, sparged with argon, one hour), and diisopropylethylamine (0.001 mL, 0.009 mmol). After one minute, the black solution turned light brown and was stirred at room temperature. After sixteen hours, the reaction mixture was purified directly via silica gel chromatography, (20% EtOAc/hexanes) to afford protected C(45-46)-alkenyl-phorboxazole (+)-3.36 (8.4 mg, 77%) as an off white foam. $[\alpha]_D^{20}$ +7.4 (c 0.17, $CHCl_3$); IR (neat) 2989 (b), 2865 (s), 1721 (s), 1646 (b), 1463 (b), 1384 (b), 1252 (b), 1187 (s), 1098 (s), 1061 (b) cm$^{-1}$; $^1$HNMR (500 MHz, $C_6D_6$) δ 7.12 (s, 1H), 6.95 (s, 1H), 6.88 (m, 1H), 6.35 (s, 1H), 6.22 (d, J=16.1 Hz, 1H), 6.19 (d, J=17.4 Hz, 1H), 5.91 (m, 1H), 5.78 (d, J=11.2 Hz, 1H), 5.56 (dd, J=15.7, 7.6 Hz, 1H), 5.53 (d, J=7.8 Hz, 1H), 5.45 (app t, J=10.5 Hz, 1H), 5.17 (s, 1H), 5.06 (d, J=12.2 Hz, 1H), 4.94 (d, J=10.1 Hz, 1H), 4.74 (s, 1H), 4.61 (dd, J=11.2, 4.2 Hz, 1H), 4.38 (br s, 1H), 4.25 (app t, J=10.6 Hz, 1H), 4.06 (br s, 1H), 4.02 (s, 1H), 3.94 (m, 1H), 3.75 (m, 1H), 3.69 (m, 1H), 3.57 (app q, J=6.6 Hz, 1H), 3.44 (d, J=10.0 Hz, 1H), 3.41 (s, 3H), 3.34 (d, J=14.8 Hz, 1H), 3.14 (s, 3H), 3.07 (s, 3H), 3.06 (m, 1H), 2.95 (d, J=14.8 Hz, 1H), 2.65 (br s, 1H), 2.56 (d, J=12.4 Hz, 1H), 2.41 (m, 5H), 2.30 (m, 2H), 2.16 (d, J=10.1 Hz, 2H), 2.08 (s, 3H), 1.74 (s, 3H), 1.64 (m, 4H), 1.48 (d, J=13.6 Hz, 1H), 1.34 (m, 6H), 1.17 (m, 22H), 1.04 (d, J=6.8 Hz, 3H), 0.93 (s, 9H), 0.76 (d, J=6.4 Hz, 3H), 0.01 (s, 3H), −0.01 (s, 3H); $^{13}$CNMR (125 MHz, $C_6D_6$) δ 165.8, 161.7, 160.0, 145.5, 143.8, 143.0, 139.2, 138.2, 136.9, 136.8, 135.5, 135.0, 134.5, 133.8, 133.2, 130.1, 121.4, 120.1, 119.5, 117.2, 110.5, 100.9, 90.0, 82.6, 80.3, 78.8, 74.7, 74.2, 73.8, 72.8, 69.9, 69.3, 67.7, 65.9, 56.4, 55.6, 48.3, 42.4, 41.1, 40.5, 40.5, 40.0, 37.9, 36.4, 36.3, 34.9, 33.1, 32.4, 31.2, 30.5, 26.3, 18.7, 18.6, 14.6, 14.1, 13.7, 13.2, 6.6, −4.4, −4.5; high resolution mass spectrum (ES$^+$) m/z 1251.7268 [(M+Na)$^+$; calcd for $C_{69}H_{108}N_2O_{13}Si_2Na$: 1251.7286].

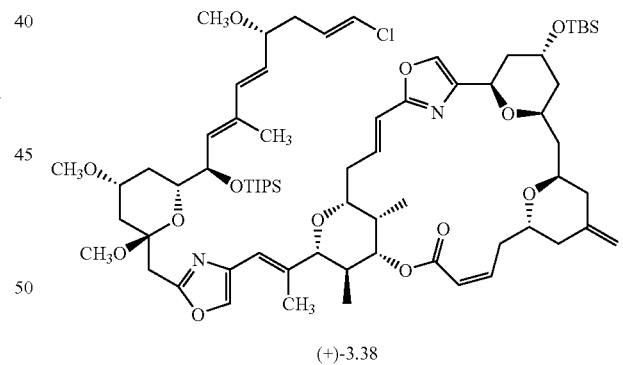

(+)-3.38

Protected C(45-46)-E-Chloroalkenyl-Phorboxazole (+)-3.38:

In a round bottom flask (5 mL), vinyl iodide macrocycle (+)-2.5 (11.4 mg, 0.014 mmol) and C(45-46)-E-chloroalkene side chain (−)-3.21 (16.4 mg, 0.021 mmol) were combined, azeotroped from benzene (3 mL, 3×) and dried under vacuum. After one hour, under an inert argon atmosphere, tris(dibenzylideneacetone)dipalladium-chloroform adduct [$Pd_2(dba)_3 \cdot CHCl_3$] (2.9 mg, 0.0028 mmol), triphenylarsine ($AsPh_3$) (5.3 mg, 0.017 mmol) and $Ph_2PO_2NBu_4$ (9.9 mg, 0.021 mmol) were added followed by anhydrous DMF (0.14 mL, sparged with argon, one hour), and diisopropylethylamine (0.002 mL, 0.014 mmol). After one minute, the black solution turned light brown and was allowed to stir at room temperature. After seventeen hours, the light brown solution was purified directly via silica gel chromatography (20% EtOAc/hexanes→25% EtOAc/hexanes) to afford protected C(45-46)-E-chloroalkenyl-phorboxazole (+)-3.38 (15.8 mg, 87%) as an off white foam. $[\alpha]_D^{20}$+14.3 (c 0.37, CHCl$_3$); IR (neat) 2933 (s), 2866 (s), 1716 (s), 1644 (b), 1461 (b), 1370 (b), 1254 (s), 1187 (s), 1153 (s), 1096 (s), 1043 (b), 879 (s), 836 (s), 807 (b) cm$^{-1}$; $^1$HNMR (500 MHz, C$_6$D$_6$) δ 7.15 (s, 1H), 6.96 (s, 1H), 6.87 (m, 1H), 6.35 (s, 1H), 6.19 (d, J=15.8 Hz, 1H), 6.14 (d, J=15.8 Hz, 1H), 5.91 (m, 1H), 5.79 (dd, J=1 1.5, 2.9 Hz, 1H), 5.70 (d, J=13.3 Hz, 1H), 5.53 (d, J=8.6 Hz, 1H), 5.45 (ddd, J=10.6, 10.6, 2.8 Hz, 1H), 5.41 (dd, J=15.7, 7.7 Hz, 1H), 5.17 (s, 1H), 4.94 (d, J=11.2 Hz, 1H), 4.73 (m, 2H), 4.61 (dd, J=11.2, 4.4 Hz, 1H), 4.38 (br s, 1H), 4.24 (app t, J=10.7 Hz, 1H), 4.06 (m, 1H), 4.02 (s, 1H), 3.94 (m, 1H), 3.77 (dd, J=6.1, 1.9 Hz, 1H), 3.69 (m, 1H), 3.43 (d, J=10.0 Hz, 1H), 3.40 (s, 3H), 3.37 (d, J=6.7 Hz, 1H), 3.33 (d, J=14.8 Hz, 1H), 3.07 (s, 3H), 3.04 (s, 3H), 2.94 (d, J=14.8 Hz, 1H), 2.64 (app t, J=5.8 Hz, 1H), 2.56 (dd, J=13.0, 4.4 Hz, 1H), 2.39 (m, 3H), 2.13 (m, 2H), 2.08 (s, 3H), 2.00 (m, 3H), 1.70 (s, 3H), 1.63 (m, 2H), 1.48 (d, J=13.2 Hz, 1H), 1.32 (m, 5H), 1.14 (m, 25H), 1.03 (d, J=6.8 Hz, 3H), 0.92 (s, 9H), 0.76 (d, J=6.4 Hz, 3H), 0.01 (s, 3H), −0.01 (s, 3H); $^{13}$CNMR (125 MHz, C$_6$D$_6$) δ 165.9, 161.8, 160.2, 145.8, 144.0, 143.2, 139.4, 138.4, 137.7, 136.9, 134.9, 134.5, 134.0, 133.9, 130.7, 121.6, 120.4, 120.1, 119.7, 119.6, 110.7, 101.0, 90.2, 82.1, 81.6, 80.4, 78.9, 74.9, 74.3, 73.9, 72.9, 70.1, 69.4, 67.9, 66.1, 56.6, 55.8, 48.5, 42.6, 40.7, 40.6, 40.1, 38.1, 38.0, 36.5, 35.1, 33.3, 32.6, 31.3, 30.7, 26.5, 18.9, 18.7, 14.8, 14.2, 13.9, 13.3, 6.8, −4.2, −4.3; high resolution mass spectrum (ES$^+$) m/z 1285.7001 [(M+Na)$^+$; calcd for C$_{69}$H$_{107}$ClN$_2$O$_{13}$Si$_2$Na: 1285.6997].

to afford protected E-C(2-3)-C(45-46)-alkynyl-phorboxazole (+)-3.39 (9.7 mg, 66%) as an off white foam. $[\alpha]_D^{20}$+ 10.6 (c 0.31, CHCl$_3$); IR (neat) 2936 (b), 1718 (s), 1653 (s), 1464 (b), 1351 (b), 1250 (s), 1151 (s), 1087 (s), 843 (s) cm$^{-1}$; $^1$HNMR (500 MHz, C$_6$D$_6$) δ 7.13 (s, 1H), 6.92 (s, 1H), 6.89 (m, 1H), 6.30 (d, J=15.7 Hz, 1H), 6.27 (s, 1H), 6.14 (d, J=16.0 Hz, 1H), 6.04 (d, J=15.2 Hz, 1H), 5.67 (dd, J=15.7, 7.3 Hz, 1H), 5.55 (d, J=8.9 Hz, 1H), 5.08 (dd, J=10.8, 3.7 Hz, 1H), 4.95 (d, J=11.7 Hz, 1H), 4.75 (dd, J=8.7, 6.1 Hz, 1H), 4.68 (s, 1H), 4.59 (s, 1H), 4.34 (br s, 1H), 4.00 (s, 1H), 3.92 (br s, 1H), 3.75 (dd, J=11.7, 6.1 Hz, 1H), 3.68 (m, 2H), 3.42 (m, 3H), 3.39 (s, 3H), 3.37 (d, J=9.8 Hz, 1H), 3.31 (d, J=14.9 Hz, 1H), 3.08 (s, 3H), 3.07 (s, 3H), 2.92 (d, J=14.7 Hz, 1H), 2.83 (br s, 1H), 2.57 (dd, J=16.7, 5.7 Hz, 1H), 2.56 (m, 1H), 2.47 (br s, 1H), 2.43 (dd, J=16.8, 6.8 Hz, 1H), 2.26 (m, 2H), 2.13 (m, 4H), 2.05 (s, 3H), 1.90 (d, J=12.6 Hz, 1H), 1.82 (d, J=13.6 Hz, 1H), 1.75 (s, 3H), 1.67 (m, 5H), 1.33 (m, 4H), 1.15 (m, 21H), 0.96 (s, 9H), 0.84 (app t, J=7.4 Hz, 6H), 0.23 (s, 9H), 0.00 (s, 3H), −0.01 (s 3H); $^{13}$CNMR (125 MHz, C$_6$D$_6$) δ 167.5, 162.6, 160.1, 147.5, 143.8, 142.8, 139.5, 138.5, 137.5, 136.9, 135.2, 134.5, 134.1, 133.8, 132.4, 130.1, 128.0, 124.3, 119.4, 119.1, 111.4, 104.8, 101.0, 86.9, 81.2, 79.3, 77.3, 74.9, 74.3, 72.9, 71.0, 66.4, 66.2, 59.2, 59.1, 56.9, 55.8, 48.4, 41.3, 40.6, 40.4, 38.8, 38.6, 38.4, 36.5, 35.6, 33.2, 30.7, 28.0, 26.5, 24.6, 20.5, 19.0, 18.9, 18.8, 14.7, 14.4, 14.3, 13.4, 0.84, −4.2; high resolution mass spectrum (ES$^+$) m/z 1321.7463 [(M+Na)$^+$; calcd for C$_{72}$H$_{114}$N$_2$O$_{13}$Si$_3$: 1321.7524].

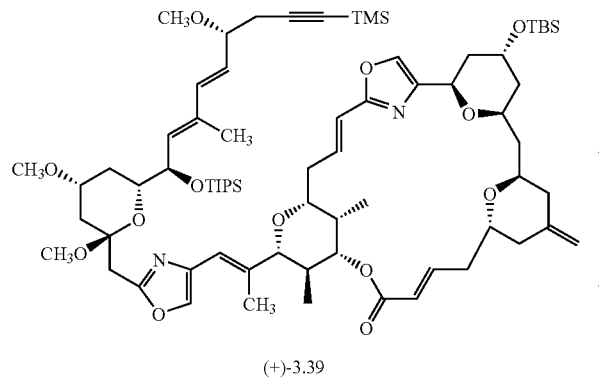

(+)-3.39

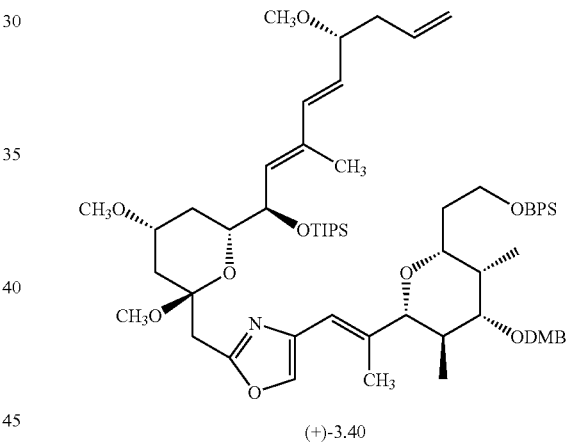

(+)-3.40

Protected C(45-46)-Alkenyl-C(22-26)-Central Tetrahydropyran (+)-3.40:

Protected E-C(2-3)-C(45-46)-Alkynyl-Phorboxazole (+)-3.39:

In a flame dried round bottom flask (5 mL), E-C(2-3)-vinyl iodide macrocycle (+)-2.5E (9.1 mg, 0.012 mmol) was combined with C(45-46)-TMS-alkynyl sidechain (−)-2.90 (13.7 mg, 0.017 mmol), azeotroped from benzene (2 mL, 3×) and dried under vacuum. After one hour, under an inert argon atmosphere, tris(dibenzylideneacetone)dipalladium-chloroform adduct [Pd$_2$(dba)$_3$.CHCl$_3$] (2.4 mg, 0.0023 mmol), triphenylarsine (AsPh$_3$) (4.2 mg, 0.014 mmol) and Ph$_2$PO$_2$NBu$_4$ (8 mg, 0.017 mmol) were added followed by anhydrous DMF (0.12 mL, sparged with argon, one hour), and diisopropylethylamine (0.002 ml, 0.011 mmol). After one minute, the black solution turned light brown and the reaction was stirred at room temperature. After twenty hours, the reaction mixture was purified directly via silica gel chromatography, (20% EtOAc/hexanes→30% EtOAc/hexanes)

To a flame dried round bottom flask (5 mL), C(22-26)-central tetrahydropyran (+)-2.44 (12.1 mg, 0.016 mmol) was combined with C(45-46)-alkenyl sidechain (−)-3.19 (18.0 mg, 0.025 mmol), azeotroped from benzene (2 mL, 3×) and dried under vacuum. After one hour, under an argon atmosphere, tris(dibenzylideneacetone)dipalladium-chloroform adduct [Pd$_2$(dba)$_3$.CHCl$_3$] (3.4 mg, 0.0033 mmol), triphenylarsine (AsPh$_3$) (6.1 mg, 0.020 mmol) and Ph$_2$PO$_2$NBu$_4$ (11.4 mg, 0.025 mmol) were added followed by anhydrous DMF (0.17 mL, sparged with argon, one hour), and diisopropylethylamine (0.003 mL, 0.016 mmol). After one minute, the black solution turned light brown and was allowed to stir at room temperature. After twenty hours, the reaction mixture was purified directly via silica gel chromatography (10% EtOAc/hexanes→30% EtOAc/hexanes) to afford protected C(45-46)-alkenyl-C(22-26)-central tetrahydropyran phorboxazole (+)-3.40 (12.9 mg, 69%) as a white foam. $[\alpha]_D^{20}$− 2.3 (c 0.064, CHCl$_3$); IR (neat) 2940 (b), 2863 (s), 1585 (b), 1513 (s), 1460 (s), 1383 (b), 1263 (b), 1100 (b), 801 (b), 701 (s) cm$^{-1}$; $^1$HNMR (500 MHz, C$_6$D$_6$) δ 7.81 (m, 3H), 7.28 (m, 2H), 7.25 (m, 2H), 7.14 (s, 1H), 6.97 (d, J=1.8 Hz, 1H), 6.92 (dd, J=8.1, 1.8 Hz, 1H), 6.7 (d, J=8.1 Hz, 1H), 6.38 (s, 1H), 6.22 (d, J=15.7 Hz, 1H), 5.90 (m, 1H), 5.56 (dd, J=15.7, 7.7 Hz, 1H), 5.53 (d, J=8.7 Hz, 1H), 5.07 (d, J=13.5 Hz, 1H), 5.04 (d, J=13.9 Hz, 1H), 4.73 (dd, J=8.8, 6.2 Hz, 1H), 4.53 (d, J=11.4 Hz, 1H), 4.21 (d, J=11.4 Hz, 1H), 3.97 (m, 1H), 3.84 (m, 1H), 3.75 (m, 2H), 3.69 (m, 1H), 3.56 (app q, J=6.5 Hz, 1H), 3.51 (s, 3H), 3.47 (d, J=10.2 Hz, 1H), 3.45 (s, 3H), 3.40 (s, 3H), 3.34 (d, J=14.8 Hz, 1H), 3.16 (dd, J=10.3, 4.6 Hz, 1H), 3.13 (s, 3H), 3.06 (s, 3H), 2.93 (d, J=14.8 Hz, 1H), 2.57 (dd, J=12.7, 3.2 Hz, 1H), 2.44 (m, 1H), 2.49 (m, 1H), 2.15 (ddd, J=10.2, 4.4, 2.0 Hz, 1H), 2.07 (s, 3H), 1.99 (m, 3H), 1.74 (m, 1H), 1.73 (s, 3H), 1.65 (dd, J=12.6, 11.0Hz, 1H), 1.33 (m, 2H), 1.21 (s, 9H), 1.15 (m, 23H), 1.10 (d, J=6.4 Hz, 3H), 0.96 (d, J=6.4 Hz, 3H); $^{13}$CNMR (125 MHz, C$_6$D$_6$) δ 160.1, 150.9, 150.4, 139.6, 139.2, 137.1, 136.8, 136.6, 136.5, 135.6, 135.2, 134.9, 134.9, 133.4, 132.7, 130.6, 130.3, 120.8, 119.3, 117.3, 113.0, 112.9, 101.1, 90.1, 84.4, 82.8, 75.5, 74.9, 74.3, 72.9, 70.4, 61.8, 56.6, 56.3, 56.2, 55.8, 48.5, 51.3, 40.7, 37.1, 36.5, 35.6, 34.4, 33.3, 27.7, 20.1, 18.9, 18.8, 14.8, 14.5, 14.3, 13.3, 3.6; high resolution mass spectrum (ES$^+$) m/z 1186.6799 [(M+Na)$^+$; calcd for C$_{68}$H$_{101}$NO$_{11}$Si$_2$Na: 1186.6809].

solid. [α]$_D^{20}$+64.1 (c 0.64, CH$_2$Cl$_2$); IR (neat) 3431 (b), 2920 (s), 1643 (b), 1189 (s), 1091 (s); $^1$HNMR (500 MHz, C$_6$D$_6$) δ 7.03 (s, 1H), 6.90 (s, 1H), 6.86 (m, 1H), 6.23 (d, J=15.7 Hz, 1H), 6.21 (d, J=15.8 Hz, 1H), 6.20 (s, 1H), 5.79 (dd, J=11.2, 2.3 Hz, 1H), 5.59 (dd, J=15.7, 7.5 Hz, 1H), 5.56 (d, J=9.9 Hz, 1H), 5.46 (ddd, J=13.1, 13.1, 2.7 Hz, 1H), 5.38 (s, 1H), 5.22 (s, 1H), 4.78 (d, J=9.4 Hz, 1H), 4.77 (s, 1H), 4.61 (dd, J=11.2, 4.4 Hz, 1H), 4.35 (app t, J=6.8 Hz, 1H), 4.02 (m, 2H), 3.92 (m, 2H), 3.77 (m, 2H), 3.64 (app q, J=6.3 Hz, 1H), 3.42 (m, 1H), 3.40 (d, J=10.1 Hz, 1H), 3.11 (d, J=13.8 Hz, 1H), 3.09 (s, 3H), 3.07 (s, 3H), 2.97 (d, J=11.0 Hz, 1H), 2.84 (d, J=15.4 Hz, 1H), 2.69 (d, J=15.4 Hz, 1H), 2.63 (m, 1H), 2.41 (m, 5H), 2.29 (m, 2H), 2.03 (m, 4H), 1.94 (s, 3H), 1.66 (d, J=0.9 Hz, 3H), 1.51 (m, 4H), 1.29 (m, 7H), 1.04 (d, J=6.9 Hz, 3H), 0.74 (d, J=6.5 Hz, 3H); $^{13}$CNMR (125 MHz, C$_6$D$_6$) δ 165.8, 161.7, 145.7, 143.8, 143.1, 139.1, 137.8, 137.2, 136.3, 134.4, 133.8, 131.9, 127.9, 121.4, 120.2, 118.7, 110.4, 97.2, 89.7, 81.3, 81.0, 80.1, 78.8, 73.8, 73.3, 71.4, 70.7, 69.9, 69.1, 67.5, 64.7, 56.6, 55.7, 42.3, 41.5, 40.2, 40.1, 39.6, 37.9, 35.5, 34.9, 33.9, 33.1, 32.4, 32.0, 31.2, 30.5, 30.1, 26.6, 23.4, 14.7, 13.7, 6.6; high resolution mass spectrum (ES$^+$) m/z 965.4766 [(M+Na)$^+$; calcd for C$_{53}$H$_{70}$N$_2$O$_{13}$: 965.4776].

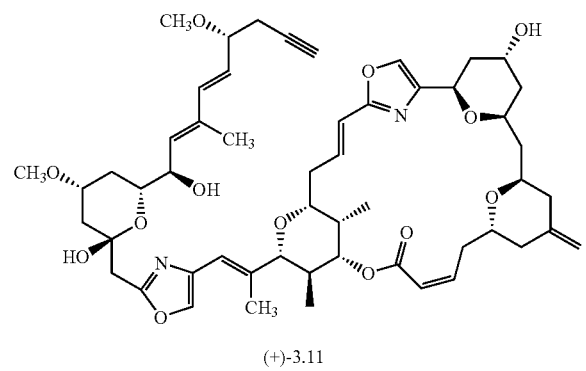

(+)-3.11

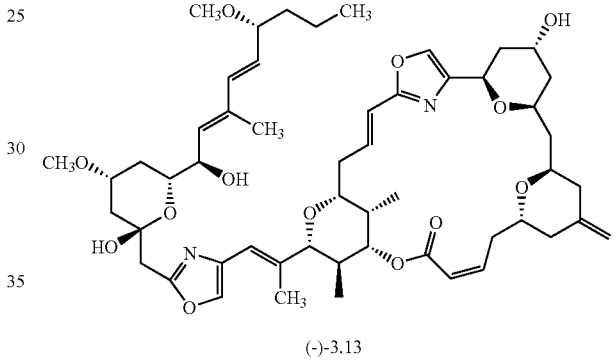

(−)-3.13

C(45-46)-Alkynyl-Phorboxazole (+)-3.11:

Fully protected C(45-46)-alkynyl-phorboxazole (+)-3.35 (3.8 mg, 0.003 mmol) was introduced into a flame dried round bottom flask, azeotroped from benzene (2 mL, 3×) and dried under vacuum. After one hour, (+)-3.35, under an argon atmosphere was dissolved in freshly distilled THF (0.7 mL) and cooled to 0° C. After five minutes, tetrabutylammonium fluoride (1.0 M/THF) (0.009 mL, 0.009 mmol) was added dropwise. After one hour, the reaction was quenched via dropwise addition of saturated aqueous sodium chloride (1 mL) and allowed to stir for thirty seconds. The layers of the biphasic mixture were separated and the aqueous layer extracted with ethyl acetate (4 mL, 4×). The combined organic extracts were dried over MgSO$_4$, filtered and concentrated under reduced pressure. The resultant crude amorphous solid, under an inert argon atmosphere was then dissolved in freshly distilled THF (2.1 mL) followed by dropwise addition of 6% hydrogen chloride solution (0.82 mL). After thirty six hours at room temperature, the reaction was cooled to 0° C., poured into saturated aqueous sodium bicarbonate (3 mL), extracted with dichloromethane (3 mL, 3×) followed by extraction with ethyl acetate (3 mL, 2×). The combined organic extracts were dried over MgSO$_4$, filtered and concentrated under reduced pressure. Purification via silica gel chromatography, (100% EtOAc→10% CH$_3$OH/EtOAc) afforded C(45-46)-alkynyl-phorboxazole (+)-3.11 (1.7 mg, 64%) as a white amorphous C(45-46)-Alkyl-Phorboxazole (−)-3.13:

Fully protected C(45-46)-alkyl-phorboxazole (+)-3.37 (13.1 mg, 0.010 mmol) was introduced into a flame dried round bottom flask, azeotroped from benzene (3 mL, 3×) and dried under vacuum. After one hour, under an argon atmosphere, (+)-3.37 was dissolved in freshly distilled THF (2.7 mL) and cooled to 0° C. Tetrabutylammonium fluoride (1.0 M/THF) (0.030 mL, 0.030 mmol) was then added dropwise and after one hour, the reaction was quenched via dropwise addition of saturated aqueous sodium chloride (2 mL) and the layers of the biphasic mixture were separated. The aqueous layer was extracted with ethyl acetate (3 mL, 4×) and the combined organic extracts were dried over MgSO$_4$, filtered and concentrated under reduced pressure. At room temperature under an argon atmosphere, the resultant amorphous solid was dissolved in freshly distilled THF (7.4 mL) followed by dropwise addition of 6% hydrogen chloride solution (2.9 mL). After thirty seven hours, the reaction mixture was cooled to 0° C., stirred for five minutes and poured into saturated aqueous sodium bicarbonate (5 mL). The layers were separated and the aqueous layer was extracted with dichloromethane (5 mL, 4×) followed by extraction with ethyl acetate (5 mL, 2×). The combined organic extracts were dried over MgSO$_4$, filtered and concentrated under reduced pressure. Purification via silica gel chromatography (100% EtOAc→10% CH$_3$OH/EtOAc) afforded C(45-46)-alkyl-phorboxazole (+)-3.13 (8.1 mg, 86%) as an off white amorphous solid. [α]$_D^{20}$−51.0 (c 0.19, CH$_2$Cl$_2$); IR (neat) 3401

(b), 2921 (b), 1715 (s), 1451 (b), 1374 (b), 1186 (s), 1157 (s), 1090 (s); $^1$HNMR (500 MHz, $C_6D_6$) δ 7.02 (s, 1H), 6.91 (s, 1H), 6.87 (m, 1H), 6.23 (d, J=15.8 Hz, 1H), 6.22 (s, 1H), 6.21 (d, J=15.6 Hz, 1H), 5.79 (dd, J=11.4, 2.7 Hz, 1H), 5.58 (d, J=10.1 Hz, 1H), 5.53 (dd, J=7.8, 4.1 Hz, 1H), 5.44 (ddd, J=10.8, 10.7, 2.6 Hz, 1H), 5.25 (s, 1H), 4.81 (dd, J=11.2, 2.1 Hz, 1H), 4.78 (s, 1H), 4.61 (dd, J=11.2, 4.4 Hz, 1H), 4.38 (dd, J=15.7, 7.2 Hz, 1H), 4.35 (br s, 1H), 4.08 (m, 2H), 3.97 (m, 2H), 3.79 (m, 2H), 3.52 (dd, J=12.5,6.1 Hz, 1H), 3.41 (m, 2H), 3.18 (s, 3H), 3.14 (m, 1H), 3.10 (dd, J=5.9, 2.2 Hz, 1H), 3.07 (s, 3H), 3.01 (d, J=10.6 Hz, 1H), 2.86 (d, J=15.3 Hz, 1H), 2.74 (d, J=15.3 Hz, 1H), 2.65 (br s, 1H), 2.42 (m, 4H), 2.30 (dd, J=13.0, 5.4 Hz, 1H), 2.02 (m, 5H), 1.93 (s, 3H), 1.80 (m, 1H), 1.68 (d, J=0.8 Hz, 3H), 1.56 (m, 5H), 1.42 (m, 2H), 1.29 (m, 4H), 1.04 (d, J=6.8 Hz, 3H), 0.90 (app t, J=5.8 Hz, 3H), 0.74 (d, J=6.4 Hz, 3H); $^{13}$CNMR (125 MHz, $C_6D_6$) δ 165.9, 161.8, 161.3, 145.9, 143.9, 143.3, 139.2, 138.6, 137.7, 137.1, 136.5, 134.5, 134.0, 131.4, 131.3, 128.0, 127.9, 121.5, 120.4, 118.9, 110.7, 97.4, 89.9, 83.0, 80.3, 79.0, 73.9, 73.5, 71.6, 70.1, 69.3, 67.7, 64.8, 56.6, 55.8, 42.5, 41.6, 40.4, 40.2, 39.8, 39.1, 38.1, 35.6, 35.1, 34.1, 33.3, 32.6, 31.3, 19.6, 14.9, 14.0, 13.9, 6.8; high resolution mass spectrum (ES$^+$) m/z 969.5174 [(M+Na)$^+$; calcd for $C_{53}H_{74}N_2O_{13}Na$: 969.5189].

(c 0.51, $CH_2Cl_2$); IR (neat) 3404 (b), 2927 (b), 1716 (s), 1661 (b), 1441 (b), 1372 (b), 1188 (s), 1161 (s), 1092 (s); $^1$HNMR (500 MHz, $C_6D_6$) δ 7.02 (s, 1H), 6.89 (s, 1H), 6.85 (m, 1H), 6.21 (d, J=12.7 Hz, 1H), 6.20 (s, 1H), 6.18 (d, J=15.8 Hz, 1H), 5.93 (m, 1H), 5.79 (dd, J=11.2, 2.4 Hz, 1H), 5.55 (d, J=8.6 Hz, 1H), 5.53 (dd, J=15.7, 7.6 Hz, 1H), 5.45 (app t, J=10.4 Hz, 1H), 5.23 (s, 1H), 5.07 (s, 1H), 5.06 (d, J=10.1 Hz, 1H), 4.79 (d, J=8.8 Hz, 1H), 4.78 (s, 1H), 4.61 (dd, J=11.1, 4.4 Hz, 1H), 4.37 (m, 2H), 4.06 (m, 2H), 3.93 (m, 2H), 3.78 (m, 2H), 3.56 (app q, J=6.4 Hz, 1H), 3.41 (m, 1H), 3.39 (d, J=9.9 Hz, 1H), 3.14 (s, 3H), 3.13 (m, 1H), 3.07 (s, 3H), 2.99 (d, J=11.5 Hz, 1H), 2.83 (d, J=15.3 Hz, 1H), 2.69 (d, J=15.4 Hz, 1H), 2.65 (app t, J=6.5 Hz, 1H), 2.40 (m, 4H), 2.27 (m, 2H), 2.04 (m, 2H), 1.98 (d, J=12.3 Hz, 2H), 1.93 (s, 3H), 1.67 (d, J=0.8 Hz, 3H), 1.49 (m, 5H), 1.28 (m, 6H), 1.04 (d, J=6.9 Hz, 3H), 0.73 (d, J=6.4 Hz, 3H); $^{13}$CNMR (125 MHz, $C_6D_6$) δ 165.8, 161.7, 161.2, 145.7, 143.7, 143.1, 139.0, 138.4, 137.4, 137.2, 136.3, 135.5, 134.3, 133.8, 131.4, 130.4, 130.3, 121.3, 120.2, 118.7, 117.2, 110.5, 97.3, 89.7, 82.6, 80.1, 78.8, 73.7, 73.3, 71.4, 69.9, 69.1, 67.5, 64.7, 56.4, 55.7, 42.3, 41.4, 41.3, 40.2, 40.0, 39.6, 37.9, 35.5, 34.9, 33.9, 33.1, 32.4, 31.2, 14.7, 13.8, 13.7, 6.6; high resolution mass spectrum (ES$^+$) m/z 967.4971 [(M+Na)$^+$; calcd for $C_{53}H_{72}N_2O_{13}Na$: 967.4931].

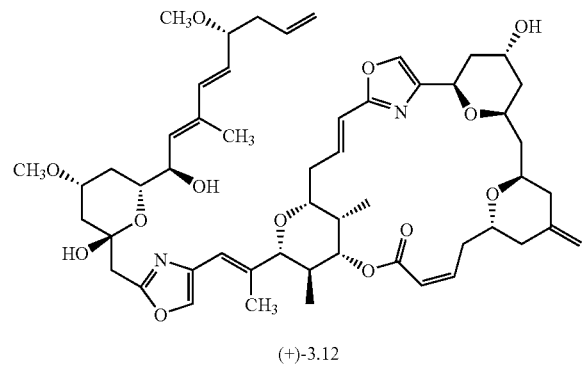

(+)-3.12

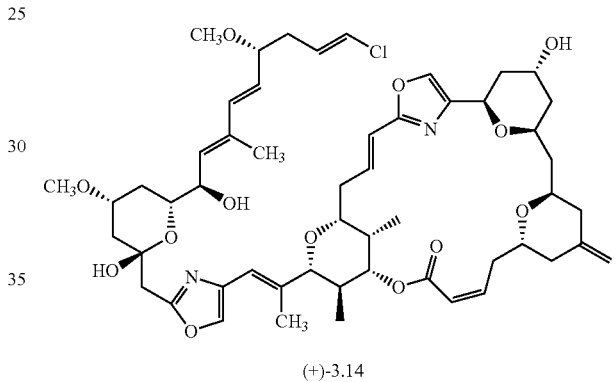

(+)-3.14

C(45-46)-Alkenyl-Phorboxazole (+)-3.12:

Fully protected C(45-46)-alkenyl-phorboxazole (+)-3.36 (3.8 mg, 0.003 mmol) was introduced into a flame dried round bottom flask, azeotroped from benzene (3 mL, 3×) and dried under vacuum. After one hour, under an argon atmosphere, (+)-3.36 was dissolved in freshly distilled THF (1 mL), cooled to 0° C. and tetrabutylammonium fluoride (1.0 M/THF) (0.009 mL, 0.009 mmol) was added dropwise. After one hour, the reaction was quenched via dropwise addition of saturated aqueous sodium chloride (2 mL) and the layers of the biphasic mixture were separated. The aqueous layer was extracted with ethyl acetate (3 mL, 4×) and the combined organic extracts were dried over $MgSO_4$, filtered and concentrated under reduced, pressure. At room temperature under an argon atmosphere, the resultant amorphous solid was dissolved in freshly distilled THF (5 mL) followed by dropwise addition of 6% hydrogen chloride solution (2.0 mL). After thirty seven hours, the reaction mixture was cooled to 0° C., stirred for five minutes and poured into saturated aqueous sodium bicarbonate (5 mL). The layers were separated and the aqueous layer was extracted with dichloromethane (5 mL, 4×) followed by extraction with ethyl acetate (5 mL, 2×). The combined organic extracts were dried over $MgSO_4$, filtered and concentrated under reduced pressure. Purification via silica gel chromatography, (100% EtOAc→10% $CH_3OH$/EtOAc) afforded C(45-46)-alkenyl-phorboxazole (+)-3.12 (1.9 mg, 67%) as an off white amorphous solid. $[\alpha]_D^{20}$+49.7

C(45-46)-E-Chloroalkenyl-Phorboxazole (+)-3.14:

Fully protected C(45-46)-E-chloroalkenyl-phorboxazole (+)-3.38 (8.2 mg, 0.006 mmol) was introduced into a flame dried round bottom flask, azeotroped from benzene (3 mL, 3×) and dried under vacuum. After one hour, under an inert argon atmosphere, (+)-3.38 was dissolved in freshly distilled THF (5.3 mL), cooled to 0° C. and tetrabutylammonium fluoride (1.0 M/THF) (0.018 mL, 0.018 mmol) was added dropwise. After one hour, the reaction was quenched via dropwise addition of saturated aqueous sodium chloride (5 mL) and allowed to stir for one minute. The layers of the biphasic mixture were separated and the aqueous layer extracted with ethyl acetate (5 mL, 4×). The combined organic extracts were dried over $MgSO_4$, filtered and concentrated under reduced pressure. The resultant off white amorphous solid, under an argon atmosphere was dissolved in freshly distilled THF (7.4 mL) followed by dropwise addition of 6% hydrogen chloride solution (2.9 mL). After stirring for thirty-six hours at room temperature, the reaction was cooled to 0° C. and poured into saturated aqueous sodium bicarbonate (5 mL). The resultant layers were separated and the aqueous layer extracted with dichloromethane (5 mL, 4×) followed by ethyl acetate (5 mL, 2×). The combined organic extracts were dried over $MgSO_4$, filtered and concentrated under reduced pressure. Purification via silica gel chromatography, (100% EtOAc→10% $CH_3OH$/EtOAc) afforded C(45-46)-E-chloroalkenyl-phorboxazole (+)-3.14 (3.8 mg, 61%)

as a white amorphous solid. $[\alpha]_D^{20}$+47.8 (c 0.39, $CH_2Cl_2$); IR (neat) 3411 (b), 2926 (s), 1720 (s), 1647 (b), 1443 (b), 1375 (b), 1186 (s), 1156 (s), 1088 (s), 991 (b); $^1$HNMR (500 MHz, $C_6D_6$) δ 7.04 (s, 1H), 6.91 (s, 1H), 6.87 (m, 1H), 6.22 (d, J=15.7 Hz, 1H), 6.21 (s, 1H), 6.10 (d, J=15.7 Hz, 1H), 5.98 (m, 1H), 5.80 (dd, J=11.0, 2.9 Hz, 1H), 5.74 (d, J=13.3 Hz, 1H), 5.55 (d, J=8.8 Hz, 1H), 5.45 (ddd, J=12.7, 12.6, 1.2 Hz, 1H), 5.37 (dd, J=15.7, 7.8 Hz, 1H), 5.24 (s, 1H), 4.81 (d, J=11.1 Hz, 1H), 4.78 (s, 1H), 4.61 (dd, J=11.1, 4.3 Hz, 1H), 4.37 (m, 2H), 4.08 (m, 2H), 3.96 (m, 2H), 3.80 (m, 2H), 3.41 (m, 1H), 3.39 (d, J=9.9 Hz, 1H), 3.36 (app q, J=7.3 Hz, 1H), 3.08 (s, 3H), 3.04 (s, 3H), 3.00 (dd, J=11.1, 0.9 Hz, 1H), 2.86 (d, J=15.3 Hz, 1H), 2.74 (d, J=15.3 Hz, 1H), 2.65 (app t, J=5.2 Hz, 1H), 2.42 (m, 4H), 2.30 (dd, J=12.1, 4.3 Hz, 1H), 2.11 (m, 1H), 2.01 (m, 6H), 1.92 (d, J=0.5 Hz, 3H), 1.63 (d, J=0.9 Hz, 3H), 1.54 (m, 4H), 1.29 (m, 6H), 1.05 (d, J=6.8 Hz, 3H), 0.73 (d, J=6.4 Hz, 3H); $^{13}$CNMR (125 MHz, $C_6D_6$) δ 165.1, 161.0, 160.5, 145.1, 143.1, 142.4, 138.4, 137.7, 136.9, 136.6, 135.6, 133.6, 133.2, 131.2, 129.9, 127.2, 120.7, 119.6, 119.2, 118.1, 109.8, 96.6, 89.1, 81.1, 79.4, 78.1, 73.1, 72.6, 70.7, 69.3, 68.5, 66.9, 64.0, 55.7, 55.0, 41.6, 40.7, 39.5, 39.4, 39.0, 37.4, 37.3, 34.8, 34.3, 33.6, 33.2, 32.4, 31.7, 30.5, 14.1, 14.0, 13.1, 6.0; high resolution mass spectrum (ES$^+$) m/z 1002.5813 [(M+Na)$^+$ calcd for $C_{53}H_{71}ClN_2O_{13}Na$: 1002.5801].

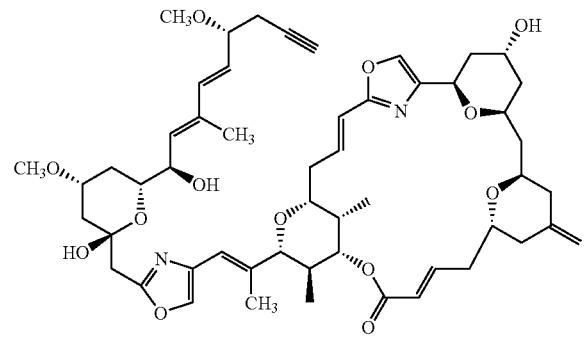

(+)-3.15

E-C(2-3)-C(45-46)-Alkynyl-Phorboxazole (+)-3.15:

Fully protected E-C(2-3)-C(45-46)-alkynyl-phorboxazole (+)-3.39 (6.8 mg, 0.005 mmol) was introduced into a flame dried round bottom flask, azeotroped from benzene (3 mL, 3×) and dried under vacuum. After one hour, under an inert argon atmosphere, (+)-3.39 was dissolved in freshly distilled THF (1.3 mL) followed by dropwise introduction of tetrabutylammonium fluoride (1.0 M/THF) (0.015 mL, 0.015 mmol). After one hour, the reaction was quenched via dropwise addition of saturated aqueous sodium chloride (2 mL). After stirring for one minute at 0° C., the layers of the biphasic mixture were separated and the aqueous phase was extracted with ethyl acetate (5 mL, 4×). The combined organic extracts were dried over MgSO$_4$, filtered and concentrated under reduced pressure. The resultant amorphous solid, under an inert argon atmosphere was dissolved in freshly distilled THF (4.7 mL) followed by dropwise introduction of 6% hydrogen chloride solution (1.9 mL) and allowed to stir at room temperature. After thirty six hours, the reaction was cooled to 0° C. and poured into saturated aqueous sodium bicarbonate (5 mL). The biphasic mixture was separated and the aqueous layer was extracted with dichloromethane (5 mL, 4×) followed by extraction with ethyl acetate (5 mL, 2×). The combined organic extracts were dried over MgSO$_4$, filtered and concentrated under reduced pressure. Purification via silica gel chromatography, 100% EtOAc→10% $CH_3OH$/EtOAc) afforded E-C(2-3)-C(45-46)-alkynyl-phorboxazole (+)-3.15 (3.3 mg, 69%) as an off white amorphous solid. $[\alpha]_D^{20}$+51.6 (c 0.31, $CH_2Cl_2$); IR (neat) 3431 (b), 2924 (s), 1695 (s), 1195 (b), 993 (s); $^1$HNMR (500 MHz, $C_6D_6$) δ 7.00 (s, 1H), 6.93 (s, 1H), 6.86 (m, 1H), 6.23 (d, J=15.7 Hz, 1H), 6.15 (d, J=14.5 Hz, 1H), 6.13 (s, 1H), 6.05 (d, J=15.1 Hz, 1H), 5.59 (dd, J=15.6, 7.5 Hz, 1H), 5.56 (d, J=8.9 Hz, 1H), 5.47 (s, 1H), 5.07 (dd, J=10.8, 3.8 Hz, 1H), 4.82 (dd, J=11.7, 2.1 Hz, 1H), 4.7 (s, 1H), 4.62 (s, 1H), 4.35 (app t, J=7.3 Hz, 1H), 4.31 (br s, 1H), 3.97 (dd, J=10.4, 7.6 Hz, 1H), 3.83 (m, 3H), 3.63 (app q, J=6.7 Hz, 1H), 3.45 (br s, 1H), 3.37 (m, 1H), 3.34 (d, J=10.0 Hz, 1H), 3.09 (s, 3H), 3.08 (s, 3H), 2.84 (d, J=15.3 Hz, 1H), 2.70 (d, J=16.0 Hz, 1H), 2.51 (br s, 1H), 2.45 (dd, J=5.7, 2.6 Hz, 1H), 2.35 (dd, J=6.6, 2.6 Hz, 1H), 2.27 (m, 4H), 2.11 (m, 3H), 1.96 (m, 4H), 1.89 (s, 3H), 1.79 (m, 2H), 1.70 (m, 2H), 1.66 (d, J=3.4 Hz, 3H), 1.48 (d, J=12.6 Hz, 1H), 1.32 (m, 4H), 1.22 (m, 3H), 0.85 (d, J=6.6 Hz, 3H), 0.82 (d, J=6.5 Hz, 3H); $^{13}$CNMR (125 MHz, $C_6D_6$) δ 167.5, 162.5, 161.2, 147.6, 143.8, 142.8, 139.3, 138.6, 138.0, 137.4, 136.4, 134.5, 132.2, 128.0, 127.9, 124.2, 119.1, 118.8, 111.4, 100.9, 99.2, 97.4, 89.7, 81.5, 81.2, 79.2, 77.3, 74.0, 73.9, 73.4, 71.6, 71.0, 70.9, 66.1, 64.9, 56.8, 55.9, 41.6, 41.3, 40.3, 39.5, 38.6, 38.5, 38.3, 38.0, 35.5, 34.0, 30.7, 26.7, 26.7, 14.8, 13.9, 6.1; high resolution mass spectrum (ES$^+$) m/z 965.4831 [(M+Na)$^+$; calcd for $C_{53}H_{70}N_2O_{13}Na$: 965.4843].

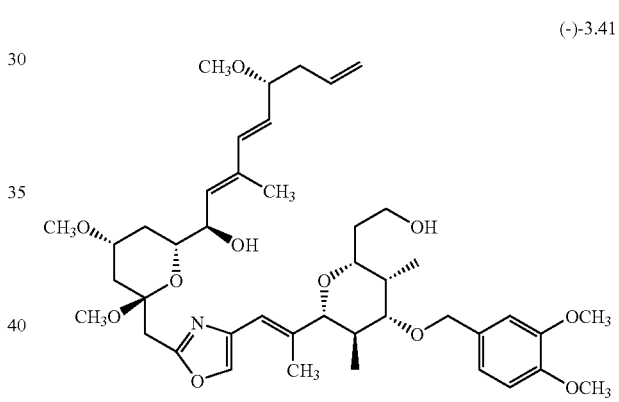

(-)-3.41

C(45-46)-Alkenyl-C(22-26)-Central Tetrahydropyran Phorboxazole (-)-3.41:

Fully protected C(45-46)-alkenyl-C(22-26)-central tetrahydropyran phorboxazole (-)-3.40 (12.9 mg, 0.011 mmol) was introduced into a flame dried round bottom flask, azeotroped from benzene (5 mL, 3×) and dried under vacuum. After one hour, under an argon atmosphere, (-)-3.40 was dissolved in freshly distilled THF (2.7 mL), followed by cooling to 0° C. and dropwise addition of tetrabutylammonium fluoride (1.0 M/THF) (0.022 mL, 0.022 mmol). After one hour, the reaction was warmed to room temperature and after 2.5 total hours of reacting, the reaction was quenched via dropwise addition of saturated aqueous sodium chloride (3 mL). The layers of the biphasic mixture were separated and the aqueous layer was extracted with ethyl acetate (5 mL, 4×). The combined organic extracts were dried over MgSO$_4$, filtered and concentrated under reduced pressure. The resultant off white amorphous solid, under an argon atmosphere was dissolved in freshly distilled THF (7.1 mL) followed by dropwise introduction of 6% hydrogen chloride solution (2.8 mL). After stirring at room temperature for thirty six hours, the reaction was cooled to 0° C. and poured into saturated aqueous sodium bicarbonate (5 mL). The layers of the resultant biphasic mixture were separated and the aqueous layer was extracted with dichloromethane (5 mL, 4×) followed by extraction with ethyl acetate (5 mL, 2×). The combined organic extracts were dried over MgSO$_4$, filtered and concentrated under reduced pressure. Purification via silica gel chromatography, (100% EtOAc→10% CH$_3$OH/EtOAc) afforded C(45-46)-alkenyl-C(22-26)-central tetrahydropyran phorboxazole (−)-3.41 (7.1 mg, 66%) as an off white amorphous solid. [α]$_D^{20}$ −69.0 (c 0.16, CH$_2$Cl$_2$); IR (neat) 2921 (b), 1515 (s), 1454 (b), 1420 (s), 1376 (b), 1260 (s), 1238 (s), 1152 (s), 1087 (b), 1027 (s), 966 (s); $^1$HNMR (500 MHz, C$_6$D$_6$) 66.99 (s, 1H), 6.97 (d, J=1.8 Hz, 1H), 6.92 (dd, J=8.0, 1.7 Hz, 1H), 6.67 (d, J=8.1 Hz, 1H), 6.19 (s, 1H), 6.18 (d, J=15.7 Hz, 1H), 5.92 (m, 1H), 5.54 (d, J=8.6 Hz, 1H), 5.52 (dd, J=15.6, 7.6 Hz, 1H), 5.40 (s, 1H), 5.08 (d, J=15.9 Hz, 2H), 5.05 (d, J=10.1 Hz, 1H), 4.52 (d, J=11.4 Hz, 1H), 4.36 (app t, J=7.3 Hz, 1H), 4.21 (d, J=11.4 Hz, 1H), 3.96 (dddd, J=11.8, 6.9, 5.0, 4.8 Hz, 1H), 3.77 (m, 1H), 3.64 (m, 2H), 3.56 (app q, J=6.5 Hz, 1H), 3.52 (s, 3H), 3.44 (s, 3H), 3.35 (d, J=10.3 Hz, 1H), 3.14 (s, 3H), 3.07 (s, 3H), 3.06 (m, 2H), 2.84 (d, J=15.4 Hz, 1H), 2.70 (d, J=15.5 Hz, 1H), 2.44 (m, 2H), 2.29 (m, 2H), 1.97 (d, J=14.5 Hz, 1H), 1.91 (m, 3H), 1.88 (d, J=0.9 Hz, 3H), 1.66 (d, J=1.1 Hz, 3H), 1.31 (m, 4H), 1.07 (d, J=6.9 Hz, 3H), 0.90 (d, J=6.4 Hz, 3H); $^{13}$CNMR (125 MHz, C$_6$D$_6$) δ 161.0, 150.7, 150.2, 139.4, 138.3, 137.3, 137.3, 136.2, 135.5, 132.2, 131.5, 130.1, 120.5, 118.7, 117.2, 112.6, 112.5, 97.2, 89.5, 83.4, 82.6, 77.7, 73.7, 73.3, 71.4, 70.2, 61.2, 56.4, 56.1, 56.0, 55.7, 41.5, 41.2, 40.1, 36.3, 35.4, 33.9, 33.9, 14.6, 14.3, 13.7, 6.8; high resolution mass spectrum (ES$^+$) m/z 778.4134 [(M+Na)$^+$; calcd for C$_{42}$H$_{61}$NO$_{11}$Na: 778.4141].

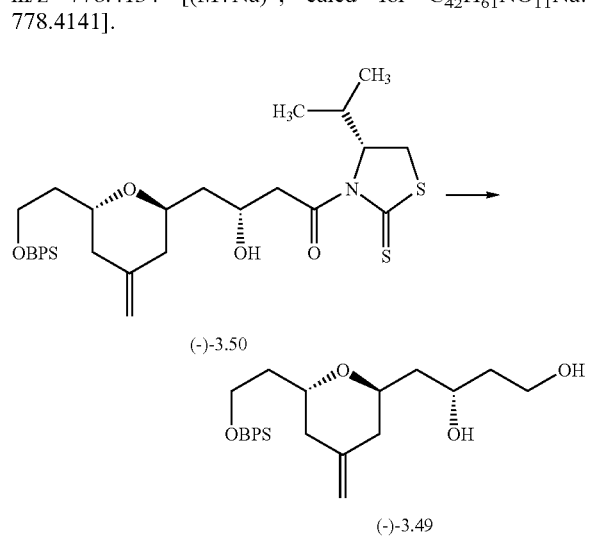

(−)-3.50

(−)-3.49

Diol (−)-3.49:

To a solution of β-Hydroxyimide (−)-3.50 (Smith, et al. *J. Am. Chem. Soc.* 2001, 123, 10942) (1.0 g, 1.56 mmol) in diethyl ether (6.25 mL) at 0° C. under argon was added H$_2$O (0.031 mL, 1.72 mmol) and LiBH$_4$ (0.037 g, 1.72 mmol) in one portion. After stirring at 0° C. for 10 minutes, the reaction was warmed to room temperature, stirred for 10 minutes, cooled back to 0° C. and quenched with pH 7 phosphate buffer (7 mL). The layers of the biphasic mixture were separated and the aqueous layer was extracted with diethyl ether (20 mL, 3×). The combined organic extracts were washed with saturated aqueous sodium chloride (20 mL, 1×), dried over MgSO$_4$, filtered and concentrated under reduced pressure. Purification via silica gel chromatography (50% EtOAc/hexanes) afforded (−)-3.49 (0.604 g, 83% yield) as a colorless oil: [α]$_D^{20}$ −18.3 (c 1.0, CHCl$_3$); IR (neat) 3397 (b), 3070 (w), 2939 (s), 2857 (s), 1654 (w), 1472 (w), 1428 (s), 1389 (w), 1110 (s), 890 (m), 823 (m), 740 (m), 701 (s) cm$^{-1}$; $^1$HNMR (500 MHz, CDCl$_3$) δ 7.67 (m, 4H), 7.40 (m, 6H), 4.78 (s, 1H), 4.72 (s, 1H), 4.25 (m, 1H), 3.92 (m, 1H), 3.89 (s, 1H), 3.76 (m, 4H), 3.67 (ddd, J=10.8, 6.7, 5.6 Hz, 1H), 2.87 (dd, J=6.7, 4.5 Hz, 1H), 2.45 (dd, J=13.4, 5.6 Hz, 1H), 2.21 (dd, J=13.1, 3.0 Hz, 1H), 2.01 (m, 2H), 1.94 (dddd, J=14.1, 8.6, 5.6, 5.6 Hz, 1H), 1.75 (ddd, J=14.5, 10.1, 10.1 Hz, 1H), 1.65 (m, 3H), 1.43 (ddd, J=14.5, 2.2, 2.2 Hz, 1H), 1.05 (s, 9H); $^{13}$CNMR (125 MHz, CDCl$_3$) δ 141.0, 135.4, 135.3, 133.6, 133.4, 129.5, 129.4, 127.58, 127.52, 110.5, 71.7, 71.5, 70.1, 61.0, 60.3, 41.4, 40.5, 38.55, 38.53, 34.3, 26.7, 18.9; high resolution mass spectrum (ES$^+$) m/z 491.2686 [(M+Na)$^+$; calcd for C$_{28}$H$_{40}$O$_4$SiNa: 491.2593].

(−)-3.51

C(11-15) Acetal (−)-3.51:

Under an argon atmosphere at −78° C., 1,1,1,3,3,3-hexamethyldisilazane (HMDS) (0.93 mL, 4.41 mmol) was added dropwise via syringe to a stirred solution of diol (−)-3.49 (1.97 g, 4.21 mmol) in CH$_2$Cl$_2$ (10 mL). Following the addition, the reaction was warmed to room temperature. After twenty hours, the reaction was concentrated under reduced pressure followed by drying under vacuum (to remove excess 1,1,1,3,3,3-hexamethyldisilazane) to provide the corresponding bis-silylated diol, which was used without further purification. Under an argon atmosphere at 0° C., trimethylsilyl trifluoromethanesulfonate (TMSOTf) (0.148 mL, 0.82 mmol) was added dropwise to a solution of oxazole 3.48 (Smith, et al. *Org. Lett.* 1999, 1, 909) (2.00 g, 8.11 mmol) and the bis-silylated diol in CH$_2$Cl$_2$ (21 mL). After stirring for fifteen hours, the reaction was cooled to −78° C., quenched with triethylamine (2.35 mL, 16.8 mmol), and warmed to room temperature over one hour. The reaction was diluted with saturated aqueous sodium bicarbonate (20 mL) and extracted with CH$_2$Cl$_2$ (10 mL, 3×). The combined organic extracts were dried over MgSO$_4$, filtered and concentrated under reduced pressure. Purification via silica gel chromatography (10% EtOAc/hexanes→20% EtOAc/hexanes) afforded C(11-15) acetal (−)-3.51 (2.52 g, 86% yield) as a light yellow oil: [α]$_D^{20}$ −16.1 (c 0.5, CHCl$_3$); IR (neat) 3150 (w), 3070 (m), 2930 (s), 2856 (s), 1889 (w), 1821 (w), 1727 (w), 1653 (m), 1612 (s), 1586 (m), 1513 (s), 1464 (m), 1428 (s), 1375 (m), 1302 (m), 1249 (s), 1175 (m), 1111 (s), 1036 (s), 822 (s), 741 (m), 704 (s) 614 (m) cm$^{-1}$; $^1$HNMR (500 MHz, CDCl$_3$) δ 7.66 (m, 5H), 7.39 (m, 6H), 7.26 (m, 2H), 6.87 (m, 2H), 5.44 (s, 1H), 4.75 (s, 2H), 4.55 (s, 2H), 4.52 (s, 2H), 4.14 (dd, J=11.5, 4.8 Hz, 1H), 4.03 (m, 1H), 3.87 (m, 2H), 3.80 (s, 3H), 3.72 (m, 3H), 2.34 (ddd, J=13.0, 3.4, 3.4 Hz, 2H), 2.10 (ddd, J=14.1, 8.2, 5.6 Hz, 1H), 2.00 (m, 2H), 1.85 (m, 1H), 1.73 (m, 1H), 1.67 (m, 1H), 1.51 (m, 1H), 1.05 (s, 9H); $^{13}$CNMR (125 MHz, CDCl$_3$) δ 161.1, 159.4, 141.8, 139.1, 136.9, 135.5, 133.82, 133.79, 129.7, 129.6, 129.2, 127.63, 127.58, 113.84, 113.81, 110.4, 96.1, 74.0, 72.5, 68.9, 67.8, 66.8, 63.5, 60.6, 55.2, 39.7, 39.6, 39.0, 36.4, 30.7, 29.6, 26.8, 19.1; high resolution mass spectrum (ES+) m/z 698.3538 [(M+H)+; calcd for $C_{41}H_{51}NO_7SiH$: 698.3513].

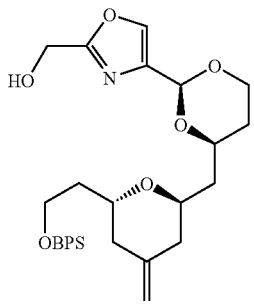

(-)-3.S₄

Alcohol Tricycle (-)-3.S₄:

2,3-Dichloro-5,6-dicyano-1,4-benzoquinone (DDQ) (1.24 g, 5.47 mmol) was added as one portion to a solution of C(11-15) acetal (-)-3.51 (1.80 g, 2.60 mmol) in $CH_2Cl_2$ (260 mL) and $H_2O$ (17.4 mL) at room temperature under an argon atmosphere. After stirring for twelve hours, the reaction was quenched via dropwise addition of saturated aqueous sodium bicarbonate (30 mL). The layers of the biphasic mixture were separated and the aqueous layer was extracted with $CH_2Cl_2$ (20 mL, 4×). The combined organic extracts were dried over $MgSO_4$, filtered and concentrated under reduced pressure. Purification via silica gel chromatography (50% EtOAc/hexanes) afforded alcohol tricycle (-)-3.S₄ (1.26 g, 84% yield) as a light yellow oil: $[\alpha]_D^{20}$ -18.9 (c 0.5, $CHCl_3$); IR (neat) 3376 (b), 3158 (w), 3071 (m), 2931 (s), 2857 (s), 1901 (w), 1828 (w), 1652 (m), 1578 (m), 1471 (m), 1428 (s), 1375 (m), 1237 (m), 1185 (m), 1112 (s), 1038 (s), 1010 (m), 937 (w), 893 (w), 823 (s), 757 (s), 704 (s), 614 (m) cm¹; ¹HNMR (500 MHz, $CDCl_3$) δ 7.66 (m, 4H), 7.61 (s, 1H), 7.40 (m, 6H), 5.43 (s, 1H), 4.75 (s, 2H), 4.71 (s, 1H), 4.69 (s, 1H), 4.14 (dd, J=12.3, 4.8 Hz, 1H), 4.01 (m, 1H), 3.87 (m, 2H), 3.75 (m, 2H), 3.68 (m, 1H), 2.44 (m, 1H), 2.34 (ddd, J=13.4, 3.7, 3.7 Hz, 2H), 2.11 (ddd, J=14.1, 8.9, 5.6 Hz, 1H), 1.99 (m, 2H), 1.86 (m, 1H), 1.76 (m, 1H), 1.67 (m, 1H), 1.51 (m, 2H), 1.05 (s, 9H); ¹³CNMR (125 MHz, $CDCl_3$) δ 163.1, 141.8, 139.0, 136.5, 135.5, 133.8, 129.7, 129.6, 127.63, 127.62, 127.60, 127.58, 110.4, 95.9, 74.0, 68.9, 67.8, 66.8, 60.6, 57.6, 39.7, 39.6, 39.0, 36.4, 30.7, 26.8, 19.1; high resolution mass spectrum (ES+) m/z 600.2766 [(M+Na)+; calcd for $C_{33}H_{43}NO_6SiNa$: 600.2757].

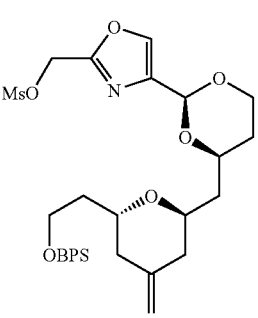

(-)-3.52

Mesylate Tricycle (-)-3.52:

N,N-Diisopropylethylamine (0.65 mL, 3.75 mmol) followed by dropwise addition of methanesulfonyl chloride (0.17 mL, 2.25 mmol) were added to a solution of alcohol tricycle (-)-3.S₄ (1.08 g, 1.87 mmol) in $CH_2Cl_2$ (117 mL) at 0° C. under an argon atmosphere. After one hour, the reaction mixture was filtered through a plug of silica gel (40% EtOAc/hexanes) to afford mesylate tricycle (-)-3.52 (1.20 g, 98% yield) as a colorless oil: $[\alpha]_D^{20}$ -15.2 (c 1.0, $CHCl_3$); IR (neat) 3071 (w), 2933 (s), 2857 (s), 1653 (w), 1587 (w), 1472 (w), 1428 (m), 1353 (s), 1238 (w), 1177 (s), 1112 (s), 1034 (m), 958 (m), 822 (w), 743 (w), 704 (s), 613 (m) cm⁻¹; ¹HNMR (500 MHz, $CDCl_3$) δ 7.70 (s, 1H), 7.66 (m, 4H), 7.39 (m, 6H), 5.43 (s, 1H), 5.25 (s, 2H), 4.75 (br s, 2H), 4.14 (dd, J=12.3, 4.8 Hz, 1H), 4.01 (m, 1H), 3.87 (m, 2H), 3.72 (m, 3H), 3.06 (s, 3H), 2.35 (dd, J=13.0, 3.7 Hz, 2H), 2.10 (ddd, J=14.1, 8.9, 5.6 Hz, 1H), 2.00 (m, 2H), 1.85 (dddd, J=14.1, 8.6, 5.6, 5.6 Hz, 1H), 1.71 (m, 1H), 1.67 (m, 1H), 1.52 (m, 2H), 1.05 (s, 9H); ¹³CNMR (125 MHz, $CDCl_3$) δ 156.7, 141.7, 140.0, 138.0, 135.5, 133.8, 129.7, 129.6, 127.65, 127.64, 127.61, 127.60, 110.5, 95.7, 74.1, 68.9, 67.8, 66.8, 61.7, 60.6, 39.7, 39.6, 39.0, 38.3, 36.4, 30.7, 26.8, 19.1; high resolution mass spectrum (ES+) m/z 678.2509 [(M+Na)+; calcd for $C_{34}H_{45}NO_8SSiNa$: 678.2533].

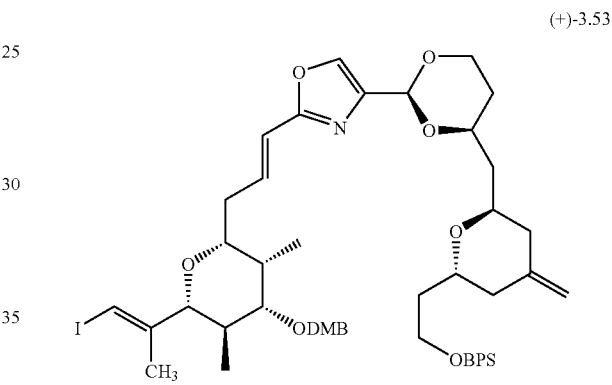

(+)-3.53

C(19-20) E-Olefin (+)-3.53:

Tri-n-butylphosphine (0.56 mL, 2.24 mmol) was added dropwise to a stirred solution of mesylate tricycle (-)-3.52 (0.37 g, 0.56 mmol) in anhydrous N,N-dimethylformamide (DMF) (119 mL) at room temperature under an argon atmosphere. After stirring for twenty-four hours, a solution of aldehyde (+)-2.12 (0.27 g, 0.56 mmol) in DMF (63 mL) was introduced dropwise via cannula. Following five minutes of stirring, 1,8-diazabicyclo[5.4.0]undec-7-ene (DBU) (0.17 mL, 1.12 mmol) was added dropwise via syringe. After one hour, the reaction was diluted with diethyl ether (50 mL), poured into $H_2O$ (50 mL), and the organic layer was washed with $H_2O$ (20 mL, 5×). The combined organic extracts were washed with saturated aqueous sodium chloride (20 mL, 1×), dried over $MgSO_4$, filtered, and concentrated under reduced pressure. Purification via silica gel chromatography (25% EtOAc/hexanes) afforded C(19-20) E-olefin (+)-3.53 (0.53 g, 91% yield, 19:1, E:Z) as a light yellow oil: $[\alpha]_D^{20}$ +22.2 (c 1.0, $CHCl_3$); IR (neat) 3070 (m), 2928 (s), 2855 (s), 1653 (m), 1592 (m), 1516 (s), 1463 (s), 1427 (s), 1388 (w), 1263 (m), 1238 (m), 1139 (m), 1110 (s), 1031 (s), 972 (m), 893 (w), 857 (w), 822 (w), 756 (s), 704 (s), 614 (m) cm⁻¹; ¹HNMR (500 MHz, $CDCl_3$) δ 7.66 (m, 4H), 7.54 (s, 1H), 7.39 (m, 6H), 6.89 (s, 1H), 6.87 (d, J=8.3Hz, 1H), 6.83 (d, J=8.1 Hz, 1H), 6.68 (m, 1H), 6.34 (d, J=16.4 Hz, 1H), 6.23 (s, 1H), 5.43 (s, 1H), 4.75 (br s, 2H), 4.57 (d, J=11.2 Hz, 1H), 4.28 (d, J=11.2 Hz, 1H), 4.14 (dd, J=11.5, 4.8 Hz, 1H), 3.99 (m, 1H), 3.87 (s, 3H), 3.86 (s, 3H), 3.73 (m, 3H), 3.51 (d, J=10.4 Hz, 1H), 3.47 (m, 1H), 3.14 (dd, J=10.1, 4.5 Hz, 1H), 2.56 (ddd, J=14.5, 6.3, 6.3 Hz, 1H), 2.35 (m, 3H), 2.11 (m, 2H), 2.00 (m, 2H), 1.82 (s, 3H), 1.80 (m, 2H), 1.68 (m, 1H), 1.51 (m, 2H), 1.26 (s, 3H), 1.05 (s, 9H), 0.97 (d, J=6.7 Hz, 3H), 0.80 (d, J=6.3 Hz, 3H); $^{13}$CNMR (125 MHz, CDCl$_3$) δ 161.1, 149.0, 148.6, 146.2, 141.8, 139.8, 135.9, 135.5, 135.3, 133.8, 131.0, 129.6, 127.64, 127.63, 127.61, 127.60, 120.2, 118.4, 111.1, 110.9, 110.4, 96.2, 87.5, 82.8, 81.0, 77.4, 77.2, 74.0, 69.9, 68.9, 67.8, 66.8, 60.7, 55.9, 55.8, 39.7, 39.6, 39.1, 36.4, 36.1, 33.5, 33.3, 30.7, 29.6, 26.8, 19.1, 13.5, 5.7; high resolution mass spectrum (ES$^+$) m/z 1032.3949 [(M+H)$^+$; calcd for C$_{54}$H$_{70}$INO$_9$SiH: 1032.3943].

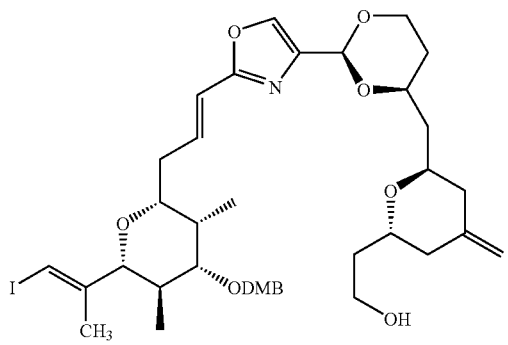

(+)-3.S$_5$

Primary Alcohol (+)-3.S$_5$:

Tetrabutylammonium fluoride (TBAF) (1.0 M/THF, 0.22 mL, 0.22 mmol) was added dropwise via syringe to a solution of (+)-3.53 (0.21 g, 0.20 mmol) in freshly distilled tetrahydrofuran (THF) (2 mL) at room temperature under an argon atmosphere. After two hours, the reaction was quenched via dropwise addition of saturated aqueous sodium chloride (10 mL). The layers of the biphasic solution were separated and the aqueous layer was extracted with EtOAc (7 mL, 4×). The combined organic extracts were dried over MgSO$_4$, filtered, and concentrated under reduced pressure. Purification via silica gel chromatography (80% EtOAc/hexanes) afforded primary alcohol (+)-3.S$_5$ (0.14 g, 89% yield) as a light yellow oil: [α]$_D$$^{20}$+37.6 (c 1.0, CHCl$_3$); IR (neat) 3407 (b), 3071 (w), 2940 (s), 2855 (s), 1659 (m), 1594 (w), 1516 (s), 1463 (m), 1420 (w), 1375 (w), 1263 (m), 1238 (m), 1139 (m), 1102 (s), 1030 (s), 973 (m), 808 (w), 754 (s), 668 (w) cm$^{-1}$; $^1$HNMR (500 MHz, CDCl$_3$) δ 7.60 (s, 1H), 6.86 (m, 3H) 6.68 (m, 1H), 6.34 (d, J=16.0 Hz, 1H), 6.22 (d, J=1.1 Hz, 1H), 5.56 (s, 1H), 4.79 (s, 1H), 4.74 (s, 1H), 4.56 (d, J=11.5 Hz, 1H), 4.27 (d, J=11.2 Hz, 1H), 4.24 (dd, J=11.1, 3.6 Hz, 1H), 4.10 (m, 1H), 4.01 (m, 1H), 3.94 (m, 2H), 3.87 (s, 3H), 3.87 (s, 3H), 3.74 (m, 2H), 3.5 (d, J=10.4 Hz, 1H), 3.46 (ddd, J=7.1, 7.1, 1.9 Hz, 1H), 3.14 (dd, J=10.4, 4.5 Hz, 1H), 2.75 (br s, 1H), 2.56 (m, 1H), 2.42 (dd, J=13.0, 4.8 Hz, 1H), 2.36 (m, 1H), 2.29 (dd, J=13.0, 4.1 Hz, 1H), 2.20 (ddd, J=14.9, 8.9, 6.3 Hz, 1H), 2.11 (m, 1H), 2.04 (m, 3H), 1.82 (m, 3H), 1.81 (d, J=1.1 Hz, 3H), 1.61 (m, 1H), 1.54 (m, 1H), 0.96 (d, J=7.1 Hz, 3H), 0.79 (d, J=6.3 Hz, 3H); $^{13}$CNMR (125 MHz, CDCl$_3$) δ 161.2, 149.0, 148.6, 146.2, 141.3, 139.7, 136.1, 135.4, 131.0, 120.2, 118.3, 111.1, 110.9, 110.7, 92.3, 87.5, 82.8, 80.9, 77.3, 74.7, 70.9, 69.8, 69.4, 66.9, 60.5, 55.9, 55.8, 40.1, 39.1, 38.2, 36.3, 36.1, 33.6, 33.3, 31.1, 19.1, 13.5, 5.6; high resolution mass spectrum (ES$^+$) m/z 816.2545 [(M+Na)$^+$; calcd for C$_{38}$H$_{52}$INO$_9$Na: 816.2585].

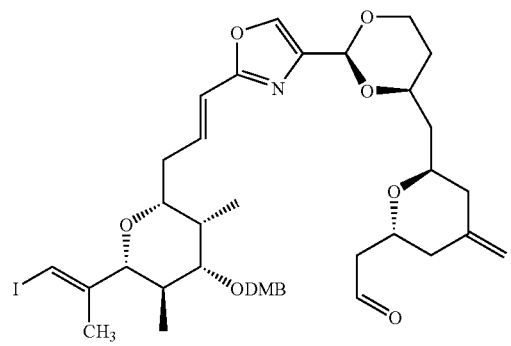

(+)-3.54

Aldehyde (+)-3.54:

Solid sodium bicarbonate (0.02 g, 0.20 mmol) followed by the Dess-Martin periodinane (0.17 g, 0.40 mmol) were added to a solution of primary alcohol (+)-3.S$_5$ (0.158 g, 0.20 mmol) in CH$_2$Cl$_2$ (75 mL) at 0° C. under an argon atmosphere. After stirring for ten minutes, the reaction was warmed to room temperature and after one hour and thirty minutes, the reaction was quenched via dropwise addition of saturated aqueous sodium bicarbonate (15 mL). The layers of the biphasic mixture were separated and the aqueous layer was extracted with CH$_2$Cl$_2$ (15 mL, 4×), dried over MgSO$_4$, filtered, and concentrated under reduced pressure. Purification via silica gel chromatography (70% EtOAc/hexanes) afforded aldehyde (+)-3.54 (0.135 g, 86% yield): [α]$_D$$^{20}$+36.5 (c 1.0, CHCl$_3$); IR (neat) 3151 (w), 3071 (w), 2934 (s), 2853 (s), 2726 (w), 1724 (s), 1659 (m), 1593 (m), 1516 (s), 1462 (m), 1420 (m), 1375 (m), 1263 (s), 1238 (s), 1156 (w), 1138 (s), 1101 (s), 1029 (s), 973 (m), 912 (m), 808 (w), 766 (w), 731 (s) cm$^{-1}$; $^1$HNMR (500 MHz, CDCl$_3$) δ 9.76 (dd, J=3.0, 1.5 Hz, 1H), 7.60 (s, 1H), 6.85 (m, 3H), 6.67 (m, 1H), 6.33 (d, J=16.0 Hz, 1H), 6.22 (d, J=1.1 Hz, 1H), 5.56 (s, 1H), 4.8 (s, 2H), 4.56 (d, J=11.2 Hz, 1H), 4.40 (dddd, J=8.9, 7.1, 4.5, 4.5 Hz, 1H), 4.27 (d, J=11.2 Hz, 1H), 4.23 (dd, J=11.1, 3.6 Hz, 1H), 3.96 (m, 3H), 3.87 (s, 3H), 3.86 (s, 3H), 3.50 (d, J=10.4 Hz, 1H), 3.46 (ddd, J=7.1, 7.1, 1.9 Hz, 1H), 3.14 (dd, J=10.4, 4.8 Hz, 1H), 2.70 (m, 1H), 2.53 (m, 1H), 2.47 (dd, J=16.4, 4.8 Hz, 1H), 2.37 (m, 3H), 2.15 (ddd, J=14.5, 9.3, 5.6 Hz, 1H), 2.10 (ddd, J=6.7, 4.8, 1.5 Hz, 1H), 2.03 (m, 2H), 1.80 (d, J=1.1 Hz, 3H), 1.77 (m, 1H), 1.56 (m, 2H), 1.25 (app t, J=7.1 Hz, 1H), 0.96 (d, J=7.1 Hz, 3H), 0.79 (d, J=6.3 Hz, 3H); $^{13}$CNMR (125 MHz, CDCl$_3$) δ 200.5, 161.2, 149.0, 148.6, 146.2, 140.5, 139.8, 136.0, 135.3, 130.9, 120.2, 118.4, 111.4, 111.1, 110.9, 96.3, 87.5, 82.8, 80.9, 77.3, 74.0, 69.9, 68.8, 67.2, 66.9, 55.9, 55.8, 47.1, 39.4, 39.2, 38.8, 36.1, 33.5, 33.3, 30.8, 19.1, 13.5, 5.7; high resolution mass spectrum (ES$^+$) m/z 814.2392 [(M+Na)$^+$; calcd for C$_{38}$H$_{50}$INO$_9$Na: 814.2428].

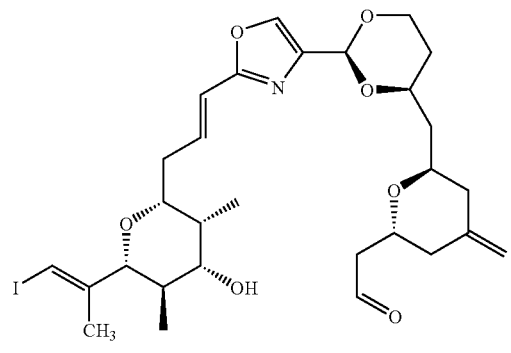

(+)-3.44

Secondary Alcohol-Aldehyde (+)-3.44:

2,3-Dichloro-5,6-dicyano-1,4-benzoquinone (DDQ) (0.079 g, 0.35 mmol) and pH 7 phosphate buffer (5.7 mL) were added to a solution of aldehyde (+)-3.54 (0.137 g, 0.17 mmol) in CH$_2$Cl$_2$ (24 mL) at room temperature under an argon atmosphere. After three hours and thirty minutes, the reaction mixture was poured into saturated aqueous sodium bicarbonate (20 mL). The layers of the biphasic mixture were separated and the aqueous layer was extracted with CH$_2$Cl$_2$ (15 mL, 4×). The combined organic extracts were dried over MgSO$_4$, filtered, and concentrated under reduced pressure. Purification via silica gel chromatography (80% EtOAc/hexanes) afforded secondary alcohol-aldehyde (+)-3.44 (0.108 g, 98% yield) as a light yellow oil: [α]$_D^{20}$+34.7 (c 1.0, CHCl$_3$); IR (neat) 3420 (b), 3151 (w), 3071 (w), 2924 (s), 2855 (s), 2726 (w), 1718 (s), 1654 (s), 1618 (w), 1541 (m), 1457 (m), 1279 (w), 1100 (s), 1012 (s), 892 (w), 755 (m), 671 (w) cm$^{-1}$; $^1$HNMR (500 MHz, CDCl$_3$) δ 9.76 (dd, J=3.0, 1.5 Hz, 1H), 7.59 (s, 1H), 6.66 (m, 1H), 6.33 (d, J=16.0 Hz, 1H), 6.23 (d, J=1.1 Hz, 1H), 5.55 (s, 1H), 4.80 (s, 2H), 4.40 (m, 1H), 4.23 (dd, J=11.2, 4.8 Hz, 1H), 3.95 (m, 3H), 3.51 (m, 1H), 3.50 (d, J=10.2 Hz, 1H), 3.43 (dd, J=10.4, 4.5 Hz, 1H), 2.70 (m, 1H), 2.54 (m, 1H), 2.50 (dd, J=16.4, 4.8, Hz, 1H), 2.48 (ddd, J=16.4, 4.8, 1.5 Hz, 2H), 2.32 (m, 1H), 2.12 (ddd, J=14.5, 9.3, 5.6 Hz, 1H), 2.03 (m, 2H), 1.9 (m, 1H), 1.81 (d, J=1.1 Hz, 3H), 1.60 (m, 5H), 0.95 (d, J=7.1 Hz, 3H), 0.81 (d, J=6.7 Hz, 3H); $^{13}$CNMR (125 MHz, CDCl$_3$) δ 200.5, 161.2, 146.0, 140.5, 139.8, 136.0, 135.3, 118.3, 111.4, 96.3, 87.3, 80.9, 77.6, 76.3, 74.0, 68.7, 67.2, 66.9, 47.6, 39.4, 39.2, 38.8, 38.0, 35.9, 34.5, 30.8, 19.2, 13.1, 5.4; high resolution mass spectrum (ES$^+$) m/z 642.1911 [(M+H)$^+$; calcd for C$_{29}$H$_{40}$INO$_7$H: 642.1928].

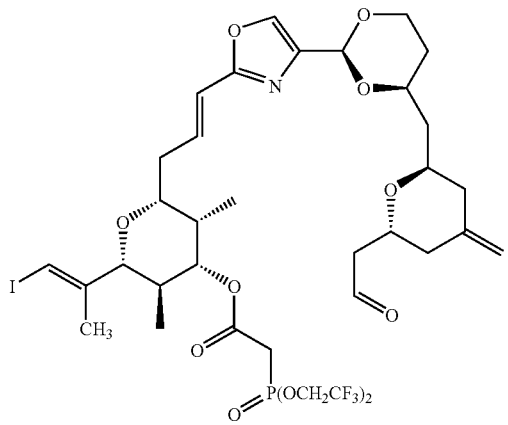

(+)-3.S$_6$

Phosphonate Ester (+)-3.S$_6$:

A solution of bis-(2,2,2-trifluoroethyl)phosphonate acid 3.45 (0.522 g, 1.72 mmol) in CH$_2$Cl$_2$ (30 mL) was added via cannula to a solution of secondary alcohol-aldehyde (+)-3.44 (0.221 g, 0.34 mmol) in CH$_2$Cl$_2$ (40 mL) at room temperature under an argon atmosphere. After stirring for ten minutes, 1-[3-(dimethylamino)propyl]-3-ethylcarbodiimide-methiodide (EDCI.MeI) (0.511 g, 1.72 mmol) and 1-hydroxybenzotriazole (HOBT) (0.005 g, 0.03 mmol) were added to the reaction mixture. After forty-five minutes, the reaction was filtered through a plug of silica gel (80% EtOAc/hexanes) to afford phosphonate ester (+)-3.S$_6$ (0.261 g, 82% yield) as a light yellow oil: [α]$_D^{20}$+17.6 (c 1.0, CHCl$_3$); IR (neat) 3077 (w), 2924 (s), 2855 (m), 2726 (w), 1728 (s), 1656 (w), 1624 (w), 1539 (w), 1419 (m), 1397 (w), 1305 (s), 1267 (s), 1173 (s), 1098 (s), 1070 (s), 1040 (m), 963 (m), 893 (m) cm$^{-1}$; $^1$HNMR (500 MHz, CDCl$_3$) δ 9.76 (dd, J=3.0, 1.5 Hz, 1H), 7.59 (s, 1H), 6.63 (m, 1H), 6.31 (d, J=16.0 Hz, 1H), 6.28 (s, 1H), 5.55 (s, 1H), 4.81 (s, 2H), 4.74 (dd, J=11.2, 4.5 Hz, 1H), 4.43 (m, 5H), 4.24 (dd, J=11.2, 4.8 Hz, 1H), 3.98 (m, 1H), 3.93 (m, 2H), 3.58 (d, J=10.1 Hz, 1H), 3.56 (m, 1H), 3.20 (s, 1H), 3.16 (s, 1H), 2.70 (m, 1H), 2.56 (m, 1H), 2.48 (dd, J=16.0, 4.8 Hz, 1 H), 2.40 (ddd, J=13.0, 4.6, 4.5 Hz, 2H), 2.28 (m, 1H), 2.16 (ddd, J=14.1, 9.3, 5.6 Hz, 1H), 2.09 (m, 1H), 2.04 (dd, J=13.4, 6.0 Hz, 2H), 1.91 (m, 1H), 1.83 (s, 3H), 1.79 (m, 2H), 1.56 (m, 1H), 0.96 (d, J=7.1 Hz, 3H), 0.72 (d, J=6.7 Hz, 3H); $^{13}$CNMR (125 MHz, CDCl$_3$) δ 200.5, 163.9, 161.0, 145.3, 140.5, 139.8, 135.4, 135.3, 118.6, 111.4, 96.3, 87.1, 81.7, 80.5, 76.7, 74.0, 68.7, 67.2, 66.9, 62.7, 62.4, 47.6, 39.4, 39.2, 38.8, 35.8, 35.3, 34.6, 33.5, 32.0, 30.8, 29.6, 19.1, 12.9, 6.0; high resolution mass spectrum (ES$^+$) m/z 928.1787 [(M+H)$^+$; calcd for C$_{35}$H$_{45}$F$_6$INO$_{11}$PH: 928.1757].

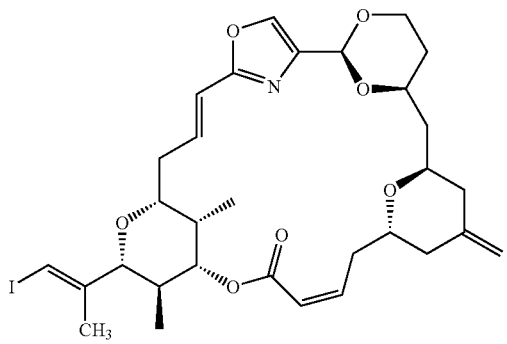

(+)-3.43Z

Z-C(2-3) Macrocycle (+)-3.43Z:

18-Crown-6 (3.98 g, 15.1 mmol) and solid potassium carbonate (0.446 g, 3.23 mmol) were added to a flask charged with freshly distilled toluene (195 mL) at room temperature under an argon atmosphere. After stirring for three hours, a solution of phosphonate ester (+)-3.S$_6$ (0.25 g, 0.27 mmol) in freshly distilled toluene (170 mL) was added dropwise via cannula and allowed to stir at room temperature. After two hours, the reaction mixture was poured into saturated aqueous sodium chloride (100 mL) and the layers of the resultant biphasic mixture were separated. The aqueous layer was extracted with EtOAc (30 mL, 4×), dried over MgSO$_4$, filtered and concentrated under reduced pressure. Purification via silica gel chromatography afforded Z-C(2-3) macrocycle (+)-3.43Z (0.102 g, 57% yield) and E-C(2-3) macrocycle (+)-3.43E (0.052 g, 29% yield) both as off white foams: Z-C(2-3) Macrocycle (+)-3.43Z: [α]$_D^{20}$+25.7 (c 0.2, CHCl$_3$); IR (neat) 2923 (s), 2843 (s), 1717 (s), 1653 (m), 1557 (w), 1456 (w), 1280 (m), 1192 (m), 1149 (m), 1091 (s), 1018 (m), 886 (w), 667 (s) cm$^{-1}$; $^1$HNMR (500 MHz, C$_6$D$_6$) δ 7.61 (s, 1H), 6.92 (m, 1H), 6.15 (d, J=15.9 Hz, 1H), 6.11 (s, 1H), 5.87 (dd, J=10.2, 2.0 Hz, 1H), 5.55 (ddd, J=10.2, 10.1, 3.0 Hz, 1H), 5.45 (d, J=0.9 Hz, 1H), 5.26 (s, 1H), 4.85 (s, 1H), 4.57 (dd, J=11.2, 4.4 Hz, 1H), 4.40 (m, 1H), 4.16 (dd, J=11.8, 6.1 Hz, 1H), 4.01 (dd, J=15.8, 11.3, 11.1 Hz, 1H), 3.91 (dd, J=11.7, 4.4 Hz, 1H), 3.59 (app t, J=11.1 Hz, 1H), 3.46 (ddd, J=12.1, 11.7, 2.5 Hz, 1H), 3.34 (d, J=10.1 Hz, 1H), 3.34 (m, 1H), 2.91 (d, J=12.2 Hz, 1H), 2.67 (app t, J=6.3 Hz, 1H), 2.51 (m, 2H), 2.36 (m, 2H), 2.09 (m, 1H), 2.08 (d, J=12.7 Hz, 1H), 2.02 (d, J=11.2 Hz, 1H), 1.94 (m, 1H), 1.88 (d, J=0.9 Hz, 3H), 1.55 (m, 2H), 1.02 (d, J=6.9 Hz, 3H), 0.84 (d, J=13.4 Hz, 1H), 0.68

(d, J=6.5 Hz, 3H); $^{13}$CNMR (125 MHz, CDCl$_3$) δ 165.5, 161.1, 145.7, 144.4, 141.4, 139.6, 134.6, 134.1, 120.8, 119.1, 110.1, 97.0, 87.6, 81.7, 79.1, 78.2, 76.7, 73.2, 68.2, 67.0, 41.1, 39.0, 36.8, 34.1, 32.5, 31.8, 30.3, 29.6, 19.1, 13.0, 5.7; high resolution mass spectrum (ES$^+$) m/z 688.1736 [(M+Na)$^+$; calcd for C$_{31}$H$_{40}$INO$_7$Na: 688.1747].

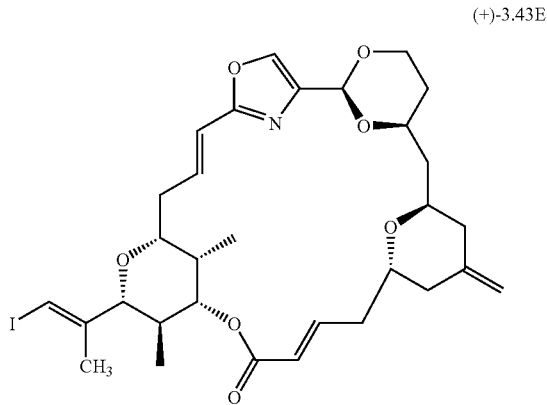

(+)-3.43E

E-C(2-3) Macrocycle (+)-3.43E: (0.075 g, 42% yield) [α]$_D^{20}$+84.6 (c 2.9, CHCl$_3$); IR (neat) 2926 (b), 2853 (b), 1720 (s), 1656 (s), 1153 (s), 1097 (s), 1010 (b), 755 (s); $^1$HNMR (500 MHz, C$_6$D$_6$) δ 7.32 (s, 1H), 6.68 (m, 1H), 6.08 (d, J=16.0 Hz, 1H), 6.03 (d, J=15.4 Hz, 1H), 5.98 (s, 1H), 5.34 (s, 1H), 4.97 (dd, J=11.1, 4.3 Hz, 1H), 4.72 (s, 1H); 4.66 (s, 1H), 4.18 (m, 1H), 3.85 (dd, J=11.4, 3.8 Hz, 1H), 3.36 (m, 2H), 3.23 (m, 2H), 3.17 (app t, J=9.9 Hz, 1H), 2.25 (m, 2H), 2.11 (m, 3H), 1.91 (dd, J=13.0, 3.1 Hz, 1H), 1.83 (m, 2H), 1.76 (s, 3H), 1.69 (m, 4H), 0.92 (app t, J=7.1 Hz, 1H), 0.88 (app t, J=7.0 Hz, 1H), 0.86 (d, J=6.7 Hz, 3H), 0.75 (app t, J=7.1 Hz, 1H), 0.67 (d, J=6.5 Hz, 3H); $^{13}$CNMR (125 MHz, C$_6$D$_6$) δ 166.8, 161.9, 147.0, 146.6, 142.2, 141.1, 135.6, 123.8, 119.1, 111.2, 95.6, 87.8, 81.2, 78.6, 77.4, 73.6, 70.5, 69.6, 66.6, 40.9, 40.7, 38.6, 38.2, 34.7, 32.6, 31.9, 30.4, 19.4, 13.2, 6.2, 1.5; high resolution mass spectrum (ES$^+$) m/z 688.0859 [(M+Na)$^+$; calcd for C$_{31}$H$_{40}$INO$_7$Na: 688.0850].

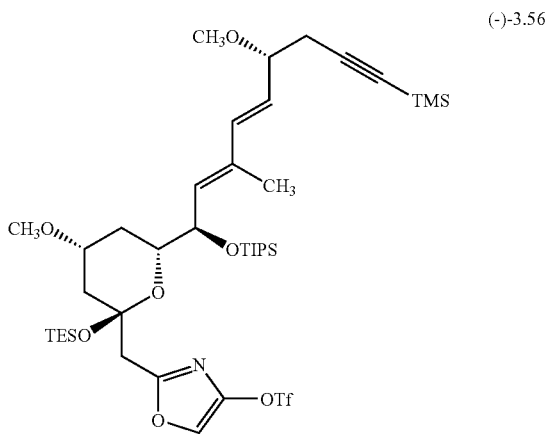

(-)-3.56

C(33)-TES Acetal Side Chain (-)-3.56:

Oxazole 2.9 (0.74 g, 2.38 mmol) was added to a solution of dienyl lactone (-)-2.80 Smith, et al. *J. Am. Chem. Soc.* 2001, 123, 10942) (0.255 g, 0.47 mmol) in freshly distilled tetrahydrofuran (THF) (22.4 mL) at room temperature under an argon atmosphere. After cooling to 0° C., iso-propylmagnesium chloride (i-PrMgCl) (2.0 M/THF, 0.59 mL, 1.20 mmol) was added dropwise over thirty minutes followed by stirring for twenty minutes. Additional i-PrMgCl (2.0 M/THF, 0.59 mL, 1.20 mmol) was added dropwise over thirty minutes and allowed to stir for twenty minutes. A final addition of i-PrMgCl (2.0 M/THF, 0.59 mL, 1.20 mmol) was added dropwise over thirty minutes and after stirring for twenty minutes, the reaction was quenched via dropwise addition of saturated aqueous sodium bicarbonate (10 mL). The layers of the biphasic solution were separated and the aqueous layer was extracted with EtOAc (10 mL, 3×). The combined organic extracts were dried over MgSO$_4$, filtered, and concentrated under reduced pressure. The resultant light orange oil was filtered through a plug of silica gel (30% EtOAc/hexanes) to afford the corresponding hemi-acetal, which was immediately dissolved in freshly distilled diethyl ether (1.4 mL) and anhydrous acetonitrile (1.0 mL). After cooling to -78° C. under an argon atmosphere, 2,6-lutidine (0.425 mL, 3.66 mmol) was added followed by dropwise addition of triethylsilyl trifluoromethanesulfonate (TESOTf) (0.278 mL, 1.22 mmol). After twenty-four hours, the reaction was quenched via dropwise addition of saturated aqueous sodium bicarbonate (3 mL) and allowed to warm to room temperature. The layers of the biphasic solution were separated and the aqueous layer was extracted with CH$_2$Cl$_2$ (5 mL, 3×). The combined organic extracts were dried over MgSO$_4$, filtered, and concentrated under reduced pressure. Purification via silica gel chromatography (5% EtOAc/hexanes) afforded C(33)-TES acetal side chain (-)-3.56 (0.224 g, 54% yield, 2 steps) as a colorless oil: [α]$_D^{20}$-8.4 (c 0.1, CHCl$_3$); IR (neat) 2958 (b), 2868 (b), 2179 (s), 1591 (s), 1434 (s), 1231 (b), 1139 (s), 1094 (s), 1000 (s), 853 (s), 606 (s); $^1$HNMR (500 MHz, C$_6$D$_6$) δ 7.14 (s, 1H), 6.25 (d, J=15.7 Hz, 1H), 5.73 (dd, J=15.7, 7.3 Hz, 1H), 5.53 (d, J=8.9 Hz, 1H), 4.83 (dd, J=8.9, 4.9 Hz, 1H), 4.09 (m, 1H), 3.71 (m, 1H), 3.66 (dd, J=9.9, 4.2 Hz, 1H), 3.27 (dd, J=13.9, 7.0 Hz, 1H), 3.15 (s, 3H), 3.13 (s, 3H), 2.87 (d, J=14.2 Hz, 1H), 2.79 (d, J=14.3 Hz, 1H), 2.55 (dd, J=16.8, 5.3 Hz, 1H), 2.43 (dd, J=16.7, 6.7 Hz, 1H), 2.37 (dd, J=10.3, 2.0 Hz, 1H), 2.26 (ddd, J=14.0, 4.1, 1.4 Hz, 1H), 1.83 (s, 3H), 1.66 (app t, J=11.4 Hz, 1H), 1.12 (m, 21H), 1.00 (app t, J=7.9 Hz, 9H), 0.65 (app q, J=7.9 Hz, 6H), 0.22 (s, 9H); $^{13}$CNMR (125 MHz, C$_6$D$_6$) δ 159.0, 144.9, 137.1 134.8, 132.6, 104.1, 99.3, 86.6, 80.6, 74.3, 73.9, 70.9, 65.9, 56.4, 55.1, 42.3, 41.4, 31.4, 27.1, 18.3, 18.2, 15.5, 13.5, 12.8, 7.2, 6.6, 0.22; high resolution mass spectrum (ES$^+$) m/z 904.3924 [(M+Na)$^+$; calcd for C$_{40}$H$_{70}$F$_3$NO$_9$SSi$_3$Na: 904.3927].

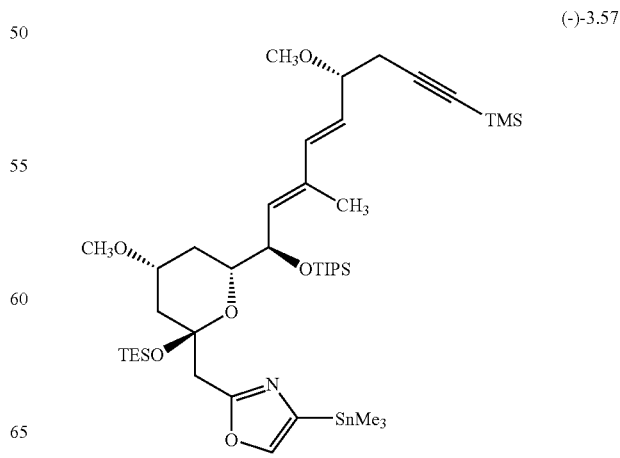

(-)-3.57

C(33)-TES Stannyl Side Chain (−)-3.57:

C(33)-TES acetal side chain (−)-3.56 (0.028 g, 0.033 mmol) was combined with hexamethylditin [(Me$_3$Sn)$_2$] (0.015 g, 0.046 mmol) in a sealed tube (100 mL), azeotroped from benzene (2 mL, 3×), and dried under vacuum for thirty minutes. Flame dried lithium chloride (LiCl) (0.022 g, 0.52 mmol), tetrakis(triphenylphosphine)palladium [Pd(PPh$_3$)$_4$] (5.6 mg, 0.005 mmol) and anhydrous dioxane (0.50 mL, freeze pump thawed, 3×) were added to the tube in a glove bag, under an argon atmosphere. The tube was sealed and heated to 90° C. with stirring behind a blast shield. After thirteen hours, the reaction mixture was cooled to room temperature and concentrated under reduced pressure. The resultant dark brown slurry was purified via silica gel chromatography (5% EtOAc/hexanes) to afford C(33)-TES stannyl side chain (−)-3.57 (0.016 g, 55% yield) as a colorless oil: $[\alpha]_D^{20}$−31.1 (c 0.1, CHCl$_3$); IR (neat) 2957 (b), 1462 (s), 1248 (s), 1095 (b), 1000 (s), 843 (s), 743 (b); $^1$HNMR (500 MHz, C$_6$D$_6$) δ 7.36 (s, 1H), 6.32 (d, J=15.7 Hz, 1H), 5.75 (dd, J=15.7, 7.3 Hz, 1H), 5.64 (d, J=8.7 Hz, 1H), 4.90 (dd, J=8.6, 4.8 Hz, 1H), 4.18 (dd, J=11.9, 4.7 Hz, 1H), 3.79 (m, 1H), 3.69 (dd, J=13.1, 6.8 Hz, 1H), 3.28 (d, J=14.4 Hz, 1H), 3.23 (d, J=14.3 Hz, 1H), 3.14 (s, 3H), 3.13 (s, 3H), 2.58 (dd, J=16.7, 5.5 Hz, 1H), 2.51 (dd, J=12.5, 4.2 Hz, 1H), 2.44 (dd, J=16.7, 6.9 Hz, 1H), 2.39 (d, J=12.3 Hz, 1H), 1.90 (s, 3H), 1.76 (app t, J=12.2 Hz, 1H), 1.34 (m, 1H), 1.16 (m, 21H), 1.06 (app t, J=7.9 Hz, 9H), 0.76 (app q, J=15.7 Hz, 6H), 0.27 (s, 9H), 0.23 (s, 9H); $^{13}$CNMR (125 MHz, C$_6$D$_6$) δ 161.7, 145.6, 137.7, 135.1, 133.5, 104.6, 100.3, 86.9, 81.1, 74.8, 74.5, 71.8, 56.8, 55.5, 42.8, 42.3, 32.2, 30.6, 27.8, 18.7, 18.6, 14.1, 13.2, 7.7, 7.1, 0.6, −9.3; high resolution mass spectrum (ES$^+$) m/z 920.4139 [(M+Na)$^+$; calcd for C$_{42}$H$_{79}$NO$_6$Si$_3$SnNa: 920.4012].

Protected Z-C(2-3) Acetal Alkynyl Phorboxazole (+)-3.S$_7$Z:

Z-C(2-3) macrocycle (+)-3.43Z (3.9 mg, 0.006 mmol) was combined with C(33)-TES stannyl side chain (−)-3.57 (7.8 mg, 0.009 mmol) in a flame-dried round-bottom flask (5 mL), azeotroped from benzene (1 mL, 3×) and dried under vacuum for two hours. Tris(dibenzylideneacetone)dipalladium-chloroform adduct [Pd$_2$(dba)$_3$·CHCl$_3$] (1.2 mg, 0.001 mmol), triphenylarsine (AsPh$_3$) (2.2 mg, 0.007 mmol), and Ph$_2$PO$_2$NBu$_4$ (4.1 mg, 0.009 mmol) followed by DMF (0.1 mL, sparged with argon for thirty minutes) and N,N-diisopropylethylamine (0.001 mL, 0.006 mmol) were added to the flask and the reaction stirred at room temperature under an argon atmosphere. After seventeen hours, the light brown reaction mixture was introduced directly onto a silica gel column (25% EtOAc/hexanes) to afford protected Z-C(2-3) acetal alkynyl phorboxazole (+)-3.S$_7$Z (5.2 mg, 68% yield) as a light yellow oil: $[\alpha]_D^{20}$+6.7 (c 0.3, CHCl$_3$); IR (neat) 2924 (b), 1720 (s), 1651 (w), 1463 (s), 1376 (w), 1247 (w), 1091 (s), 1018 (b), 843 (s), 742 (w); $^1$HNMR (500 MHz, C$_6$D$_6$) δ 7.52 (s, 1H), 7.33 (s, 1H), 6.89 (m, 1H), 6.38 (s, 1H), 6.31 (d, J=15.7 Hz, 1H), 6.09 (d, J=15.7 Hz, 1H), 5.81 (dd, J=11.4, 2.5 Hz, 1H), 5.74 (dd, J=15.7, 7.3 Hz, 1H), 5.63 (d, J=8.9 Hz, 1H), 5.47 (ddd, J10.2, 10.2, 3.1 Hz, 1H), 5.38 (s, 1H), 5.19 (s, 1H), 4.90 (dd, J=8.5, 4.6 Hz, 1H), 4.79 (s, 1H), 4.62 (dd, J=11.2, 4.5 Hz, 1H), 4.34 (br s, 1H), 4.28 (m, 1H), 4.08 (m, 1H), 3.95 (m, 1H), 3.82 (m, 2H), 3.70 (dd, J=13.3, 6.8 Hz, 1H), 3.51 (app t, J=10.8 Hz, 1H), 3.45 (d, J=10.0 Hz, 1H), 3.37 (m, 2H), 3.17 (d, J=2.5 Hz, 1H), 3.16 (s, 3H), 3.13 (s, 3H), 2.83 (d, J=12.6 Hz, 1H), 2.67 (m, 1H), 2.59 (dd, J=16.7, 5.7 Hz, 1H), 2.49 (m, 2H), 2.40 (m, 4H), 2.15 (s, 3H), 2.10 (m, 2H), 2.03 (m, 3H), 1.95 (app t, J=11.8 Hz, 1H), 1.90 (s, 3H), 1.51 (m, 4H), 1.15 (m, 21H), 1.06 (app t, J=7.9 Hz, 9H), 1.04 (d, J=6.9 Hz, 3H), 0.93 (m, 1H), 0.79 (d, J=6.4 Hz, 3H), 0.75 (app q, J=8.1 Hz, 6H), 0.23 (s, 9H); $^{13}$CNMR (125 MHz, C$_6$D$_6$) δ 165.4, 161.4, 159.8, 144.9, 142.5, 140.9, 138.7, 137.7, 137.3, 136.6, 134.7, 134.3, 133.0, 121.1, 119.4, 119.1, 110.2, 99.8, 97.5, 89.6, 86.5, 80.7, 80.0, 78.5, 74.4, 74.1, 73.4, 73.3, 71.3, 68.9, 66.8, 56.4, 55.1, 42.4, 41.8, 41.4, 39.8, 37.5, 34.5, 32.8, 31.8, 30.7, 30.2, 30.1, 27.5, 22.9, 18.4, 18.3, 14.2, 13.7, 13.4, 12.8, 7.3, 7.0, 6.7, 6.1, 2.3; high resolution mass spectrum (ES$^+$) m/z 1293.7257 [(M+Na)$_+$; calcd for C$_{70}$H$_{110}$N$_2$O$_{13}$Si$_3$Na: 1293.7212].

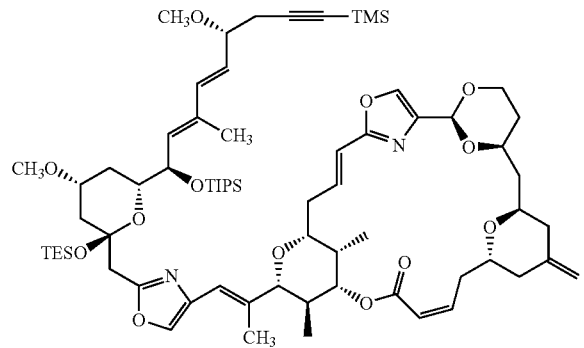

(+)-3.S$_7$Z

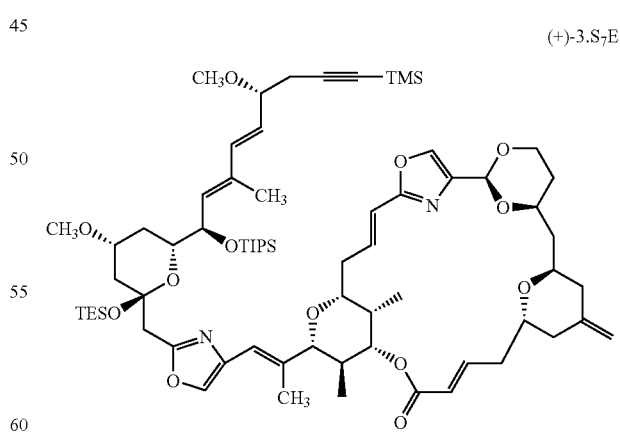

(+)-3.S$_7$E

Protected E-C(2-3) Acetal Alkynyl Phorboxazole (+)-3.S$_7$E:

E-C(2-3) macrocycle (+)-3.43E (4.6 mg, 0.007 mmol) was combined with C(33)-TES stannyl side chain (−)-3.57 (9.2 mg, 0.010 mmol) in a flame-dried round-bottom flask (5 mL), azeotroped from benzene (1 mL, 3×) and dried under vacuum for two hours. Tris(dibenzylideneacetone)dipalladium-chloroform adduct [$Pd_2(dba)_3 \cdot CHCl_3$] (1.4 mg, 0.001 mmol), triphenylarsine ($AsPh_3$) (2.5 mg, 0.008 mmol), and $Ph_2PO_2NBu_4$ (4.7 mg, 0.01 mmol) followed by DMF (0.13 mL, sparged with argon for thirty minutes) and N,N-diisopropylethylamine (0.002 mL, 0.01 mmol) were added to the flask and the reaction stirred at room temperature under an argon atmosphere. After twenty hours, the light brown reaction mixture was introduced directly onto a silica gel column (40% EtOAc/hexanes) to afford protected E-C(2-3) acetal alkynyl phorboxazole (+)-3.$S_7$E (5.3 mg, 60% yield) as a light yellow oil. $[\alpha]_D^{20}$+2.7 (c 0.1, $CHCl_3$); IR (neat) 2929 (b), 2866 (b), 1717 (s), 1652 (w), 1464 (s), 1247 (s), 1153 (s), 1099 (s), 1009 (b), 842 (s), 742 (s); $^1$HNMR (500 MHz, $C_6D_6$) δ 7.33 (s, 1H), 7.30 (s, 1H), 6.70 (m, 1H), 6.33 (s, 1H), 6.30 (d, J=15.7 Hz, 1H), 6.11 (d, J=16.1 Hz, 1H), 6.05 (d, J=15.4 Hz, 1H), 5.73 (dd, J=15.7, 7.4 Hz, 1H), 5.63 (d, J=8.9 Hz, 1H), 5.36 (s, 1H), 5.09 (dd, J=11.1, 4.2 Hz, 1H), 4.89 (dd, J=8.6, 4.7 Hz, 1H), 4.72 (s, 1H), 4.66 (s, 1H), 4.16 (m, 2H), 3.86 (dd, J=11.6, 4.5 Hz, 1H), 3.81 (m, 1H), 3.69 (dd, J=13.1, 6.7 Hz, 1H), 3.43 (d, J=9.9 Hz, 1H), 3.37 (m, 3H), 3.18 (m, 1H), 3.15 (s, 3H), 3.12 (s, 3H), 2.58 (dd, J=16.7, 5.7 Hz, 1H), 2.48 (m, 2H), 2.39 (m, 2H), 2.25 (m, 3H), 2.16 (m, 2H), 2.11 (s, 3H), 1.92 (dd, J=12.9, 3.1 Hz, 1H), 1.89 (s, 3H), 1.84 (app t, J=12.3 Hz, 1H), 1.82 (m, 1H), 1.72 (m, 3H), 1.49 (m, 3H), 1.33 (m, 4H), 1.17 (m, 21H), 1.05 (app t, J=7.9 Hz, 9H), 0.95 (d, J=6.7 Hz, 3H), 0.86 (d, J=6.5 Hz, 3H), 0.75 (app q, J=7.8 Hz, 6H), 0.23 (s, 9H); $^{13}$CNMR (125 MHz, $C_6D_6$) δ 183.0, 170.4, 166.7, 161.7, 159.7, 146.6, 142.1, 140.9, 138.7, 137.8, 137.3, 136.5, 135.7, 135.4, 134.7, 132.9, 131.8, 126.7, 123.7, 118.9, 118.8, 110.9, 104.4, 99.8, 95.5, 89.6, 86.5, 80.7, 78.9, 77.1, 74.4, 74.1, 73.3, 71.4, 70.3, 66.4, 56.4, 55.1, 42.4, 41.8, 40.9, 40.4, 38.5, 34.7, 34.6, 31.8, 30.2, 27.5, 18.4, 18.3, 14.2, 13.7, 13.4, 12.8, 7.4, 6.7, 0.3; high resolution mass spectrum (ES$^+$) m/z 1293.7274 [(M+Na)$^+$; calcd for $C_{70}H_{110}N_2O_{13}Si_3Na$: 1293.7212].

rahydrofuran (THF) (1.3 mL) under argon at 0° C. After stirring for five minutes tetrabutylammonium fluoride (TBAF) (1.0 M/THF, 0.021 mL, 0.02 mmol) was added dropwise via syringe. After one hour, the reaction was quenched via dropwise addition of saturated aqueous sodium bicarbonate (1.5 mL) and warmed to room temperature. The layers of the biphasic mixture were separated and the aqueous layer was extracted with EtOAc (3 mL, 4×). The combined organic extracts were dried over $MgSO_4$, filtered and concentrated under reduced pressure. Purification via silica gel chromatography (100% EtOAc) afforded Z-C(2-3) C(11-15)-acetal alkynyl phorboxazole (+)-3.42Z (3.7 mg, 80% yield) as an amorphous solid. $[\alpha]_D^{20}$+37.4 (c 0.1, $CHCl_3$); IR (neat) 3356 (b), 2940 (b), 2356 (w), 1712 (s), 1455 (s), 1365 (s), 1230 (s), 1175 (s), 903 (s), 848 (s), 735 (s); $^1$HNMR (500 MHz, $C_6D_6$) δ 7.53 (s, 1H), 7.03 (s, 1H), 6.90 (m, 1H), 6.23 (d, J=15.9 Hz, 1H), 6.21 (s, 1H), 6.11 (d, J=15.9 Hz, 1H), 5.82 (dd, J=11.5, 2.2 Hz, 1H), 5.59 (dd, J=15.7, 7.6 Hz, 1H), 5.56 (d, J=8.9 Hz, 1H), 5.45 (ddd, J=13.1, 10.1, 3.0 Hz, 1H), 5.38 (d, J=0.7 Hz, 1H), 5.20 (s, 1H), 4.80 (s, 1H), 4.62 (dd, J=11.2, 4.3 Hz, 1H), 4.35 (m, 2H), 4.08 (m, 1H), 3.96 (m, 2H), 3.83 (dd, J=11.4, 4.5 Hz, 1H), 3.78 (m, 1H), 3.63 (dd, J=13.7, 6.6 Hz, 1H), 3.51 (app t, J=11.2 Hz, 1H), 3.40 (app t, J=9.9 Hz, 1H), 3.39 (m, 1H), 3.09 (s, 3H), 3.07 (s, 3H), 2.84 (d, J=15.2 Hz, 1H), 2.69 (d, J=15.1 Hz, 1H), 2.68 (m, 1H), 2.46 (m, 1H), 2.40 (m, 5H), 2.31 (dd, J=6.6, 2.7 Hz, 1H), 2.28 (dd, J=11.2, 3.0 Hz, 1H), 2.00 (m, 4H), 1.95 (s, 3H), 1.78 (app t, J=2.7 Hz, 1H), 1.65 (d, J=0.9 Hz, 3H), 1.51 (m, 3H), 1.31 (m, 4H), 1.05 (d, J=6.9 Hz, 3H), 0.9 (m, 2H), 0.7 (d, J=6.4 Hz, 3H); $^{13}$CNMR (125 MHz, $C_6D_6$) δ 161.0, 145.3, 142.7, 141.1, 138.9, 137.7, 137.1, 136.1, 134.9, 134.3, 131.8, 129.8, 121.2, 119.7, 118.5, 110.1, 97.7, 97.1, 89.5, 80.9, 80.1, 78.7, 73.6, 73.5, 73.1, 71.2, 70.5, 69.1, 67.0, 56.5, 55.5, 41.6, 41.3, 41.2, 40.0, 37.7, 35.8, 34.7, 33.7, 33.0, 32.3, 32.2, 30.9, 30.4, 30.3, 30.1, 29.9, 26.4, 25.8, 14.5, 13.5, 6.3; high resolution mass spectrum (ES$^+$) m/z 951.4637 [(M+Na)$^+$; calcd for $C_{52}H_{68}N_2O_{13}Na$: 951.4618].

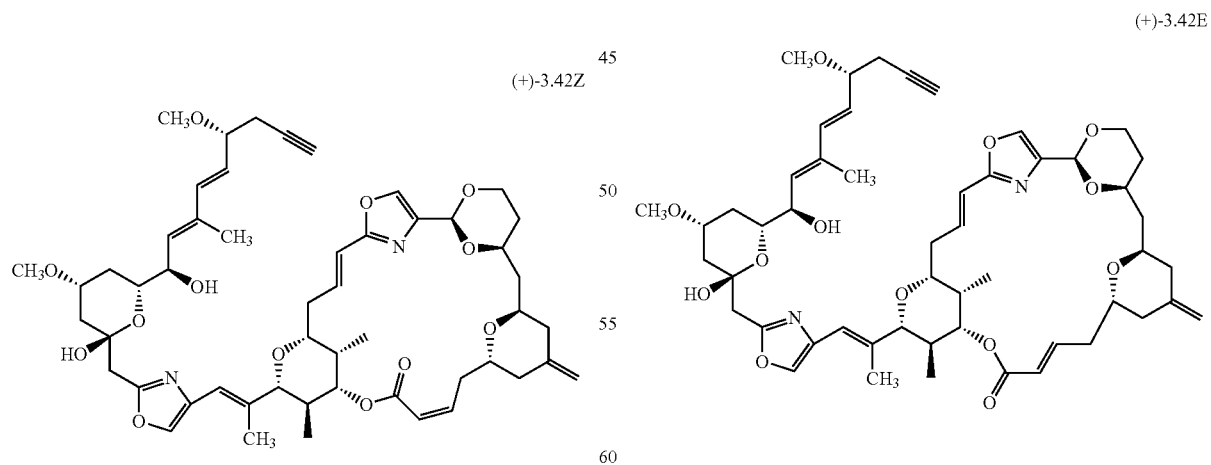

(+)-3.42Z (+)-3.42E

Z-C(2-3) C(11-15)-Acetal Alkynyl Phorboxazole (+)-3.42Z:

Protected Z-C(2-3) acetal alkynyl phorboxazole (+)-3.$S_7$Z (6.7 mg, 0.005 mmol) was dissolved in freshly distilled tet- E-C(2-3) C(11-15)-Acetal Alkynyl Phorboxazole (+)-3.42E:

Protected E-C(2-3) acetal alkynyl phorboxazole (+)-3.$S_7$E (0.010 g, 0.008 mmol) was dissolved in freshly distilled tetrahydrofuran (THF) (1.9 mL) under argon at 0° C. After stirring for five minutes, tetrabutylammonium fluoride (TBAF) (1.0 M/THF, 0.031 mL, 0.03 mmol) was added dropwise via syringe. After one hour, the reaction was quenched via dropwise addition of saturated aqueous sodium bicarbonate (2.0 mL) and allowed to warm to room temperature. The layers of the biphasic mixture were separated and the aqueous layer was extracted with EtOAc (3 mL, 4×), dried over MgSO$_4$, filtered and concentrated under reduced pressure. Purification via silica gel chromatography (100% EtOAc) afforded E-C(2-3) C(11-15)-acetal alkynyl phorboxazole (+)-3.42E (6.0 mg, 81% yield) as an amorphous solid. $[\alpha]_D^{20}$+21.8 (c 0.1, CH$_2$Cl$_2$), IR (neat) 3305 (b), 2926 (b), 2853 (s), 1714 (s), 1655 (s), 1456 (b), 1362 (b), 1153 (s), 1097 (s), 1010 (b), 879 (w); $^1$HNMR (500 MHz, C$_6$D$_6$) δ 7.40 (s, 1H), 7.31 (s, 1H), 6.83 (m, 1H), 6.31 (d, J=15.8 Hz, 1H), 6.26 (s, 1H), 6.22 (d, J=16.1 Hz, 1H), 6.16 (d, J=15.4 Hz, 1H), 5.67 (dd, J=15.6, 7.5 Hz, 1H), 5.64 (d, J=8.8 Hz, 1H), 5.52 (s, 1H), 5.45 (s, 1H), 5.19 (dd, J=11.1, 4.1 Hz, 1H), 4.82 (s, 1H), 4.75 (s, 1H), 4.43 (app t, J=7.3 Hz, 1H), 4.29 (m, 1H), 4.05 (dd, J=10.2, 4.5 Hz, 1H), 3.95 (dd, J=11.7, 4.5 Hz, 1H), 3.87 (m, 1H), 3.72 (dd, J=14.1, 7.3 Hz, 1H), 3.47 (m, 3H), 3.28 (app t, J=10.2 Hz, 1H), 3.18 (s, 3H), 3.16 (s, 3H), 2.92 (d, J=15.4 Hz, 1H), 2.78 (d, J=15.4 Hz, 1H), 2.55 (dd, J=5.8, 2.7 Hz, 1H), 2.52 (dd, J=5.8, 2.6 Hz, 1H), 2.50 (m, 1H), 2.44 (dd, J=6.6, 2.7 Hz, 1H), 2.40 (dd, J=6.7, 2.8 Hz, 1H), 2.34 (m, 4H), 2.18 (m, 2H), 2.11 (m, 1H), 2.04 (m, 2H), 1.99 (s, 3H), 1.92 (m, 1H), 1.87 (app t, J=2.6 Hz, 1H), 1.81 (m, 3H), 1.74 (s, 3H), 1.61 (m, 2H), 1.36 (m, 3H), 1.07 (d, J=6.7 Hz, 3H), 1.01 (m, 2H), 0.92 (d, J=6.5 Hz, 1H); $^{13}$CNMR (125 MHz, C$_6$D$_6$) δ 167.3, 162.4, 161.3, 147.3, 142.6, 141.5, 139.4, 138.7, 138.1, 137.4, 136.4, 136.3, 135.9, 132.2, 124.3, 119.5, 118.8, 111.5, 97.4, 96.1, 89.9, 81.5, 81.2, 79.4, 77.8, 73.9, 73.4, 71.6, 70.9, 66.9, 56.8, 55.9, 41.7, 41.4, 41.1, 40.4, 39.0, 38.6, 35.2, 35.1, 34.1, 33.1, 32.3, 30.7, 30.6, 30.6, 26.8, 23.6, 14.9, 14.0, 13.9, 6.7; high resolution mass spectrum (ES$^+$) m/z 951.4636 [(M+Na)$^+$; calcd for C$_{52}$H$_{68}$N$_2$O$_{13}$Na: 951.4669].

Biological Data (Analogues will be Referred to in Roman Numerals in Discussing Biological Data)

With (+)-phorboxazole A (XVIII) and the eight phorboxazole analogues in hand, biological evaluation against a diverse panel of human cancer cell lines was conducted in the laboratory of Professor George R. Pettit at the Cancer Research Institute of Arizona State University. Specifically, cancer growth inhibition efficacy was evaluated against the human cancer cell lines; BXP-3 (pancreatic), MCF-3 (breast), F-268 (CNS), NCI-H460 (non-small lung), KM20L2 (colon), and DU-145 (prostate) (Smith, et al. *Org. Lett.* 2005, 7, 4403; Smith, et al. *Org. Lett.* 2005, 8, 797). As a result of the biological testing, several analogues were found to be as active and in several cell lines, significantly more active than phorboxazole A. In addition to the potent congeners, several inactive analogues were identified, providing direct evidence of important functionality required for potent tumor cell growth inhibitory activity.

Evaluation of (+)-phorboxazole A (XVIII) against the human cancer cell line panel revealed an average growth inhibition (GI$_{50}$) of 5.0 nanomolar (nM), a value within experimental error of previously reported results (Table 1). Screening the previously disclosed (+)-Z-C(2-3)-C(45-46) alkynyl phorboxazole congener (XVIIaZ) (Uckun, et al. *Bioorg. Med. Chem. Lett.* 2001, 11, 1181) against the six cancer cell lines afforded an average GI$_{50}$ of 5.2 nM, comparable to the Forsyth analogue studies. While structurally more rigid than the C(45-46) vinyl bromide, the alkyne substitution does not appear to adversely affect the binding of the phorboxazole skeleton with cellular targets. Conversely, (+)-E-C(2-3)-C(45-46)-alkynyl phorboxazole analogue (XVIIaE) was found to be significantly less active than (XVIII) and (XVIIaZ). An average GI$_{50}$ of 281 nM was found, implicating the importance of the conformational geometry imparted by Z-C(2-3) macrocyclic enoate for potent activity.

Evaluation of C(45-46) alkenyl (XVIIc) and alkyl (XVIIb) analogues against the human cancer cell line panel revealed average GI$_{50}$ data of 4.1 and 3.1 nM respectively, values slightly more potent than (+)-phorboxazole A (ca. 5.0 nM). Specifically, alkyl congener (XVIIb) displayed single digit GI$_{50}$ values of 1.6 and 1.3 nM against the non-small lung and colon cancer cell lines. Not only does the greater flexibility of the C(45-46) alkenyl and alkyl congeners seem not to affect activity but, the decreased electronic density of these substitutions also does not seem to play a significant role in their biological properties. When vinyl chloride analogue (XVIId) was screened against the six human cancer cell lines however, extraordinary sub-nanomolar efficacy of 0.62, 0.49, 0.64, and 0.38 nM was observed against the pancreatic, CNS, non-small lung, and colon cancer cell lines, respectively. Though both sterically and conformationally very similar to (+)-phorboxazole A, the greater activity of (XVIId) may be accounted for by the small difference in electron deficiency between the vinyl chloride and bromide, possibly promoting a more favorable binding with the cell machinery responsible for the observed cytotoxicity.

As mentioned previously, the synthetically simplified C(11-15) acetal congeners (XVIIfZ) and (XVIIfE) were thought to impart a similar conformational geometry as the tetrahydropyran however, the importance of the C(13) hydroxyl was unknown. When screened against the six cancer cell lines, Z-C(2-3) acetal conger (XVIIfZ) revealed an average GI$_{50}$ value of 34.6 nM, and in particular 18.3 and 11.8 nM were observed for the breast and colon cancer cell lines, respectively. The E-acetal isomer (XVIIfE), however was found to be significantly less active. An average GI$_{50}$ of 943.5 nM was observed, reinforcing the importance of the Z-C(2-3) enoate conformational for potent activity. While the Z-acetal isomer was slightly less active than the corresponding C(11-15) tetrahydropyran series, a similar conformation does appear to be present relative to the tetrahydropyran based upon proton NMR. In addition, interactions with cellular targets by the C(13) hydroxyl does not appear to play a significant role toward the cytotoxicity of the phorboxazoles. In accord with the Forsyth data, the truncated central tetrahydropyran analogue (XVIIe) was found to be inactive across the entire cell line panel. This reinforces the need for an elaborate macrocyclic domain, possibly to impart a specific conformational geometry to the side chain relative to the macrocycle.

TABLE 1

Biological evaluation of phorboxazole analogues.

Phorboxazole A Analogues (XVIIa-d, XVIII)

C(11–15) Acetal Analogues (XVIIfZ-XVIIfE)

$GI_{50}$ (nM)

| | C(45–46) Sidechain R = | | BXPC-3 Pancreatic | MCF-3 Breast | F-268 CNS | NCI-H460 Non-Small Lung | KM20L2 Colon | DU-145 Prostate |
|---|---|---|---|---|---|---|---|---|
| (XVIII) | —CH=CH—Br | | 6.0 | 7.0 | 5.5 | 3.9 | 2.9 | 4.8 |
| (XVIIb) | —CH₂—CH₃ | | 3.2 | 3.9 | 3.5 | 1.6 | 1.3 | 5.0 |
| (XVIIc) | —CH=CH₂ | | 5.6 | 5.6 | 5.0 | 2.8 | 1.8 | 3.6 |
| (XVIId) | —CH=CH—Cl | | 0.62 | 1.7 | 0.49 | 0.64 | 0.38 | 2.5 |
| (XVIIaZ) | —C≡CH | Z-Macrocycle | 4.5 | 7.0 | 7.6 | 4.2 | 3.0 | 5.2 |
| (XVIIaE) | | E-Macrocycle | 200 | 230 | 510 | 200 | 140 | 410 |
| (XVIIfZ) | —C≡CH | Z-Acetal | 31.2 | 18.3 | 44.1 | 27.9 | 11.8 | 74.2 |
| (XVIIfE) | | E-Acetal | >1076 | 833 | 560 | >1076 | 990 | >1076 |
| (XVIIe) | Central Pyran | | >10,000 | >4,800 | >10,000 | >10,000 | >10,000 | >10,000 |

In summary, the C(45-46), C(2-3), and C(11-15) phorboxazole analogues have shed considerable light on the conformational and functional group requirements for potent tumor cell growth inhibitory activity. Specifically, C(45-46) alkynyl (XVIIaZ), alkenyl (XVIIc), and alkyl (XVIIb) congers displayed activity comparable to that of (+)-phorboxazole A. Vinyl chloride (XVIId) proved to be an extremely potent sub-nanomolar congener with activity greater than that of (+)-phorboxazole A. The macrocyclic C(2-3) geometrical conformation appears to play an extremely important role toward biological activity. For example, the Z isomer displayed activity two-orders of magnitude greater than that of the E-isomer in both the C(11-15) acetal and tetrahydropyran series. Finally, by mimicking the C(11-15) tetrahydropyran, acetal congener (XVIIfZ) proved to be both a synthetically and structurally simplified potent agent.

When ranges are used herein, such as carbon ranges or dosage ranges, all combinations and subcombinations of ranges and specific embodiments therein are intended to be included.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of formula XIX:

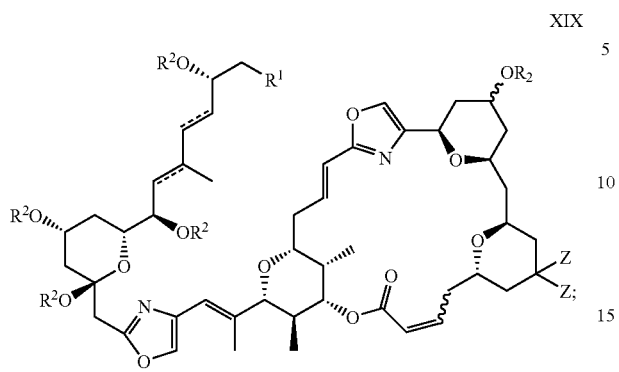

XIX wherein:
R$^1$ is alkyl, alkenyl, haloalkenyl, or alkynyl;
each R$^2$ is independently H, alkyl, aralkyl, or aryl;
each dotted line indicates independently the presence of a single or double bond; and
each Z is H or taken together form an exocyclic methylene moiety;
provided that when the compound of formula XIX has the structure:

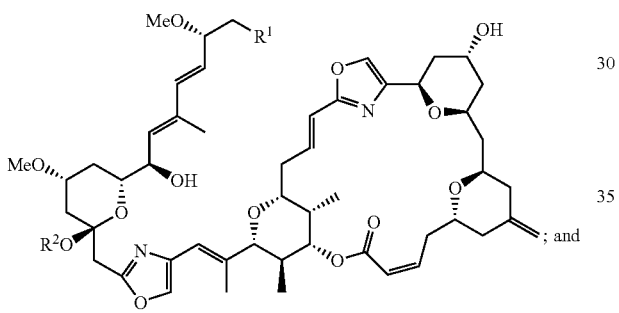

R$^2$ is H or methyl;
then R$^1$ is other than:

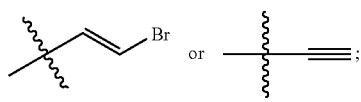

wherein said alkyl, alkenyl, alkynyl and aryl groups are optionally substituted with one or more of halo, alkyl, cycloalkyl, alkylcycloalkyl, alkenyl, alkynyl, aralkyl, aryl, heteroaryl, heteroaralkyl, spiroalkyl, heterocycloalkyl, hydroxyl, oxo, nitro, cyano, amino, —N-substituted amino (—NHR"), —N,N-disubstituted amino (—N(R")R"), carboxy, —O—C(═O)R", —C(═O)R", —OR", —C(═O)OR", —NHC(═O)R", aminocarbonyl, —N-substituted aminocarbonyl (—C(═O)NHR"), —N,N-disubstituted aminocarbonyl (—C(═O)N(R")R"), thiol, thiolato (—SR"), sulfonic acid (—SO$_3$H), phosphonic acid (—PO$_3$H), —P(═O)(OR")OR", S(═O)R", —S(═O)$_2$R", —S(═O)$_2$NH$_2$, —S(═O)$_2$NHR", —S(═O)$_2$NR"R", —NHS(═O)$_2$R", —NR"S(═O)$_2$R", —CF$_3$, —CF$_2$CF$_3$, —NHC(═O)NHR", —NHC(═O)NR"R", —NR"C(═O)NHR", —NR"C(═O)NR"R", or —NR"C(═O)R" where each R" is, independently, H, alkyl, cycloalkyl, alkenyl, aryl, aralkyl, heteroaryl, or heterocycloalkyl, or two R" groups that are attached to the same nitrogen atom can be taken together with the nitrogen atom to which they are attached to form a 3- to 8-membered heterocycloalkyl ring, wherein one or two of the heterocycloalkyl ring carbon atoms independently may be optionally replaced by —O—, —S—, —SO, —SO$_2$—, —NH—, —N(alkyl)-, —N(acyl)-, N(aryl)-, or —N(aroyl)- groups.

2. A compound of claim 1 of the following formula:

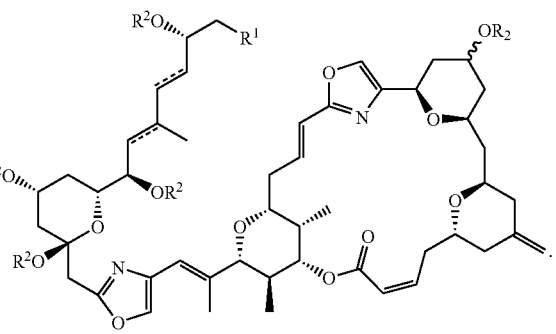

3. A compound of claim 1 of the following formula:

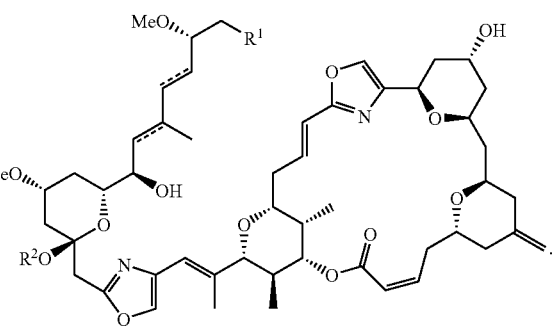

4. A compound of claim 3 wherein R$^1$ is:

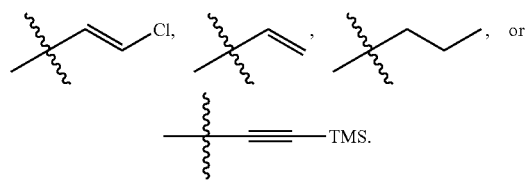

5. A process for preparing a compound of formula XIX:

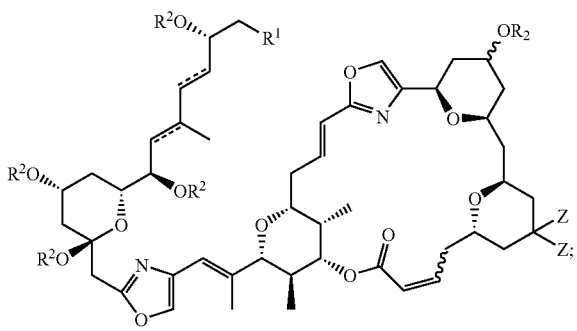

XIX wherein:
R$^1$ is alkyl, alkenyl, haloalkenyl, or alkynyl;
each R$^2$ is independently H, alkyl, aralkyl, aryl, or an hydroxyl protecting group;

each dotted line indicates independently the presence of a single or double bond; and each Z is H or taken together form an exocyclic methylene moiety, comprising the steps of:

contacting a compound of formula XX:

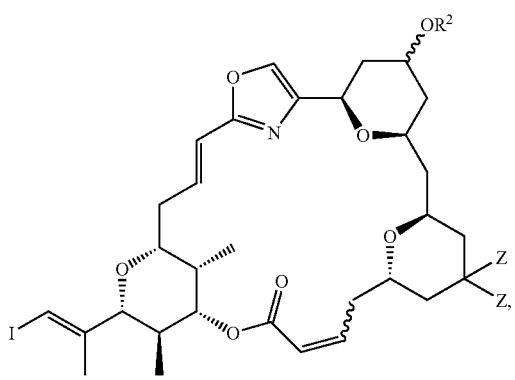

with a compound of formula XXI:

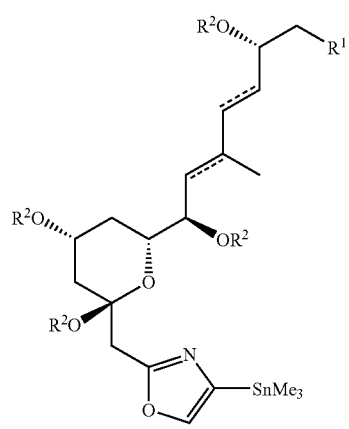

wherein:

R¹ is alkyl, alkenyl, haloalkenyl, or alkynyl; and each R² is independently H, alkyl, aralkyl, aryl, or hydroxyl protecting group;

for a time and under conditions effective to provide a compound of formula XIX;

wherein said alkyl, alkenyl, alkynyl and aryl groups are optionally substituted with one or more of halo, alkyl, cycloalkyl, alkylcycloalkyl, alkenyl, alkynyl, aralkyl, aryl, heteroaryl, heteroaralkyl, spiroalkyl, heterocycloalkyl, hydroxyl, oxo, nitro, cyano, amino, —N-substituted amino (—NHR"), —N,N-disubstituted amino (—N(R")R"), carboxy, —O—C(=O)R", —C(=O)R", —OR", —C(=O)OR", —NHC(=O)R", aminocarbonyl, —N-substituted aminocarbonyl (—C(=O)NHR"), —N,N-disubstituted aminocarbonyl (—C(=O)N(R")R"), thiol, thiolato (—SR"), sulfonic acid (—SO₃H), phosphonic acid (—PO₃H), —P(=O)(OR")OR", S(=O)R", —S(=O))₂R", —S(=O)₂NH₂, —S(=O)₂NHR", —S(=O)NR"R", —NHS(=O)₂R", —NR"S(=O)₂R", —CF₃, —CF₂CF₃, —NHC(=O)NHR", —NHC(=O)NR"R", —NR"C(=O)NHR", —NR"C(=O)NR"R", or —NR"C(=O)R" where each R" is, independently, H, alkyl, cycloalkyl, alkenyl, aryl, aralkyl, heteroaryl, or heterocycloalkyl, or two R" groups that are attached to the same nitrogen atom can be taken together with the nitrogen atom to which they are attached to form a 3- to 8-membered heterocycloalkyl ring, wherein one or two of the heterocycloalkyl ring carbon atoms independently may be optionally replaced by —O—, —S—, —SO, —SO₂—, —NH—, —N(alkyl)-, —N(acyl)-, N(aryl)-, or —N(aroyl)- groups.

6. A pharmaceutical composition comprising a pharmaceutically acceptable carrier and a compound according to claim 1.

7. A pharmaceutical composition comprising a pharmaceutically acceptable carrier and a compound according to claim 4.

8. A method for treating cancer in a patient in need thereof, comprising the step of:

administering to said patient an effective amount of a compound of claim 1, wherein the cancer treated is selected from the group consisting of pancreatic, breast, non-small lung, colon, and prostate cancers.

9. A compound of formula XXII:

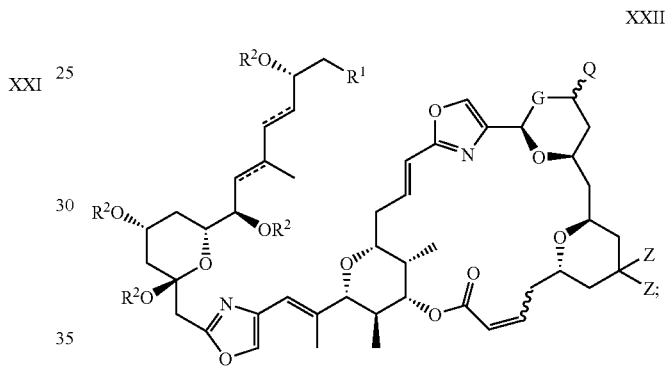

wherein:

G is —O— or —CH₂—;

Q is H or OR², provided that when G is —O—, then Q is H;

R¹ is alkyl, alkenyl, haloalkenyl, or alkynyl;

each R² is independently H, alkyl, aralkyl, or aryl;

each dotted line indicates independently the presence of a single or double bond; and each Z is H or taken together form an exocyclic methylene moiety;

provided that when the compound of formula XXII has the structure:

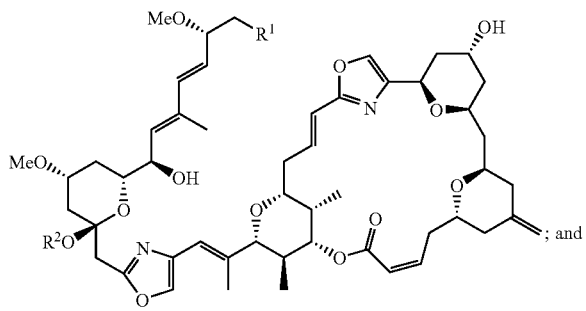

R² is H or methyl;

then R¹ is other than:

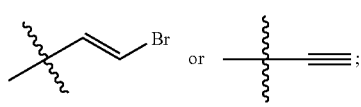

wherein said alkyl, alkenyl, alkynyl and aryl groups are optionally substituted with one or more of halo, alkyl, cycloalkyl, alkylcycloalkyl, alkenyl, alkynyl, aralkyl, aryl, heteroaryl, heteroaralkyl, spiroalkyl, heterocycloalkyl, hydroxyl, oxo, nitro, cyano, amino, —N-substituted amino (—NHR″), —N,N-disubstituted amino (—N(R″)R″), carboxy, —O—C(═O)R″, —C(═O)R″, —OR″, —C(═O)OR″, —NHC(═O)R″, aminocarbonyl, —N-substituted aminocarbonyl (—C(═O)NHR″), —N,N-disubstituted aminocarbonyl (—C(═O)N(R″)R″), thiol, thiolato (—SR″), sulfonic acid (—SO$_3$H), phosphonic acid (—PO$_3$H), —P(═O)(OR″)OR″, S(═O)R″, —S(═O)$_2$R″, —S(═O)$_2$NH$_2$, —S(═O)$_2$NHR″, —S(═O)$_2$NR″R″, —NHS(═O)$_2$R″, —NR″S(═O)$_2$R″, —CF$_3$, —CF$_2$CF$_3$, —NHC(═O)NHR″, —NHC(═O)NR″R″, —NR″C(═O)NHR″, —NR″C(═O)NR″R″, or —NR″C(═O)R″ where each R″ is, independently, H, alkyl, cycloalkyl, alkenyl, aryl, aralkyl, heteroaryl, or heterocycloalkyl, or two R″ groups that are attached to the same nitrogen atom can be taken together with the nitrogen atom to which they are attached to form a 3- to 8-membered heterocycloalkyl ring, wherein one or two of the heterocycloalkyl ring carbon atoms independently may be optionally replaced by —O—, —S—, —SO, —SO$_2$—, —NH—, —N(alkyl)-, —N(acyl)-, N(aryl)-, or —N(aroyl)- groups.

10. A compound of claim 9 of the following formula:

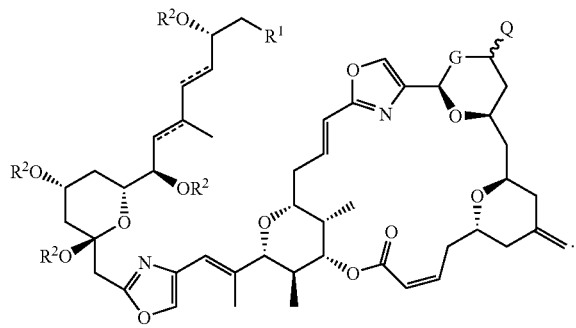

11. A compound of claim 9 of the following formula:

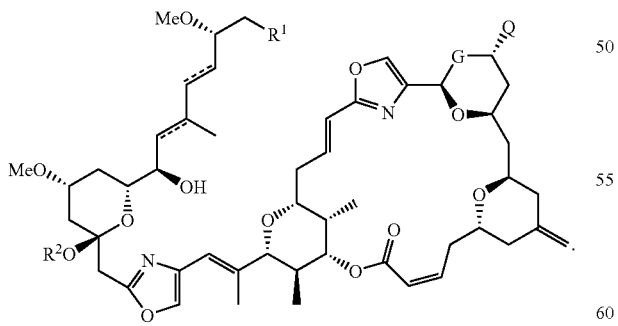

12. A compound of claim 11 wherein R$^1$ is ethyl, ethenyl, or ethynyl.

13. A compound of claim 12 wherein the ethenyl is optionally substituted with halo.

14. A compound of claim 13 wherein the halo is bromo or chloro.

15. A compound of claim 12 wherein R$^1$ is:

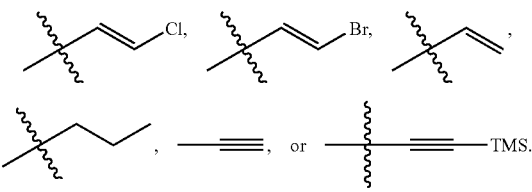

16. A compound of claim 12 wherein R$^1$ is:

17. A process for preparing a compound of formula XXII:

XXII

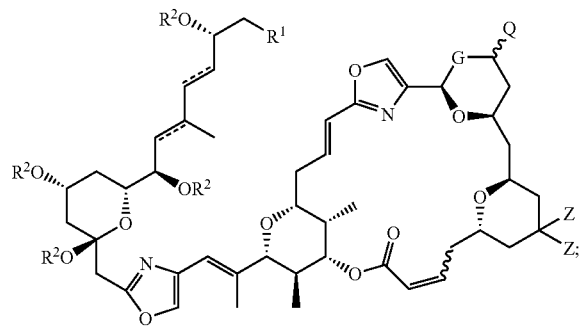

wherein:

G is —O— or —CH$_2$—;

Q is H or OR$^2$, provided that when G is —O—, then Q is H;

R$^1$ is alkyl, alkenyl, haloalkenyl, or alkynyl;

each R$^2$ is independently H, alkyl, aralkyl, aryl, or an hydroxyl protecting group;

each dotted line indicates independently the presence of a single or double bond; and each Z is H or taken together form an exocyclic methylene moiety, comprising the steps of:

contacting a compound of formula XXIII:

XXIII

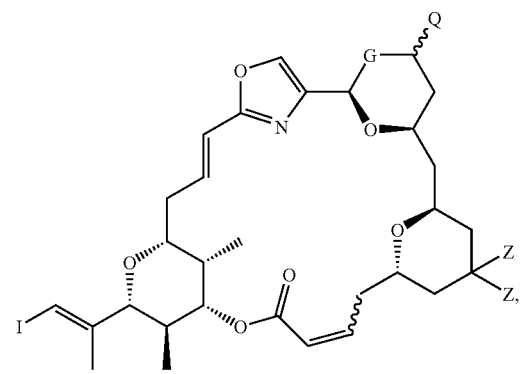

with a compound of formula XXIV:

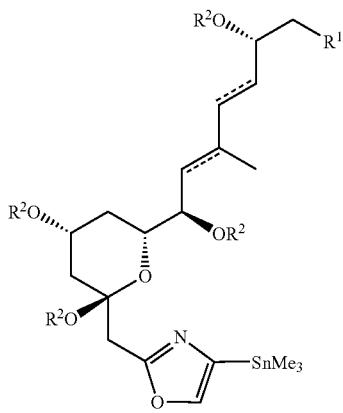

wherein:
$R^1$ is alkyl, alkenyl, haloalkenyl, or alkynyl; and
each $R^2$ is independently H, alkyl, aralkyl, aryl, or hydroxyl protecting group;
for a time and under conditions effective to provide a compound of formula XXIII;
wherein said alkyl, alkenyl, alkynyl and aryl groups are optionally substituted with one or more of halo, alkyl, cycloalkyl, alkylcycloalkyl, alkenyl, alkynyl, aralkyl, aryl, heteroaryl, heteroaralkyl, spiroalkyl, heterocycloalkyl, hydroxyl, oxo, nitro, cyano, amino, —N-substituted amino (—NHR"), —N,N-disubstituted amino (—N(R")R"), carboxy, —O—C(=O)R", —C(=O)R", —OR", —C(=O)OR", —NHC(=O)R", aminocarbonyl, —N-substituted aminocarbonyl (—C(=O)NHR"), —N,N-disubstituted aminocarbonyl (—C(=O)N(R")R"), thiol, thiolato (—SR"), sulfonic acid (—SO₃H), phosphonic acid (—PO₃H), —P(=O)(OR")OR", S(=O)R", —S(=O)₂R, —S(=O)₂NH₂, —S(=O)₂NHR", —S(=O)₂NR"R", —NHS(=O)₂R", —NR"S(=O)₂R", —CF₃, —CF₂CF₃, —NHC(=O)NHR", —NHC(=O)NR"R", —NR"C(=O)NHR", —NR"C(=O)NR"R", or —NR"C(=O)R" where each R" is, independently, H, alkyl, cycloalkyl, alkenyl, aryl, aralkyl, heteroaryl, or heterocycloalkyl, or two R" groups that are attached to the same nitrogen atom can be taken together with the nitrogen atom to which they are attached to form a 3- to 8- membered heterocycloalkyl ring, wherein one or two of the heterocycloalkyl ring carbon atoms independently may be optionally replaced by —O—, —S—, —SO, —SO₂—, —NH—, —N(alkyl-, —N(acyl)-, N(aryl)-, or —N(aroyl)-groups.

18. A pharmaceutical composition comprising a pharmaceutically acceptable carrier and a compound according to claim 9.

19. A pharmaceutical composition comprising a pharmaceutically acceptable carrier and a compound according to claim 16.

20. A method of inducing apoptosis in malignant cells in vitro, comprising the step of:
contacting said cells with an effective amount of a compound according to claim 9.

21. A method for treating cancer in a patient in need thereof, comprising the step of:
administering to said patient an effective amount of a compound of claim 9, wherein the cancer treated is selected from the group consisting of pancreatic, breast, non-small lung, colon, and prostate cancers.

* * * * *